US008440411B2

(12) United States Patent
St. Croix et al.

(10) Patent No.: US 8,440,411 B2
(45) Date of Patent: May 14, 2013

(54) DIFFERENTIAL GENE EXPRESSION IN PHYSIOLOGICAL AND PATHOLOGICAL ANGIOGENESIS

(75) Inventors: Brad St. Croix, Frederick, MD (US); Steven Seaman, Martinsburg, WV (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/052,878

(22) Filed: Mar. 21, 2011

(65) Prior Publication Data

US 2011/0207141 A1 Aug. 25, 2011

Related U.S. Application Data

(63) Continuation of application No. 12/514,297, filed as application No. PCT/US2007/072395 on Jun. 28, 2007, now abandoned.

(60) Provisional application No. 60/858,068, filed on Nov. 9, 2006, provisional application No. 60/879,457, filed on Jan. 8, 2007.

(51) Int. Cl.
*G01N 33/53* (2006.01)
(52) U.S. Cl.
USPC ............................................................ 435/7.1
(58) Field of Classification Search .................. None
See application file for complete search history.

(56) References Cited

U.S. PATENT DOCUMENTS

| | | | |
|---|---|---|---|
| 7,527,969 B2 | 5/2009 | Mather et al. | |
| 7,718,774 B2 | 5/2010 | Mather et al. | |
| 7,939,267 B2 * | 5/2011 | Moore et al. | 435/7.1 |

FOREIGN PATENT DOCUMENTS

| | | |
|---|---|---|
| EP | 1 619 257 A1 | 1/2006 |
| WO | WO 02/083874 A3 | 10/2002 |
| WO | WO 03/080800 A2 | 10/2003 |
| WO | WO 03/085134 A2 | 10/2003 |
| WO | WO 04/001004 A3 | 12/2003 |
| WO | WO 2004/005531 A3 | 1/2004 |
| WO | WO 2004/005883 A2 | 1/2004 |
| WO | WO 2004/005883 A3 | 1/2004 |
| WO | WO 2004/016758 A2 | 2/2004 |
| WO | WO 2004/016758 A3 | 2/2004 |
| WO | WO 2004/078192 A1 | 9/2004 |
| WO | WO 2004/078942 | 9/2004 |
| WO | WO 2004081198 * | 9/2004 |
| WO | WO 2005/042725 A2 | 5/2005 |
| WO | WO2008057632 A1 * | 5/2008 |

OTHER PUBLICATIONS

Seaman et al . Genes that distinguish physiological and pathological angiogenesis. Cancer Cell 11:539-554(2007).*

Sinha et al. Upregulation of collagen VIII following porcine coronary artery angioplasty is related to smooth muscle cell migration not angiogenesis. Int J Exp Pathol. Oct. 2001;82(5):295-302.*
Odorisio et al.Mice overexpressing placenta growth factor exhibit increased vascularization and vessel permeability. Journal of Cell Science 115, 2559-2567 (2002).*
Takahashi et al. Identification of receptor genes in renal cell carcinoma associated with angiogenesis by differential hybridization technique. Biochemical and Biophysical Research Communications 257, 855-859 (1999).*
Adini, et al., "Placental Growth Factor is a Survival Factor for Tumor Endothelial Cells and Macrophages", *Cancer Res.*, vol. 62, pp. 2749-2752, 2002.
Benbrook, et al., "A new retinoic acid receptor identified from a hepatocellular carcinoma", Abstract Only, *Nature*, vol. 333, No. 6174, pp. 669-672, 1988.
Blomeke, et al., "Identification of N-Acetyltransferase 2 Genotypes by Continuous Monitoring of Fluorogenic Hybridization Probes", *Analytical Biochemistry*, vol. 275, pp. 93-97, 1999.
Bodey, et al., "Failure of Cancer Vaccines: The Significant Limitations of this Approach to Immunotherapy", *Anticancer Res.*, vol. 20, pp. 2665-2676, 2000.
Broll, et al., "CD137 expression in tumor vessel walls. High correlation with malignant tumors", Abstract Only, *Am. J. Clin. Pathol.*, vol. 115, No. 4, pp. 543-549, 2001.
Bronger, et al., "ABCC drug efflux pumps and organic anion uptake transporters in human gliomas and the blood-tumor barrier", Abstract Only, *Cancer Res.*, vol. 65, No. 24, pp. 11419-11428, 2005.
Brooks, et al., "Requirement of vascular integrin alpha v beta 3 angiogenesis", Abstract Only, *Science*, vol. 264, No. 5158, pp. 569-571, 1994.
Bullock, et al., "Hepatitis C Genotype Determination by Melting Curve Analysis with a Single Set of Fluorescence Resonance Energy Transfer Probes", *Clinical Chem.*, vol. 48, No. 12, pp. 2147-2154, 2002.
Carmeliet, et al., "Synergism between vascular endothelial growth factor and placental growth factor contributes to angiogenesis and plasma extravasation in pathological conditions", *Nature Medicine*, vol. 7, No. 5, pp. 575-583, 2001.
Carson-Walter, et al., "Cell Surface Tumor Endothelial Markers Are Conserved in Mice and Humans", *Cancer Res.*, vol. 61, pp. 6649-6655, 2001.
Chen, et al., "Novel endothelial cell markers in hepatocellular carcinoma", *Modern Pathology*, pp. 1-13, 2004.
Comincini, et al., "Differential expression of the prion-like protein doppel gene (PRND) in astrocytomas: a new molecular marker potentially involved in tumor progression", Abstract Only, *Anticancer Res.*, vol. 24, No. 3a, pp. 1507-1517, 2004.
Cox, et al., "Apelin, the ligand for the endothelial G-protein-coupled receptor, APJ, is a potent angiogenic factor required for normal vascular development of the frog embryo", Abstract Only, *Dev. Biol.*, vol. 296, No. 1, pp. 177-189, 2006.

(Continued)

Primary Examiner — Maher Haddad
(74) Attorney, Agent, or Firm — Klarquist Sparkman, LLP

(57) ABSTRACT

Methods of inhibiting pathological angiogenesis in a subject are disclosed. In particular examples, the method includes administering a therapeutically effective amount of a composition to a subject wherein the composition includes a specific binding agent that preferentially binds to one or more pathological angiogenesis marker proteins including Vscp, CD276, ETSvg4 (Pea3), CD137(4-1BB), MiRP2, Ubiquitin D (Fat10), Doppel (prion-PLP), Apelin, Plgf, Ptprn (IA-2), CD109, Ankylosis, and collagen VIIIα1. In additional examples, methods to deliver a therapeutic agent to a brain or liver endothelial cell are also disclosed.

8 Claims, 13 Drawing Sheets

OTHER PUBLICATIONS

Cubelos, et al., "Amino acid transporter SNAT5 localizes to glial cells in the rat brain", Abstract Only, *Glia.*, vol. 49, No. 2, pp. 230-244, 2005.

Dame, et al., "Hepatic Erythropoietin Gene Regulation by GATA-4", *J. Biol. Chem.*, vol. 279, No. 4, pp. 2955-2961, 2004.

Davies, et al., "Levels of expression of endothelial markers specific to tumour-associated endothelial cells and their correlation with prognosis in patients with breast cancer", Abstract Only, *Clin. Exp. Metastasis*, vol. 21, No. 1, pp. 31-37, 2004.

Di Tomaso, et al., "Mosaic Tumor Vessels: Cellular Basis and Ultrastructure of focal Regions Lacking Endothelial Cell Markers", *Cancer Res.*, vol. 65, No. 13, pp. 5740-5749, 2005.

Farrell and Pardridge, "Blood-brain barrier glucose transporter is asymmetrically distributed on brain capillary endothelial luminal and ablumenal membranes: An electron microscopic immunogold study", *Proc. Natl. Acad. Sci. USA*, vol. 88, pp. 5779-5783, 1991.

Gao, et al., "Localization of the Organic Anion Transporting Polypeptide 2 (Oatp2) in Capillary Endothelium and Choroid Plexus Epithelium of Rat Brain", *Journal of Histochemistry & Cytochemistry*, vol. 47, No. 10, pp. 1255-1263, 1999.

Gao, et al., "Organic Anion-Transporting Polypeptides Mediate Transport of Opioid Peptides across Blood-Brain Barrier", *J. Pharm. Exp. Therap.*, vol. 294, No. 1, pp. 73-79, 2000.

Hara and Seon, "Complete suppression of in vivo growth of human leukemia cells by specific immunotoxins: Nude mouse models", *Proc. Natl. Acad. Sci. USA*, vol. 84, pp. 3390-3394, 1987.

Hubatsch, et al., "Human glutathione transferase A4-4: an alpha class enzyme with high catalytic efficiency in the conjugation of 4-hydroxynonenal and other genotoxic products of lipid peroxidation", Abstract Only, *Biochem J.*, vol. 330, Pt. 1, pp. 175-179, 1998.

Iguchi, et al., "PEA3 and AP-1 are required for constitutive IL-8 gene expression in hepatoma cells", Abstract Only, *Biochem. Biophys. Res. Commun.*, vol. 279, No. 1, pp. 166-171, 2000.

Inoue, et al., "Molecular Cloning and Sequence Analysis of a cDNA Encoding a Porcine Kidney Renin-binding Protein", *J. Biol. Chem.*, vol. 265, No. 12, pp. 6556-6561, 1990.

Jukkola, et al., "Drape1 expression during mouse embryonic development", Abstract Only, *Gene Expr. Patterns*, vol. 4, No. 6, pp. 755-762, 2004.

Kageyama, et al., "The 4F2hc/LAT1 complex transports L-DOPA across the blood-brain barrier", Abstract Only, *Brain Res.*, vol. 879, Nos. 1-2, pp. 115-121, 2000.

Kasai, et al., "Apelin is a novel angiogenic factor in retinal endothelial cells", Abstract Only, *Biochem. Biophys. Res. Commun.*, vol. 325, No. 2, pp. 395-400, 2004.

Kim and Nie, "Targeted cancer nanotherapy", *Nano Today*, vol. 1369, pp. 28-33, 2005.

Knolle and Limmer, "Control of immune responses by scavenger liver endothelial cells", *Swiss Med. Wkly*, vol. 133, pp. 501-506, 2003.

Lee, et al., "FAT 10 expression is upregulated in liver and other cancers", *Cancer Weekly.*, via *NewsRx*, 1 page, 2003.

Levin, et al., "Developmental changes in the expression of genes involved in cholesterol biosynthesis and lipid transport in human and rat fetal and neonatal livers", Abstract Only, *Biochim. Biophys. Acta.*, vol. 1003, No. 3, pp. 293-300, 2003.

Li and Wan, "Differentiation and antiproliferation effects of retinoic acid receptor beta in hepatoma cells", Abstract Only, *Cancer Lett.*, vol. 124, No. 2, pp. 205-211, 1998.

Li, et al., "Physiological Expression of the Gene for PrP-Like Protein, PrPLP/Dpl, by Brain Endothelial Cells and its Ectopic Expression in Neurons of PrP-Deficient Mice Ataxic Due to Purkinje Cell Degeneration", *Amer. J. Pathol.*, vol. 157, No. 5, pp. 1447-1452, 2000.

Liu, et al., "Characterization of a Novel C-type Lectin-like Gene, LSECtin", *J. Biol. Chem.*, vol. 279, No. 18, pp. 18748-18758, 2004.

Liu, et al., "Peptidoglycan Recognition Proteins", *J. Biol. Chem.*, vol. 276, No. 37, pp. 34686-34694, 2001.

Madden, et al., "Vascular gene expression in nonneoplastic and malignant brain", *Amer. J. Pathol.*, vol. 165, No. 2, pp. 601-608, 2004.

Matsumoto, et al., "The Functional Binding Site for the C-type Lectin-like Natural Killer Cell Receptor Ly49A Spans Three Domains of Its Major Histocompatibility Complex Class I Ligand", *J. Exp. Med.*, vol. 193, No. 2, pp. 147-157, 2001.

Mesli, et al., "Distribution of the lipolysis stimulated receptor in adult and embryonic murine tissues and lethality of LSR-/- embryos at 12.5 to 14.5 days of gestation", *Eur. J. Biochem*, vol. 271, pp. 3103-3114, 2004.

Mizutani, et al., "Identification of the human sphingolipid C4-hydroxylase, hDES2, and its up-regulation during keratinocyte differentiation", *FEBS Letter*, vol. 563, pp. 93-97, 2004.

Mori, et al., "Rat organic anion transporter 3 (rOAT3) is responsible for brain-to-blood efflux of homovanillic acid at the abluminal membrane of brain capillary endothelial cells", Abstract Only, *J. Cereb. Blood Flow Metab.*, vol. 23, No. 4, pp. 432-440, 2003.

Muro, et al., "Defect of Fc receptors and phenotypical changes in sinusoidal endothelial cells in human liver cirrhosis", Abstract Only, *Am. J. Pathol.*, vol. 143, No. 1, pp. 105-120, 1993.

Mustelin, "Are other protein tyrosine phosphatases than *PTPN22* associated with autoimmunity?", Abstract Only, *Seminars in Immunology*, vol. 18, No. 4, pp. 254-260, 2006.

Mutuberria, et al., "Isolation of human antibodies to tumor-associated endothelial cell markers by in vitro human endothelial cell selection with phage display libraries", *J. Immunological Methods*, vol. 287, pp. 31-47, 2004.

Nadal, et al., "Down-regulation of the mitochondrial 3-hydroxy-3-methylglutaryl-CoA synthase gene by insulin: the role of the forkhead transcriptions factor FKHRL1", *Biochem. J.*, vol. 366, pp. 289-297, 2002.

Nanda and St. Croix, "Tumor endothelial markers: new targets for cancer therapy", Abstract Only, *Curr. Opin. Oncol.*, vol. 16, No. 1, pp. 44-49, 2004.

Nogusa, et al., "Expression of zinc finger protein ZPR1 mRNA in brain is up-regulated in mice fed a high-fat diet", Abstract Only, *Int. J. Mol. Med.*, vol. 17, No. 3, pp. 491-496, 2006.

Ohtsuki, et al., "Localization of organic anion transporting polypeptide 3 (oatp3) in mouse brain parenchymal and capillary endothelial cells", *J. Neurochem.*, vol. 90, pp. 743-749, 2004.

Ohtsuki, et al., "Mouse Reduced in Osteosclerosis Transporter Functions as an Organic Anion Transporter 3 and is Localized at Abluminal Membrane of Blood-Brain Barrier", *J. Pharm. Exp. Therap.*, vol. 309, No. 3, pp. 1273-1281, 2004.

Ohtsuki, et al., "Role of blood-brain barrier organic anion transporter 3 (OAT3) in the efflux of indoxyl sulfate, a uremic toxin: its involvement in neurotransmitter metabolite clearance from the brain", Abstract Only, *J. Neurochem.*, vol. 83, No. 1, pp. 57-66, 2002.

Pai, et al., "Identification of endothelial genes up-regulated in vivo", *Gene: An International Journal on Genes and Genomes*, vol. 347, No. 1, pp. 21-33, 2005.

Pardridge, et al., "Brain-type Glucose Transporter (GLUT-1) is Selectively Localized to the Blood-Brain Barrier", *J. Biol. Chem.*, vol. 265, No. 29, pp. 18035-18040, 1990.

Parker, et al., "Alterations in vascular gene expression in invasive breast carcinoma", *Cancer Res.*, vol. 64, No. 21, pp. 7857-7866, 2004.

Perala, et al., "The expression of plexins during mouse embryogenesis", Abstract Only, *Gene Expr. Patterns.*, vol. 5, No. 3, pp. 355-362, 2005.

Porter, et al., "SAGE and related approaches for cancer target identification", Abstract Only, *Drug Discovery Today*, vol. 11, Nos. 3-4, pp. 110-118, 2006.

Qian, et al., "Mouse Wnt9b transforming activity, tissue-specific expression, and evolution", Abstract Only, *Genomics*, vol. 81, No. 1, pp. 34-46, 2003.

Reynolds, et al., "Enhanced pathological angiogenesis in mice lacking $\beta_3$ integrin or $\beta_3$ and $\beta_5$ integrins", *Nature Medicine*, vol. 8, No. 1, pp. 27-34, 2002.

Rmali, et al., "Prognostic values of tumor endothelial markers in patients with colorectal cancer", *World J. Gastroenterology*, vol. 11, No. 9, pp. 1283-1286, 2005.

Ross, et al., "Validation of a five reagent immunohistochemistry assay for prognostication of estrogen-receptor expressing breast cancer", Abstract Only #10081, *Amer. Soc. Clin. Oncology*.

Saint-Geniez, et al., "Expression of the murine msr/apj receptor and its ligand apelin is upregulated during formation of the retinal vessels", Abstract Only, *Mech. Dev.*, vol. 110, Nos. 1-2, pp. 183-186, 2002.

Schnepp, et al., "Mouse Testican-2", *J. Biol. Chem.*, vol. 280, No. 12, pp. 11274-11280, 2005.

Seon, et al., "Monoclonal antibody SN2 defining a human T cell leukemia-associated cell surface glycoprotein", Abstract Only, *J. Immunology*, vol. 132, No. 4, pp. 2089-2095, 1984.

Seth and Watson, "ETS transcription factors and their emerging roles in human cancer", Abstract Only, *Euro. J. Cancer*, vol. 41, No. 16, pp. 2462-2478, 2005.

St. Croix, et al., "Genes expressed in human tumor endothelium", *Science*, vol. 289, No. 5482, pp. 1197-1202, 2000.

Sun, et al., "Mouse B7-H3 induces antitumor immunity", *Gene Therapy*, vol. 10, pp. 1728-1734, 2003.

Sugiyama, et al., "Functional Characterization of Rat Brain-specific Organic Anion Transporter (Oatp14) at the Blood-Brain Barrier", *J. Biol. Chem.*, vol. 278, No. 44, pp. 43489-43495, 2003.

Tsuchihara, et al., "Ckap2 Regulates Aneuploidy, Cell Cycling, and Cell Death in a p53-Dependent Manner", *Cancer Res.*, vol. 65, No. 15, pp. 6685-6691, 2005.

Van Beijnum, et al., "In silico analysis of angiogenesis associated gene expression identifies angiogenic stage related profiles", *Reviews on Cancer*, vol. 1755, No. 2, pp. 121-134, 2005.

Wang, et al., "Role of the Progressive Ankylosis Gene (*ank*) in Cartilage Mineralization", *Molecular Cell. Biol.*, vol. 25, No. 1, pp. 312-323, 2005.

White, et al., "Antibody-Targeted Immunotherapy for Treatment of Malignancy", *Annu. Rev. Med.*, vol. 52, pp. 125-145, 2001.

Wijchers, et al., "Identification of forkhead transcription factors in cortical and dopaminergic areas of the adult murine brain", *Brain Res.*, vol. 1068, pp. 23-33, 2006.

Wride, et al., "Expression profiling and gene discovery in the mouse lens", *Molecular Vision*, vol. 9, pp. 360-396, 2003.

Xu, et al., "nc1 Domain of Human Type VIII Collagen ($\alpha$ 1) Inhibits Bovine Aortic Endothelial Cell Proliferation and Causes Cell Apoptosis", *Biochem. Biophys. Res. Commun.*, vol. 289, pp. 264-268, 2001.

Yeh, et al., "Upregulation of Pleiotrophin Gene Expression in Developing Microvasculature, Macrophages, and Astrocytes after Acute Ischemic Brain Injury", *J. Neuroscience*, vol. 18, No. 10, pp. 3699-3707, 1998.

Yen, et al., "Molecular Cloning of a Lipolysis-stimulated Remnant Receptor Expressed in the Liver", *J. Biol. Chem.*, vol. 274, No. 19, pp. 13390-13398, 1999.

Zagzag, et al., "Tenascin-C expression by angiogenic vessels in human astrocytomas and by human brain endothelial cells in vitro", Abstract Only, *Cancer Res.*, vol. 56, No. 1, pp. 182-189, 1996.

Zhang, et al., "CD109 expression in squamous cell carcinoma of the uterine cervix", Abstract Only, *Pathol. Int.*, vol. 55, No. 4, pp. 165-169, 2005.

Zhaohui, et al., "Molecular Cloning of a Lipolysis-stimulated Remnant Receptor Expressed in the Liver", *Neuron*, vol. 45, pp. 353-359, 2005.

Gen Bank Accession "CD276 antigen isoform a [*Homo sapiens*]".

\* cited by examiner

SEQUENCE LISTING

```
<160> NUMBER OF SEQ ID NOS: 234

<210> SEQ ID NO 1
<211> LENGTH: 17
<212> TYPE: DNA
<213> ORGANISM: Artificial sequence
<220> FEATURE:
<223> OTHER INFORMATION: Synthetic nucleic acid SAGE tag
```

<400> SEQUENCE: 1
agaaggacct cggaggc                                                  17

<210> SEQ ID NO 2
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 2
tgcttccagt atgtgga                                                  17

<210> SEQ ID NO 3
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 3
gtgtttgtgt ggccctc                                                  17

<210> SEQ ID NO 4
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 4
agaaggactt cggaggc                                                  17

<210> SEQ ID NO 5
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 5
cctgaattgc tgaggcc                                                  17

<210> SEQ ID NO 6
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 6
agggacttca gtccctc                                                  17

<210> SEQ ID NO 7
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 7
ataaaaaata tttactg                                                  17

<210> SEQ ID NO 8
<211> LENGTH: 17

```
<212> TYPE: DNA
<213> ORGANISM: Artificial sequence
<220> FEATURE:
<223> OTHER INFORMATION: Synthetic nucleic acid SAGE tag

<400> SEQUENCE: 8
ccccaccaaa aatcaat                                                    17

<210> SEQ ID NO 9
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 9
aaatcctttc actttgg                                                    17

<210> SEQ ID NO 10
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 10
taaactactt ctcttgt                                                    17

<210> SEQ ID NO 11
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 11
tttcaatctt atcttaa                                                    17

<210> SEQ ID NO 12
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 12
ggtctgacag ctccggt                                                    17

<210> SEQ ID NO 13
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 13
gaccgggtac ccgcaaa                                                    17

<210> SEQ ID NO 14
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 14
acaaacctct aaggatg                                                    17
```

<210> SEQ ID NO 15
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 15
cgctgcaagg gatcgtg                                          17

<210> SEQ ID NO 16
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 16
taaatgaata aaagcat                                          17

<210> SEQ ID NO 17
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 17
gggtaaatga tgactac                                          17

<210> SEQ ID NO 18
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 18
ggcaagttcc ccttttt                                          17

<210> SEQ ID NO 19
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 19
gagtggttcc ctgatgt                                          17

<210> SEQ ID NO 20
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 20
ctctcagaac aaagact                                          17

<210> SEQ ID NO 21
<211> LENGTH: 17
<212> TYPE: DNA
<213> ORGANISM: Artificial sequence
<220> FEATURE:
<223> OTHER INFORMATION: Synthetic nucleic acid SAGE tag

```
<400> SEQUENCE: 21
ccaacctact ctattgc                                                    17

<210> SEQ ID NO 22
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 22
agaggaggta tgggagg                                                    17

<210> SEQ ID NO 23
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 23
aggagagtgt ctaaaag                                                    17

<210> SEQ ID NO 24
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 24
cacaaatatt taccatt                                                    17

<210> SEQ ID NO 25
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 25
agtttccacc tttattc                                                    17

<210> SEQ ID NO 26
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 26
gtggtaagag aagctcc                                                    17

<210> SEQ ID NO 27
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 27
tcactgccct gaaagac                                                    17

<210> SEQ ID NO 28
<211> LENGTH: 17
```

```
<212> TYPE: DNA
<213> ORGANISM: Artificial sequence
<220> FEATURE:
<223> OTHER INFORMATION: Synthetic nucleic acid SAGE tag

<400> SEQUENCE: 28
acttacattc cactgct                                                   17

<210> SEQ ID NO 29
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 29
tgatgtttca gtgcttt                                                   17

<210> SEQ ID NO 30
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 30
agtcctcccc tcagggc                                                   17

<210> SEQ ID NO 31
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 31
cttcctagtc tttttga                                                   17

<210> SEQ ID NO 32
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 32
ttttagtaag aaagcag                                                   17

<210> SEQ ID NO 33
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 33
cctcagcacg ccctcag                                                   17

<210> SEQ ID NO 34
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 34
ggacccctga ctgtgat                                                   17
```

<210> SEQ ID NO 35
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 35
ctgctgtgga ccagagc                                                17

<210> SEQ ID NO 36
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 36
aatgtgttct atccctc                                                17

<210> SEQ ID NO 37
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 37
acttcagaat gtgccag                                                17

<210> SEQ ID NO 38
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 38
gtggatgcca atttgcc                                                17

<210> SEQ ID NO 39
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 39
ataccaaaca cgccaat                                                17

<210> SEQ ID NO 40
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 40
gtgcatactt gaggggg                                                17

<210> SEQ ID NO 41
<211> LENGTH: 17
<212> TYPE: DNA
<213> ORGANISM: Artificial sequence
<220> FEATURE:
<223> OTHER INFORMATION: Synthetic nucleic acid SAGE tag

```
<400> SEQUENCE: 41
actttaatac cacttag                                              17

<210> SEQ ID NO 42
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 42
cagaaaaata aatgtcc                                              17

<210> SEQ ID NO 43
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 43
tattgacaga agttaaa                                              17

<210> SEQ ID NO 44
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 44
cacaagctgt tagaggc                                              17

<210> SEQ ID NO 45
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 45
cttacaatga gaagcga                                              17

<210> SEQ ID NO 46
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 46
ggcgccacac aacgttg                                              17

<210> SEQ ID NO 47
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 47
tcctgccatt cacaaat                                              17

<210> SEQ ID NO 48
<211> LENGTH: 17
```

```
<212> TYPE: DNA
<213> ORGANISM: Artificial sequence
<220> FEATURE:
<223> OTHER INFORMATION: Synthetic nucleic acid SAGE tag

<400> SEQUENCE: 48
tgattggctt acctcag                                                  17

<210> SEQ ID NO 49
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 49
gaacaccacg acttccc                                                  17

<210> SEQ ID NO 50
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 50
cggaaactgc cagtgct                                                  17

<210> SEQ ID NO 51
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 51
cggaaactgc caaaaaa                                                  17

<210> SEQ ID NO 52
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 52
ggagcaggaa ccccttc                                                  17

<210> SEQ ID NO 53
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 53
tatgcagatg gcaccca                                                  17

<210> SEQ ID NO 54
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 54
gctcttaaga gagtttg                                                  17
```

<210> SEQ ID NO 55
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 55
cgggtttccc gcccgcc                                                17

<210> SEQ ID NO 56
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 56
caacgccagc ctctccc                                                17

<210> SEQ ID NO 57
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 57
tgtaacctga agaaata                                                17

<210> SEQ ID NO 58
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 58
cagatagctt agaccta                                                17

<210> SEQ ID NO 59
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 59
ggtgatttca acgccgg                                                17

<210> SEQ ID NO 60
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 60
gtgcttgctt gtgtgca                                                17

<210> SEQ ID NO 61
<211> LENGTH: 17
<212> TYPE: DNA
<213> ORGANISM: Artificial sequence
<220> FEATURE:
<223> OTHER INFORMATION: Synthetic nucleic acid SAGE tag

```
<400> SEQUENCE: 61
ccaaatctgt cctgttg                                                    17

<210> SEQ ID NO 62
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 62
caggcaaacc actcata                                                    17

<210> SEQ ID NO 63
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 63
atctcctaga tacctaa                                                    17

<210> SEQ ID NO 64
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 64
aaaggactgg ctggctg                                                    17

<210> SEQ ID NO 65
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 65
gggtgggtga aggcaga                                                    17

<210> SEQ ID NO 66
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 66
ttactttaat agtaaaa                                                    17

<210> SEQ ID NO 67
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 67
gtacagtgta gataatt                                                    17

<210> SEQ ID NO 68
<211> LENGTH: 17
```

```
<212> TYPE: DNA
<213> ORGANISM: Artificial sequence
<220> FEATURE:
<223> OTHER INFORMATION: Synthetic nucleic acid SAGE tag

<400> SEQUENCE: 68
tataggcttt ctaaaaa                                                17

<210> SEQ ID NO 69
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 69
agttcagagt gtagaca                                                17

<210> SEQ ID NO 70
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 70
tgtgtgggct gcctatg                                                17

<210> SEQ ID NO 71
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 71
attaccagaa ccacatt                                                17

<210> SEQ ID NO 72
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 72
cgaagggacc cacaacc                                                17

<210> SEQ ID NO 73
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 73
ggtcttacct caccacg                                                17

<210> SEQ ID NO 74
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 74
ttgcttggaa ccgcatt                                                17
```

<210> SEQ ID NO 75
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 75
caataaaaga tctggac                                                17

<210> SEQ ID NO 76
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 76
ctttagtgac cccagct                                                17

<210> SEQ ID NO 77
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 77
atggtgggca ctgctca                                                17

<210> SEQ ID NO 78
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 78
tcctctggaa tcattgg                                                17

<210> SEQ ID NO 79
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 79
agtcctgtgt gagcctt                                                17

<210> SEQ ID NO 80
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 80
atggtgggca ctgctca                                                17

<210> SEQ ID NO 81
<211> LENGTH: 17
<212> TYPE: DNA
<213> ORGANISM: Artificial sequence
<220> FEATURE:
<223> OTHER INFORMATION: Synthetic nucleic acid SAGE tag

```
<400> SEQUENCE: 81
tcctctggaa tcattgg                                                  17

<210> SEQ ID NO 82
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 82
cttcctgtct gagcact                                                  17

<210> SEQ ID NO 83
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 83
gggttgtaag gaatttt                                                  17

<210> SEQ ID NO 84
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 84
cctgcccctc ctccaca                                                  17

<210> SEQ ID NO 85
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 85
atagcagctg tcctagg                                                  17

<210> SEQ ID NO 86
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 86
taaaggatac tatattt                                                  17

<210> SEQ ID NO 87
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 87
agtcctgggt tctgtcc                                                  17

<210> SEQ ID NO 88
<211> LENGTH: 17
```

```
<212> TYPE: DNA
<213> ORGANISM: Artificial sequence
<220> FEATURE:
<223> OTHER INFORMATION: Synthetic nucleic acid SAGE tag

<400> SEQUENCE: 88
aaggctcgaa ataaaga                                                17

<210> SEQ ID NO 89
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 89
gatgaatctt tttcaag                                                17

<210> SEQ ID NO 90
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 90
gattctctgc atcaggc                                                17

<210> SEQ ID NO 91
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 91
ttggttaccc agctccg                                                17

<210> SEQ ID NO 92
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 92
gagtctcctg gcaaaga                                                17

<210> SEQ ID NO 93
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 93
aataaccagg cctcacg                                                17

<210> SEQ ID NO 94
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 94
acatctggtg acaaagg                                                17
```

```
<210> SEQ ID NO 95
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 95
ggtatctgct ggacagg                                                    17

<210> SEQ ID NO 96
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 96
ctgtcccctt gtctctc                                                    17

<210> SEQ ID NO 97
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 97
gagctgtctt atgtgtc                                                    17

<210> SEQ ID NO 98
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 98
tttccgagtc tctagag                                                    17

<210> SEQ ID NO 99
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 99
tttccgagtc tctagag                                                    17

<210> SEQ ID NO 100
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 100
agaagttgct cgtacct                                                    17

<210> SEQ ID NO 101
<211> LENGTH: 17
<212> TYPE: DNA
<213> ORGANISM: Artificial sequence
<220> FEATURE:
<223> OTHER INFORMATION: Synthetic nucleic acid SAGE tag
```

```
<400> SEQUENCE: 101
cccctgtggt atctgac                                                  17

<210> SEQ ID NO 102
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 102
gagttgtcac cgctgca                                                  17

<210> SEQ ID NO 103
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 103
ttacagagag caaagct                                                  17

<210> SEQ ID NO 104
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 104
taggttgctt aaagaaa                                                  17

<210> SEQ ID NO 105
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 105
accaaaaagc aagttgg                                                  17

<210> SEQ ID NO 106
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 106
ggcaattgtc ttctctg                                                  17

<210> SEQ ID NO 107
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 107
gcttaaacaa aatgcat                                                  17

<210> SEQ ID NO 108
<211> LENGTH: 17
```

```
<212> TYPE: DNA
<213> ORGANISM: Artificial sequence
<220> FEATURE:
<223> OTHER INFORMATION: Synthetic nucleic acid SAGE tag

<400> SEQUENCE: 108
cctaagtatg gtacagg                                                    17

<210> SEQ ID NO 109
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 109
gttagtcaga aactgcc                                                    17

<210> SEQ ID NO 110
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 110
tacagtataa gacaata                                                    17

<210> SEQ ID NO 111
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 111
aacgtaaaat acttaag                                                    17

<210> SEQ ID NO 112
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 112
ggtctttgag ggagcag                                                    17

<210> SEQ ID NO 113
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 113
tcccctgccc agttcac                                                    17

<210> SEQ ID NO 114
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 114
ctttgaggcc agcagag                                                    17
```

<210> SEQ ID NO 115
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 115
cgctgtattc ttcacag                                                      17

<210> SEQ ID NO 116
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 116
gagtgcttcc gagaagc                                                      17

<210> SEQ ID NO 117
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 117
gtcattctcc gagccag                                                      17

<210> SEQ ID NO 118
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 118
gtgttgctgt cactagg                                                      17

<210> SEQ ID NO 119
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 119
agtactcaat ccagttt                                                      17

<210> SEQ ID NO 120
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 120
taaattggat gcaatgt                                                      17

<210> SEQ ID NO 121
<211> LENGTH: 17
<212> TYPE: DNA
<213> ORGANISM: Artificial sequence
<220> FEATURE:
<223> OTHER INFORMATION: Synthetic nucleic acid SAGE tag

```
<400> SEQUENCE: 121
gatattttgc ctgtcaa                                                      17

<210> SEQ ID NO 122
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 122
atgacgacct tgttggc                                                      17

<210> SEQ ID NO 123
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 123
gagtcagcaa ctttgca                                                      17

<210> SEQ ID NO 124
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 124
aagtaattct ggtaaca                                                      17

<210> SEQ ID NO 125
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 125
atgccgagat tgtacgg                                                      17

<210> SEQ ID NO 126
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 126
aggaagatca ccaggga                                                      17

<210> SEQ ID NO 127
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 127
ctaatggccc attagtg                                                      17

<210> SEQ ID NO 128
<211> LENGTH: 17
```

```
<212> TYPE: DNA
<213> ORGANISM: Artificial sequence
<220> FEATURE:
<223> OTHER INFORMATION: Synthetic nucleic acid SAGE tag

<400> SEQUENCE: 128
aaggaagaaa gctctgc                                                    17

<210> SEQ ID NO 129
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 129
cttgaggtct agaggaa                                                    17

<210> SEQ ID NO 130
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 130 agagaattt ccatact                                                     17

<210> SEQ ID NO 131
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 131
atttccatct tcatacc                                                    17

<210> SEQ ID NO 132
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 132
ctaggcaaga acattac                                                    17

<210> SEQ ID NO 133
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 133
accggaagga atttgct                                                    17

<210> SEQ ID NO 134
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 134
atgcccggca ggtgctc                                                    17
```

<210> SEQ ID NO 135
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 135
gactacccat ctctggg                                                17

<210> SEQ ID NO 136
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 136
gtttgctctg ctggcat                                                17

<210> SEQ ID NO 137
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 137
gctctgtgtc tatgcag                                                17

<210> SEQ ID NO 138
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 138
gctctcttgt gtgcact                                                17

<210> SEQ ID NO 139
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 139
gctggcactg gtaacct                                                17

<210> SEQ ID NO 140
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 140
ggggaaggct ggtggtc                                                17

<210> SEQ ID NO 141
<211> LENGTH: 17
<212> TYPE: DNA
<213> ORGANISM: Artificial sequence
<220> FEATURE:
<223> OTHER INFORMATION: Synthetic nucleic acid SAGE tag

```
<400> SEQUENCE: 141
cagagggctg gggccgg                                                  17

<210> SEQ ID NO 142
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 142
agactgtaaa ctgggtg                                                  17

<210> SEQ ID NO 143
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 143
ggactctgta aactggg                                                  17

<210> SEQ ID NO 144
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 144
ggactctggc cagcacc                                                  17

<210> SEQ ID NO 145
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 145
gtgctattct ggagctg                                                  17

<210> SEQ ID NO 146
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 146
tgggcggcag ctggggg                                                  17

<210> SEQ ID NO 147
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 147
caatgtggga agtggag                                                  17

<210> SEQ ID NO 148
<211> LENGTH: 17
```

-continued

```
<212> TYPE: DNA
<213> ORGANISM: Artificial sequence
<220> FEATURE:
<223> OTHER INFORMATION: Synthetic nucleic acid SAGE tag

<400> SEQUENCE: 148
gggggttggg agagggg                                                  17

<210> SEQ ID NO 149
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 149
tgggaggcag ctggggg                                                  17

<210> SEQ ID NO 150
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 150
actcctggac agctcaa                                                  17

<210> SEQ ID NO 151
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 151
catcatattt gcacaca                                                  17

<210> SEQ ID NO 152
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 152
ggaaacaact gttacaa                                                  17

<210> SEQ ID NO 153
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 153
gtggactgga aggccgc                                                  17

<210> SEQ ID NO 154
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 154
ggtctccccc ttcagac                                                  17
```

<210> SEQ ID NO 155
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 155
agaaaccttg ataaaac                                                17

<210> SEQ ID NO 156
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 156
gctgactaca acatcaa                                                17

<210> SEQ ID NO 157
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 157
aagtattcca cagtaca                                                17

<210> SEQ ID NO 158
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 158
aagcagggcg gaacctt                                                17

<210> SEQ ID NO 159
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 159
tgtgttctta ggcatct                                                17

<210> SEQ ID NO 160
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 160
gtcatctaaa aggacta                                                17

<210> SEQ ID NO 161
<211> LENGTH: 17
<212> TYPE: DNA
<213> ORGANISM: Artificial sequence
<220> FEATURE:
<223> OTHER INFORMATION: Synthetic nucleic acid SAGE tag

```
<400> SEQUENCE: 161
tgattttgac tgcaaat                                              17

<210> SEQ ID NO 162
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 162
gttctatact cttctgg                                              17

<210> SEQ ID NO 163
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 163
taaatatgtc tttataa                                              17

<210> SEQ ID NO 164
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 164
ttcttctcag aggcctc                                              17

<210> SEQ ID NO 165
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 165
tagaggggac ccagtct                                              17

<210> SEQ ID NO 166
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 166
ccttcaatgc agccggg                                              17

<210> SEQ ID NO 167
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 167
gcctttcaag ggggcag                                              17

<210> SEQ ID NO 168
<211> LENGTH: 17
```

```
<212> TYPE: DNA
<213> ORGANISM: Artificial sequence
<220> FEATURE:
<223> OTHER INFORMATION: Synthetic nucleic acid SAGE tag

<400> SEQUENCE: 168
ggaagcagac agcaggc                                                    17

<210> SEQ ID NO 169
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 169 ggcccctcc ggccca                                                      17

<210> SEQ ID NO 170
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 170
tgatctccca ggagatg                                                    17

<210> SEQ ID NO 171
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 171
gcgacagtct cactctg                                                    17

<210> SEQ ID NO 172
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 172
tctctatatc tccttct                                                    17

<210> SEQ ID NO 173
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 173
ttacctcagt ccagaca                                                    17

<210> SEQ ID NO 174
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 174
actagaaaat taaacag                                                    17
```

<210> SEQ ID NO 175
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 175 taaaaaaag agaaaaa                                                    17

<210> SEQ ID NO 176
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 176
tacaaataaa aactaaa                                                   17

<210> SEQ ID NO 177
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 177
atgtacacat acgacga                                                   17

<210> SEQ ID NO 178
<211> LENGTH: 17
<212> TYPE: DNA
<213> ORGANISM: Artificial sequence
<220> FEATURE:
<223> OTHER INFORMATION: Synthetic nucleic acid SAGE tag

<400> SEQUENCE: 178
ggatacaata aatatcc                                                   17

<210> SEQ ID NO 179
<211> LENGTH: 21
<212> TYPE: DNA
<213> ORGANISM: Artificial sequence
<220> FEATURE:
<223> OTHER INFORMATION: Synthetic nucleic acid PCR primer

<400> SEQUENCE: 179
ctcctcctcc aacaagagca g                                              21

<210> SEQ ID NO 180
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 180
cgatgaaggc ataaccacg                                                 19

<210> SEQ ID NO 181
<211> LENGTH: 18
<212> TYPE: DNA
<213> ORGANISM: Artificial sequence
<220> FEATURE:
<223> OTHER INFORMATION: Synthetic nucleic acid PCR primer

```
<400> SEQUENCE: 181
gctacctgcc caccatcg                                                18

<210> SEQ ID NO 182
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 182
catccactgc tgtcacacgg                                              20

<210> SEQ ID NO 183
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 183
atcccagcag caagaaggtg                                              20

<210> SEQ ID NO 184
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 184
atcatcagca tggagttccg                                              20

<210> SEQ ID NO 185
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 185
tggaactgga accaacatgg                                              20

<210> SEQ ID NO 186
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 186
aggtatggct cccagcgag                                               19

<210> SEQ ID NO 187
<211> LENGTH: 18
<212> TYPE: DNA
<213> ORGANISM: Artificial sequence
<220> FEATURE:
<223> OTHER INFORMATION: Synthetic nucleic acid PCR primer

<400> SEQUENCE: 187
gtgggcaagc ggctacag                                                18

<210> SEQ ID NO 188
<211> LENGTH: 20
```

```
<212> TYPE: DNA
<213> ORGANISM: Artificial sequence
<220> FEATURE:
<223> OTHER INFORMATION: Synthetic nucleic acid PCR primer

<400> SEQUENCE: 188
cgatgttggg ttctcctagc                                              20

<210> SEQ ID NO 189
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 189
atcgagacga gagaatgggc                                              20

<210> SEQ ID NO 190
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 190
ggagtccgtg tgatctgtgg                                              20

<210> SEQ ID NO 191
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 191
actgctccgc ccagatacc                                               19

<210> SEQ ID NO 192
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 192
ccatagccat ttcgaccacc                                              20

<210> SEQ ID NO 193
<211> LENGTH: 22
<212> TYPE: DNA
<213> ORGANISM: Artificial sequence
<220> FEATURE:
<223> OTHER INFORMATION: Synthetic nucleic acid PCR primer

<400> SEQUENCE: 193
ctcagcctat tgaagagatg cg                                           22

<210> SEQ ID NO 194
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 194
agcgtctcac tggtgtcagg                                              20
```

<210> SEQ ID NO 195
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 195
gcgtctccga gatcatcagc                                          20

<210> SEQ ID NO 196
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 196
tgacccgtac cttcctcctg                                          20

<210> SEQ ID NO 197
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 197
atcgcccagt acaagtgcc                                           19

<210> SEQ ID NO 198
<211> LENGTH: 18
<212> TYPE: DNA
<213> ORGANISM: Artificial sequence
<220> FEATURE:
<223> OTHER INFORMATION: Synthetic nucleic acid PCR primer

<400> SEQUENCE: 198
ggaaggtccc atccagcg                                            18

<210> SEQ ID NO 199
<211> LENGTH: 21
<212> TYPE: DNA
<213> ORGANISM: Artificial sequence
<220> FEATURE:
<223> OTHER INFORMATION: Synthetic nucleic acid PCR primer

<400> SEQUENCE: 199
tttggcttgg actggataac c                                        21

<210> SEQ ID NO 200
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 200
tgcccatcag gttgacacg                                           19

<210> SEQ ID NO 201
<211> LENGTH: 21
<212> TYPE: DNA
<213> ORGANISM: Artificial sequence
<220> FEATURE:
<223> OTHER INFORMATION: Synthetic nucleic acid PCR primer

<400> SEQUENCE: 201
gaagatgtga gagccctgga g                                          21

<210> SEQ ID NO 202
<211> LENGTH: 22
<212> TYPE: DNA
<213> ORGANISM: Artificial sequence
<220> FEATURE:
<223> OTHER INFORMATION: Synthetic nucleic acid PCR primer

<400> SEQUENCE: 202
cctggattat ctcccagtgt tg                                         22

<210> SEQ ID NO 203
<211> LENGTH: 22
<212> TYPE: DNA
<213> ORGANISM: Artificial sequence
<220> FEATURE:
<223> OTHER INFORMATION: Synthetic nucleic acid PCR primer

<400> SEQUENCE: 203
ctacacccaa cagtagcatt cg                                         22

<210> SEQ ID NO 204
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 204
tccgtcagtc cagtccagg                                             19

<210> SEQ ID NO 205
<211> LENGTH: 18
<212> TYPE: DNA
<213> ORGANISM: Artificial sequence
<220> FEATURE:
<223> OTHER INFORMATION: Synthetic nucleic acid PCR primer

<400> SEQUENCE: 205
cgcacacttc ccgctgag                                              18

<210> SEQ ID NO 206
<211> LENGTH: 18
<212> TYPE: DNA
<213> ORGANISM: Artificial sequence
<220> FEATURE:
<223> OTHER INFORMATION: Synthetic nucleic acid PCR primer

<400> SEQUENCE: 206
gctcgccttg atggttcc                                              18

<210> SEQ ID NO 207
<211> LENGTH: 18
<212> TYPE: DNA
<213> ORGANISM: Artificial sequence
<220> FEATURE:
<223> OTHER INFORMATION: Synthetic nucleic acid PCR primer

<400> SEQUENCE: 207
cgggatgaca tcgagcag                                              18

<210> SEQ ID NO 208
<211> LENGTH: 21

```
<212> TYPE: DNA
<213> ORGANISM: Artificial sequence
<220> FEATURE:
<223> OTHER INFORMATION: Synthetic nucleic acid PCR primer

<400> SEQUENCE: 208
acactcaggc tcttccacca c                                           21

<210> SEQ ID NO 209
<211> LENGTH: 18
<212> TYPE: DNA
<213> ORGANISM: Artificial sequence
<220> FEATURE:
<223> OTHER INFORMATION: Synthetic nucleic acid PCR primer

<400> SEQUENCE: 209
ccgtcatatt cgcctggg                                               18

<210> SEQ ID NO 210
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 210
tgctggcagg tgctctagg                                              19

<210> SEQ ID NO 211
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 211
cttgttcgat gttcacagcg                                             20

<210> SEQ ID NO 212
<211> LENGTH: 21
<212> TYPE: DNA
<213> ORGANISM: Artificial sequence
<220> FEATURE:
<223> OTHER INFORMATION: Synthetic nucleic acid PCR primer

<400> SEQUENCE: 212
gccgtagagc tgtcttggat c                                           21

<210> SEQ ID NO 213
<211> LENGTH: 22
<212> TYPE: DNA
<213> ORGANISM: Artificial sequence
<220> FEATURE:
<223> OTHER INFORMATION: Synthetic nucleic acid PCR primer

<400> SEQUENCE: 213
aacgaagtct ccaaatctgt cc                                          22

<210> SEQ ID NO 214
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 214
aggtggaatt aggcctggg                                              19
```

<210> SEQ ID NO 215
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 215
cagcataggt ggacagccg                                          19

<210> SEQ ID NO 216
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 216
cacaccacgt ccttctccg                                          19

<210> SEQ ID NO 217
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 217
ggagacagat cgtagaggcg                                         20

<210> SEQ ID NO 218
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 218
ggaagcagcc agagtcgtg                                          19

<210> SEQ ID NO 219
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 219
gtccgcacct gtgttgtcc                                          19

<210> SEQ ID NO 220
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 220
catcttccag cttctttccg                                         20

<210> SEQ ID NO 221
<211> LENGTH: 22
<212> TYPE: DNA
<213> ORGANISM: Artificial sequence
<220> FEATURE:
<223> OTHER INFORMATION: Synthetic nucleic acid PCR primer

```
<400> SEQUENCE: 221
tagcagagaa ccgagattca cc                                             22

<210> SEQ ID NO 222
<211> LENGTH: 21
<212> TYPE: DNA
<213> ORGANISM: Artificial sequence
<220> FEATURE:
<223> OTHER INFORMATION: Synthetic nucleic acid PCR primer

<400> SEQUENCE: 222
gcttcagagc agccttcgta g                                              21

<210> SEQ ID NO 223
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 223
aatctgaggc tctgcgtgc                                                 19

<210> SEQ ID NO 224
<211> LENGTH: 21
<212> TYPE: DNA
<213> ORGANISM: Artificial sequence
<220> FEATURE:
<223> OTHER INFORMATION: Synthetic nucleic acid PCR primer

<400> SEQUENCE: 224
gcccttcaat cctgctttag a                                              21

<210> SEQ ID NO 225
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 225
gtgccttgaa ggaccttgg                                                 19

<210> SEQ ID NO 226
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 226
agcagccact acagcgactc                                                20

<210> SEQ ID NO 227
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 227
ggtgtcggag cacatctgg                                                 19

<210> SEQ ID NO 228
<211> LENGTH: 21
```

<212> TYPE: DNA
<213> ORGANISM: Artificial sequence
<220> FEATURE:
<223> OTHER INFORMATION: Synthetic nucleic acid PCR primer

<400> SEQUENCE: 228
tcaaactggt ccttagaacg g                                      21

<210> SEQ ID NO 229
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 229
cggcactacc tctgagcagt                                        20

<210> SEQ ID NO 230
<211> LENGTH: 21
<212> TYPE: DNA
<213> ORGANISM: Artificial sequence
<220> FEATURE:
<223> OTHER INFORMATION: Synthetic nucleic acid PCR primer

<400> SEQUENCE: 230
aacctgaatg gaccagtcac c                                      21

<210> SEQ ID NO 231
<211> LENGTH: 21
<212> TYPE: DNA
<213> ORGANISM: Artificial sequence
<220> FEATURE:
<223> OTHER INFORMATION: Synthetic nucleic acid PCR primer

<400> SEQUENCE: 231
tcactggatg gctgatgaca c                                      21

<210> SEQ ID NO 232
<211> LENGTH: 19
<212> TYPE: DNA
<213> ORGANISM: Artificial sequence
<220> FEATURE:
<223> OTHER INFORMATION: Synthetic nucleic acid PCR primer

<400> SEQUENCE: 232
tgttggaggc atgtcggtc                                         19

<210> SEQ ID NO 233
<211> LENGTH: 20
<212> TYPE: DNA
<213> ORGANISM: Artificial sequence
<220> FEATURE:
<223> OTHER INFORMATION: Synthetic nucleic acid PCR primer

<400> SEQUENCE: 233
ttccacagta ccagcccttg                                        20

<210> SEQ ID NO 234
<211> LENGTH: 19
<212> TYPE: DNA
<213> ORGANISM: Artificial sequence

```
-continued

<220> FEATURE:
<223> OTHER INFORMATION: Synthetic nucleic acid PCR primer

<400> SEQUENCE: 234
ctccacgggg accttgttc                                                    19
```

DIFFERENTIAL GENE EXPRESSION IN PHYSIOLOGICAL AND PATHOLOGICAL ANGIOGENESIS

CROSS REFERENCE TO RELATED APPLICATIONS

This is a continuation application of U.S. application Ser. No. 12/514,297, filed May 8, 2009, now abandoned, which is the U.S. National Stage of International Application No. PCT/US2007/072395, filed Jun. 28, 2007, which was published in English under PCT Article 21(2), which in turn claims the benefit of U.S. Provisional Application No. 60/858,068, filed on Nov. 9, 2006 and U.S. Provisional Application No. 60/879,457, filed on Jan. 8, 2007. The entire disclosures of the prior applications are considered to be part of the disclosure of the accompanying application and are hereby incorporated by reference.

FIELD

The present disclosure relates to the field of angiogenesis and endothelial cell markers and in particular, to pathological angiogenesis endothelial markers and organ-specific endothelial markers and methods of their uses.

BACKGROUND

Inhibition of tumor angiogenesis is an anticancer strategy that has gained widespread support from biologists and clinicians. In 1971, Dr. Judah Folkman introduced the concept of an "angiogenic switch" driving tumor growth and malignant progression. There have since been numerous scientific reports confirming the central concept that tumor growth is angiogenesis-dependent. Angiogenesis can occur under "normal" physiological conditions, such as during growth and development or wound healing, as well as under "pathological" conditions, such as in the transition of tumors from a dormant state to a malignant state. The dependency of solid tumors on new vessel growth has made tumor vessels an appealing target for cancer therapy.

Angiogenesis-based tumor therapy has several theoretical advantages over traditional cancer therapies (such as radiation and chemotherapy). Anti-angiogenesis therapy targets endothelial cells that line tumor vessels instead of the tumor cells themselves. Tumor cells evolve resistance to cancer therapies due to genomic instability (high variation) and rapid generation time (days). In contrast, endothelial cells have a higher genomic stability (low variation) and a longer generation time (months) compared to tumor cells. Endothelial cells are less likely to "escape" therapy because they will not undergo mitosis at such a rapid rate and carry any drug resistance variation through to the next generation within the lifespan of the therapy. Thus, the genomic stability of endothelial cells coupled with their longevity make them an attractive target for therapies directed against them.

Tumor endothelial markers (TEMs) were reported by St. Croix et al. (*Science*, 289: 1197-1201, 2000). St. Croix et al. employed serial analysis of gene expression (SAGE™) technology to compare small populations of normal and tumor-derived endothelial cells. The comparison revealed 79 genes that are potentially involved in angiogenesis. Of these, 46 genes were specifically expressed at least ten times higher in tumor-associated endothelium as compared to normal endothelium from the same patient.

The use of targeted drug delivery to inhibit tumor growth by interfering with angiogenesis has recently proven to be successful. For example, bevacizumab (Avastin®), an antibody that neutralizes vascular endothelial growth factor (VEGF; one of the many proteins involved in the development of a new network of blood vessels), has been approved by the FDA to treat colorectal cancer. A remaining challenge, however, is to identify markers that can differentiate pathological and physiological angiogenesis in order to selectively deliver therapeutic agents to diseased tissues while minimizing the potential side effects of the targeted therapy.

SUMMARY

Disclosed herein are angiogenesis-specific endothelial markers, including some specific for pathological angiogenesis. Endothelial cells were isolated from normal, regenerating, and tumor-bearing livers. Gene expression profiles amongst the multiple samples were compared by performing serial analysis of gene expression (SAGE) on the isolated endothelial cells. The identification of markers highly specific for physiological or pathological angiogenesis has significant implications for the development of selective vascular targeted therapies. Thus, methods of reducing or inhibiting pathological angiogenesis in a subject are disclosed.

In one example, the method includes administering a therapeutically effective amount of a composition that includes one or more binding agents (such as an antibody) that specifically binds to one or more of the following pathological angiogenesis marker proteins: Vscp, CD276, ETSvg4 (Pea3), CD137(4-1BB), MiRP2, Ubiquitin D (Fat10), Doppel (prion-PLP), Apelin, Plgf, Ptprn (IA-2), CD109, Ankylosis, and collagen VIIIα1, thereby inhibiting pathological angiogenesis in the subject. In a further example, the binding agent is conjugated to one or more therapeutic molecules, such as chemotherapy agents, cytoxins, radionucleotides or a combination thereof.

Methods are disclosed for screening for pathological angiogenesis in a subject. In particular examples, the method includes detecting at least one expression product including one or more of: Vscp, CD276, ETSvg4 (Pea3), CD137(4-1BB), MiRP2, Ubiquitin D (Fat10), Doppel (prion-PLP), Apelin, Plgf, Ptprn (IA-2), CD109, Ankylosis, and collagen VIII, 1 in a sample obtained from the subject. Detection of the at least one expression product can indicate the presence of pathological angiogenesis in the subject.

In addition, disclosed herein are 27 brain-specific endothelial markers and 15 liver-specific endothelial markers. These organ-specific endothelial markers can serve as therapeutic targets to allow molecular agents to be selectively delivered to specific anatomical sites. Similarly, these organ-specific endothelial markers can serve as diagnostic targets to allow diagnostic agents (such as imaging agents) to be selectively delivered to specific anatomical sites. Thus, methods of delivering a therapeutic agent to organ-specific endothelial cells are provided.

Methods are disclosed for delivering a therapeutic or diagnostic agent to brain endothelial cells. In particular examples, the method includes administering a therapeutically effective amount of a composition that includes a therapeutic binding agent that preferentially binds to one or more brain endothelial marker proteins. Such a method can evoke a therapeutic response in the brain endothelial cells or permit detection of the cells. In certain cases brain endothelial markers may also facilitate the selectively delivery of therapeutic agents across the blood-brain barrier to underlying neuronal cells via transcytosis. The one or more brain endothelial markers can include Glucose transporter GLUT-1, Organic anion transporter 2, Pleiotrophin, ATPase class V, type 10A, Peptidoglycan recognition protein 1, Organic anion transporter 14, Forkhead box Q1, Organic anion transporter 3, SN2 (Solute carrier family 38, member 5), Inter-alpha (globulin) inhibitor H5, Solute carrier 38 member 3, Zinc finger protein of the cerebellum 2, Testican-2,3-HMG-CoA synthase 2, Progestin and adipoQ receptor family member V, APC down-regulated 1 Drapc1, GDPD phosphodiesterase family Accession No. NM_001042671, putative transmembrane protein Accession No. NM_029001, DES2 lipid desaturase/C4-hyroxylase, Kelch repeat and BTB (POZ) domain, Lipolysis stimulated receptor, Glutathione S-transferase alpha 4, TNF receptor superfamily member 19, T-box 1, putative secreted protein Accession No. XM_620023 or combinations thereof.

Methods are disclosed for delivering a therapeutic or diagnostic agent to liver endothelial cells. In particular examples, the method includes administering a therapeutically effective amount of a composition that includes a binding agent that specifically binds to one or more liver endothelial marker proteins (e.g., deoxyribonuclease 1-like 3, LZP oncoprotein induced transcript 3, putative transmembrane protein Accession No. NM_023438, CD32 15, putative G-protein coupled receptor NM_033616, C-type lectin-like receptor 2, C-type lectin domain family 4 member g 16, Plexin C1, Wnt9B, Accession No. AK144596, GATA-binding protein 4, MBL-associated serine protease-3, Renin binding protein, putative transmembrane protein Accession No. NM_144830, or Retinoic acid receptor, beta) and a therapeutic agent. Such a method can evoke a therapeutic response in the liver endothelial cells or permit detection of the cells.

The foregoing and other features of the disclosure will become more apparent from the following detailed description, which proceeds with reference to the accompanying figures.

RT-PCR was used to verify that Ubiquitin D is expressed by the tumor endothelial cells (TECs) and not the tumor cells themselves.

Figure 8:
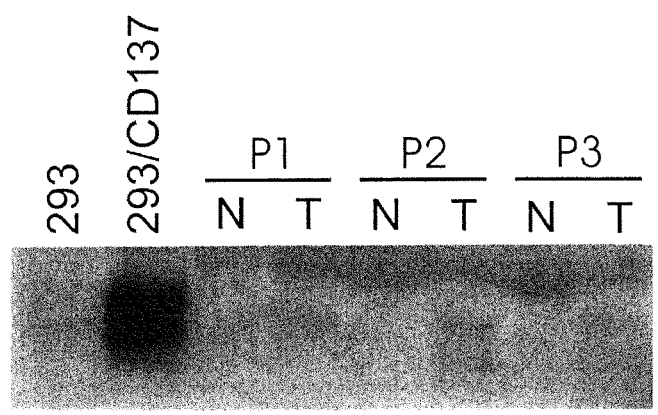

FIG. 8 is a digital image of an immunoblot including protein extracts from three subjects with either normal colonic mucosa (N) or colorectal tumors (T). CD137 expression was elevated in protein extracts of human colorectal cancer.

Figure 9A:
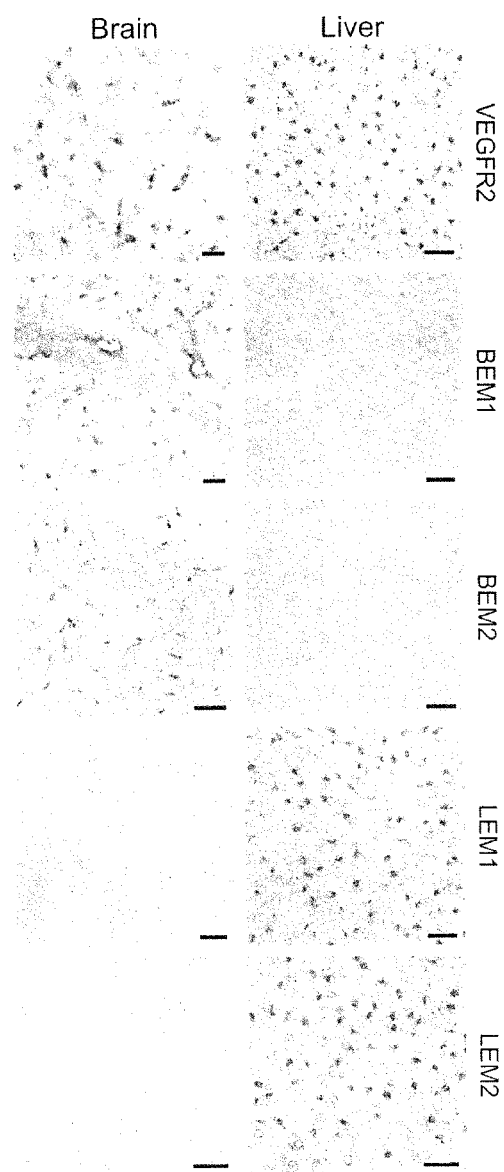

FIG. 9A includes digital images of LEM and BEM genes identified by SAGE are expressed by ECs in vivo. Localization of mRNA in ECs was demonstrated for the brain endothelial markers GLUT-1 (BEM1) and organic anion transporter 2 (BEM2), and the liver endothelial markers deoxyribonuclease 1-like 3 (LEM1) and oncogenes induced transcript 3 (LEM2). The BEMs are selectively expressed in brain endothelium whereas the LEMs are selectively expressed in liver endothelium. The endothelial control probe, VEGFR2, stains both brain and liver endothelium. Staining of LEMs is most prominent in the sinusoidal endothelium, wherein the nuclear body appears to stain most intensely. A dilute counterstain was applied to the sections to highlight the lack of detectable expression in the non-ECs of the tissues. Scale bars, 50 μM FIG. 9B includes digital images of localization of Apelin and Doppel mRNA in subcutaneous implanted LLC tumors.

DETAILED DESCRIPTION

I. Introduction

Angiogenesis is critical for the progression of many diseases, including age-related macular degeneration and cancer. Markers that can distinguish physiological and pathological angiogenesis are needed in order to selectively deliver anti-angiogenic or vascular targeting agents to diseased tissues and minimize the potential side effects of the targeted therapy. Physiological and pathological angiogenesis are morphologically distinct. However, the extent of differential gene expression between these cellular states has remained elusive. Most of the well-studied molecules thought to regulate tumor angiogenesis, such as vascular endothelial growth factor (VEGF), basic fibroblast growth factor (bFGF), the angiopoietins, and their receptors, also regulate normal physiological angiogenesis.

The inventors have identified twenty-five angiogenesis-specific endothelial markers, including thirteen that are specific for pathological angiogenesis. The genes specific for pathological angiogenesis were primarily cell surface molecules. Therefore, this disclosure provides several molecules that can be used for the therapeutic targeting of tumor vessels. For example, a binding agent specific to one or more of the disclosed pathological angiogenesis endothelial marker proteins can be used for targeted drug delivery to the tumor site. Further, linking or conjugating the binding agent to a chemical or radioactive toxin can provide a targeted cytotoxic therapy. In another or additional example, a binding agent specific to one or more of the disclosed pathological angiogenesis endothelial marker proteins is labeled with an imaging tag, such as a fluorophore, thereby providing diagnostic imaging agents.

Therefore, methods of reducing or inhibiting pathological angiogenesis are provided, in some examples a therapeutically effective amount of a binding agent that specifically binds to at least one of the disclosed pathological angiogenesis endothelial marker proteins is administered to a subject. As a result, pathological angiogenesis in the subject is thereby reduced or inhibited. Additional methods of diagnosing or treating a tumor are also provided.

The present disclosure also provides twenty-seven brain-specific endothelial markers and fifteen liver-specific endothelial markers. These organ-specific endothelial markers can aid in the selective delivery of therapeutic and diagnostic agents to specific anatomical sites. For example, methods are disclosed for delivering a therapeutic or diagnostic agent to brain endothelial cells. In particular examples, the method includes administering a therapeutically effective amount of a binding agent, such as an antibody, that specifically binds to at least one of the disclosed brain endothelial markers, thereby evoking a therapeutic response in the brain endothelial cells or permitting imaging of the brain endothelial cells. In another example, the binding agent, upon binding at least one of the disclosed brain endothelial markers, would enable the delivery of the agent, via mechanisms such as transcytosis, across the blood-brain barrier to the particular cells underlying the brain endothelium, such as neuronal cells.

In a further example, the method includes delivering a therapeutic agent to liver endothelial cells by administering a therapeutically effective amount of a binding agent that specifically binds to at least one of the disclosed liver endothelial marker proteins, thereby evoking a therapeutic response in the liver endothelial cells or permitting imaging of the liver endothelial cells.

II. Terms and Abbreviations

Abbreviations

BEMs brain endothelial markers
cDNA: complementary DNA
ECs: endothelial cells
LEMs liver endothelial markers
μg: microgram
μl: microliter
M: molar
QPCR: quantitative PCR
PCR: polymerase chain reaction
SAGE: serial analysis of gene expression The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. For example, reference to "an endothelial marker" includes a plurality of such markers and reference to "the antibody" includes reference to one or more antibodies and equivalents thereof known to those skilled in the art, and so forth. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs.

Administration: To provide or give a subject an agent, such as a composition that includes a binding agent that specifically binds to one or more of the disclosed pathological angiogenesis endothelial marker proteins (such as those listed in Tables 8 and 9) by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

Agent: Any protein, nucleic acid molecule, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In a particular example, a pharmaceutical agent (such as an antibody to any of the proteins listed in Tables 8 and 9 conjugated to a therapeutic agent) significantly reduces angiogenesis.

Angiogenesis: A physiological process involving the growth of new blood vessels from pre-existing vessels.

Angiogenesis can occur under normal physiological conditions such as during growth and development or wound healing (known as physiological angiogenesis) as well as pathological conditions such as in the transition of tumors from a dormant state to a malignant state (known as pathological angiogenesis).

Ankylosis: The ANK protein, the product of the progressive ankylosis (ank) gene, is a multipass transmembrane protein that is highly conserved in vertebrates. The ANK protein has been shown to control pyrophosphate levels in cells and may act as a pyrophosphate transporter that stimulates the elaboration of extracellular pyrophosphate from intracellular stores. The term ankylosis includes any ankylosis gene, cDNA, mRNA, or protein from any organism and that is ankylosis and is increased during pathological angiogenesis relative to either normal or physiological angiogenesis conditions. In one example, ANK protein is expressed during pathological angiogenesis.

Exemplary nucleic acid and protein sequences for ankylosis are publicly available. For example, GenBank Accession Nos.: DQ832285, NM_020332, AK083135, BC054379, AY358503, and NM_054027 disclose ankylosis nucleic acid sequences and GenBank Accession Nos.: AAF88038, Q9JHZ2, XP_001132013, NP_473368, and Q9HCJ1 disclose ankylosis protein sequences.

In one example, ankylosis includes a full-length wild-type (or native) sequence, as well as ankylosis allelic variants, fragments, homologs or fusion sequences that retain the ability to be preferentially expressed during pathological angiogenesis and/or modulate pathological angiogenesis. In certain examples, ankylosis has at least 80% sequence identity, for example at least 85%, 90%, 95%, or 98% sequence identity to ankylosis. In other examples, ankylosis has a sequence that hybridizes under very high stringency conditions to a sequence set forth in GenBank Accession No. DQ832285, NM_020332, AK083135, BC054379, AY358503, or NM_054027 and retains ankylosis activity (e.g., the capability to be expressed during pathological angiogenesis and/or modulate pathological angiogenesis).

Antibody: A polypeptide ligand including at least a light chain or heavy chain immunoglobulin variable region which specifically recognizes and binds an epitope of an antigen, such as an endothelial marker or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. In one example, an antibody specifically binds to one of the proteins listed in Tables 8 and 9.

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognising a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen which are then purified from the mammal's serum.

A "chimeric antibody" has framework residues from one species, such as human, and CDRs (which generally confer antigen binding) from another species, such as a murine antibody that specifically binds an endothelial marker.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they are substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585,089).

Binding affinity: Affinity of one molecule for another, such as an antibody for an antigen (for example, the antigens shown in Tables 8 and 9). In one example, affinity is calculated by a modification of the Scatchard method described by Frankel et al., *Mol. Immunol.*, 16:101-106, 1979. In another example, binding affinity is measured by an antigen/antibody dissociation rate. In yet another example, a high binding affinity is measured by a competition radioimmunoassay. In several examples, a high binding affinity is at least about $1 \times 10^{-8}$ M. In other examples, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Biological activity: An expression describing the beneficial or adverse effects of an agent on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, a specific binding agent significantly reduces the biological activity of the one or more pathological angiogenesis marker proteins (such as those listed in Table 9) which in turn inhibits pathological angiogenesis.

Cancer: Malignant neoplasm that has undergone characteristic anaplasia with loss of differentiation, increase rate of growth, invasion of surrounding tissue, and is capable of metastasis.

CD276: A member of the B7 family of immunoregulatory molecules that can be induced on T-cells, macrophages and dendritic cells by a variety of inflammatory cytokines. Its homology to other co-stimulatory molecules indicates it may have an immunoregulatory role. In particular examples, expression of CD276 is increased during pathological angiogenesis. The term CD276 includes any CD276 gene, cDNA, mRNA, or protein from any organism and that is CD276 and is expressed during pathological angiogenesis.

Nucleic acid and protein sequences for CD276 are publicly available. For example, GenBank Accession Nos.: DQ832276, NM_001024736, AK031354, AK155114, NM_133983, and NM_025240 disclose CD276 nucleic acid sequences, and GenBank Accession Nos.: NP_598744, NP_079516, and AAK15438 disclose CD276 protein sequences.

In one example, CD276 includes a full-length wild-type (or native) sequence, as well as CD276 allelic variants, fragments, homologs or fusion sequences that retain the ability to be expressed during pathological angiogenesis and/or modulate pathological angiogenesis. In certain examples, CD276 has at least 80% sequence identity, for example at least 85%, 90%, 95%, or 98% sequence identity to CD276. In other examples, CD276 has a sequence that hybridizes under very high stringency conditions to a sequence set forth in GenBank Accession No. DQ832276, NM_001024736, NP_598744, NP_079516 and AAK15438, or NM_025240 and retains CD276 activity (such as the capability to be expressed during pathological angiogenesis and/or modulate pathological angiogenesis).

Chemotherapy: In cancer treatment, chemotherapy refers to the administration of one or a combination of compounds to kill or slow the reproduction of rapidly multiplying cells. Chemotheraputic agents include but are not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol and taxotere. Such agents can be co-administered with the disclosed endothelial marker molecules to a subject. For example, to treat a tumor, chemotherapeutic agents can also be administered prior to or subsequent to administration of the disclosed modified endothelial marker molecules to a subject or can be conjugated to the disclosed endothelial markers (e.g., Tables 8 and 9). In one example, chemotherapeutic agents are co-administered with radiation therapy, along with the disclosed endothelial molecules for treatment of a tumor.

Chimeric antibody: An antibody which includes sequences derived from two different antibodies, which typically are of different species. Most typically, chimeric antibodies include human and murine antibody domains, generally human constant regions and murine variable regions, murine CDRs and/or murine SDRs. For example, the variable segments of the genes from a mouse monoclonal antibody can be joined to human constant segments, such as kappa and gamma 1 or gamma 3. In one example, a chimeric antibody is a hybrid protein composed of the variable or antigen-binding domain from a mouse antibody and the constant or effector domain from a human antibody (such as an antibody that recognizes one of the disclosed pathological angiogenesis endothelial markers listed in Table 9), although other mammalian species can be used, or the variable region can be produced by molecular techniques. Methods of making chimeric antibodies are well known in the art, for example, see U.S. Pat. No. 5,807,715.

Decrease: To reduce the quality, amount, or strength of something. In one example, a therapy decreases a tumor (such as the size of a tumor, the number of tumors, the metastasis of a tumor, or combinations thereof), or one or more symptoms associated with a tumor, for example as compared to the response in the absence of the therapy (such as a therapy administered to affect tumor size by inhibiting pathological angiogenesis via administration of a binding agent capable of binding to one or more of the pathological angiogenesis markers listed in Table 9). In a particular example, a therapy decreases the size of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein as well as those known in the art.

Endothelial cell: Cells that line the interior surface of blood vessels, forming an interface between circulating blood in the lumen and the rest of the vessel wall. For example, endothelial cells line the entire circulatory system. Further, both blood and lymphatic capillaries are composed of a single layer of endothelial cells.

Expression product with Accession No. AK144596: In one example, AK144596 is a protein that is expressed in liver endothelial cells. The term expression product with Accession No. AK144596 includes any expression product with Accession No. AK144596 gene, cDNA, mRNA, or protein from any organism and that is an expression product with Accession No. AK144596 capable of delivering a therapeutic agent specifically to liver endothelial cells.

Nucleic acid and protein sequences for expression product with Accession No. AK144596 are publicly available. For example, GenBank Accession No: AK144596 discloses an expression product with Accession No. AK144596 nucleic acid sequence.

In one example, an expression product with Accession No. AK144596 includes a full-length wild-type (or native) sequence, as well as an expression product with Accession No. AK144596 allelic variants, fragments, homologs or fusion sequences that retain the ability to deliver therapeutic agents specifically to liver endothelial cells. In certain examples, an expression product with Accession No. AK144596 has at least 80% sequence identity, for example at least 85%, 90%, 95%, or 98% sequence identity to an expression product with Accession No. AK144596. In other examples, an expression product with Accession No. AK144596 has a sequence that hybridizes under very high stringency conditions to a sequence set forth in GenBank Accession No. AK144596 and retains expression product with Accession No. AK144596 activity (e.g., the capability to serve as a liver endothelial cell marker).

Forkhead box Q1 (FOXQ1): A member of the evolutionarily conserved winged helix (WH)/forkhead transcription factor gene family. The protein regulates the expression of other genes. In one example, FOXQ1 protein is expressed in brain endothelial cells. The term FOXQ1 includes any FOXQ1 gene, cDNA, mRNA, or protein from any organism and that is FOXQ1 capable of delivering a therapeutic agent specifically to brain endothelial cells.

Nucleic acid and protein sequences for FOXQ1 are publicly available. For example, GenBank Accession Nos.: NM_008239, AK147202, AF010405, AF225950, and NM_033260 disclose FOXQ1 nucleic acid sequences and GenBank Accession Nos.: NP_032265, AAH53850, and NP_150285 disclose FOXQ1 protein sequences.

In one example, FOXQ1 includes a full-length wild-type (or native) sequence, as well as FOXQ1 allelic variants, fragments, homologs or fusion sequences that retain the ability to deliver therapeutic agents specifically to brain endothelial cells. In certain examples, FOXQ1 has at least 80% sequence identity, for example at least 85%, 90%, 95%, or 98% sequence identity to FOXQ1. In other examples, FOXQ1 has a sequence that hybridizes under very high stringency conditions to a sequence set forth in GenBank Accession Nos. NM_008239, AK147202, AF010405, AF225950, or NM_033260 and retains FOXQ1 (e.g., the capability to serve as a brain endothelial cell marker).

Humanized antibodies: An immunoglobulin including a human framework region and one or more CDRs from a non-human (such as a mouse, rat, or synthetic) immunoglobulin. A humanized antibody binds to the same antigen as the donor antibody that provides the CDRs. In on example, a humanized antibody specifically binds to one of the proteins listed in Tables 8 and 9.

The non-human immunoglobulin providing the CDRs is termed a "donor" and the human immunoglobulin providing the framework is termed an "acceptor." In one example, all the CDRs are from the donor immunoglobulin in a humanized immunoglobulin. Constant regions need not be present, but if they are, they are substantially identical to human immunoglobulin constant regions, for instance, at least about 85-90%, such as about 95% or more identical.

The donor CDRs of a humanized antibody can have a limited number of substitutions using amino acids from the acceptor CDR. Hence, all parts of a humanized immunoglobulin, except possibly the CDRs, are substantially identical to corresponding parts of natural human immunoglobulin sequences. The acceptor framework of a humanized immunoglobulin or antibody can have a limited number of substitutions by amino acids taken from the donor framework. Humanized or other monoclonal antibodies can have additional amino acid substitutions which have substantially no effect on antigen binding or other immunoglobulin functions. Exemplary conservative substitutions are described above (see also U.S. Pat. No. 5,585,089). Humanized immunoglobulins can be constructed by means of genetic engineering, for example, see U.S. Pat. Nos. 5,225,539 and 5,585,089, herein incorporated by reference.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (detects sequences that share at least 80% identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (detects sequences that share at least 50% identity)
Hybridization: 6×SSC at RT to 55° C. for 16-20 hours
Wash at least twice: 2×-3×SSC at RT to 55° C. for 20-30 minutes each.

Immunoassay: A biochemical test that measures the level of a substance in a biological sample (such as serum or urine), using the reaction of an antibody or antibodies to its antigen. The assay takes advantage of the specific binding of an antibody to its antigen. The antibodies selected ideally have a high affinity for the antigen (if there is antigen available, a very high proportion of it will bind to the antibody). Both the presence of antigen or antibodies can be measured. For instance, when detecting pathological angiogenesis the presence of a pathological angiogenesis marker can be measured.

Detecting the quantity of antibody or antigen can be achieved by a variety of methods. One of the most common is to label the antigen or antibody. The label can include an enzyme (e.g., luciferase or β-gal), radioisotopes (such as $^{125}$I) or a fluorophore. Other techniques include Western Blot.

Kelch repeat and BTB (POZ) domain: In one example, the Kelch repeat and BTB (POZ) domain is expressed in brain endothelial cells. The term Kelch repeat and BTB (POZ) domain includes any Kelch repeat and BTB (POZ) domain gene, cDNA, mRNA, or protein from any organism and that is Kelch repeat and BTB (POZ) domain capable of delivering a therapeutic agent specifically to brain endothelial cells.

Nucleic acid and protein sequences for Kelch repeat and BTB (POZ) domain are publicly available. For example, GenBank Accession Nos.: XM_486083, XM_979486, XM_921147, NM_014867, and AB018254 disclose Kelch repeat and BTB (POZ) domain nucleic acid sequences and GenBank Accession Nos.: XP_926240, XP_486083, and NP_055682 disclose ankylosis protein sequences.

In one example, Kelch repeat and BTB (POZ) domain includes a full-length wild-type (or native) sequence, as well as Kelch repeat and BTB (POZ) domain allelic variants, fragments, homologs or fusion sequences that retain the ability to deliver therapeutic agents specifically to brain endothelial cells. In certain examples, Kelch repeat and BTB (POZ) domain has at least 80% sequence identity, for example at least 85%, 90%, 95%, or 98% sequence identity to Kelch repeat and BTB (POZ) domain. In other examples, Kelch repeat and BTB (POZ) domain has a sequence that hybridizes under very high stringency conditions to a sequence set forth in GenBank Accession Nos. XM_486083, XM_486083, XM_979486, XM_921147, NM_014867, or AB018254 and retains Kelch repeat and BTB (POZ) domain activity (e.g., the capability to deliver therapeutic agents to brain endothelial cells).

Label: A detectable compound. In some examples, a label is conjugated directly or indirectly to another molecule, such as an antibody or a protein, to facilitate detection of that molecule. For example, the label can be capable of detection by ELISA, spectrophotometry, flow cytometry, or microscopy. Specific, non-limiting examples of labels include fluorophores, chemiluminescent agents, enzymatic linkages, and radioactive isotopes. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998). In a particular example, a label is conjugated to a binding agent that specifically binds to one or more of the pathological angiogenesis endothelial markers disclosed in Table 9 to allow for the detection/screening for pathological angiogenesis and/or the presence of a tumor in a subject.

Malignant: Cells that have the properties of anaplasia invasion and metastasis.

Mammal: This term includes both human and non-human mammals. Examples of mammals include, but are not limited to: humans, pigs, cows, goats, cats, dogs, rabbits and mice.

MBL-associated serine protease-3 (MASP-3): MASP-3 transcripts encode serine proteases that display distinct substrate specificity and associate with Mannan-binding lectin complexes. In one example, MBL-associated serine protease-3 is preferentially expressed in liver endothelial cells. The term MBL-associated serine protease-3 includes any MBL-associated serine protease-3 gene, cDNA, mRNA, or protein from any organism and that is a MBL-associated serine protease-3 capable of delivering a therapeutic agent specifically to liver endothelial cells.

Exemplary nucleic acid and protein sequences for MBL-associated serine protease-3 are publicly available. For example, GenBank Accession Nos.: AB049755, AK031598, NM_139125, NM_001879, and NM_001031849 disclose MBL-associated serine protease-3 nucleic acid sequences and GenBank Accession Nos.: NP_624302, NP_001870, and NP_001027019 disclose MBL-associated serine protease-3 protein sequences.

In one example, a MBL-associated serine protease-3 sequence includes a full-length wild-type (or native) sequence, as well as MBL-associated serine protease-3 allelic variants, fragments, homologs or fusion sequences that retain the ability to deliver therapeutic agents specifically to liver endothelial cells. In certain examples, MBL-associated serine protease-3 has at least 80% sequence identity, for example at least 85%, 90%, 95%, or 98% sequence identity to a MBL-associated serine protease-3. In other examples, a MBL-associated serine protease-3 has a sequence that hybridizes under very high stringency conditions to a sequence set forth in GenBank Accession No. AB049755, AB049755, AK031598, NM_139125, NM_001879, or NM_001031849 and retains MBL-associated serine protease-3 activity (e.g., the capability to deliver therapeutic agents to liver endothelial cells).

MiRP2: The MiRP2 gene encodes a small integral membrane subunit that assembles with HERG, a pore-forming protein, to form a potassium voltage-gated channel. MiRP2 alters the function of the channel. Channels formed with mutant MiRP1 subunits display slower activation, faster deactivation, and increased drug sensitivity.

In one example, MiRP2 is expressed during pathological angiogenesis. The term MiRP2 includes any MiRP2 gene, cDNA, mRNA, or protein from any organism and that is MiRP2 and is expressed during pathological angiogenesis.

Exemplary nucleic acid and protein sequences for MiRP2 are publicly available. For example, GenBank Accession Nos.: DQ832280, NM_020574, AK008744, and NM_005472 disclose MiRP2 nucleic acid sequences and GenBank Accession Nos.: NP_065599, BAB25871, and NP_005463 disclose MiRP2 protein sequences.

In one example, MiRP2 includes a full-length wild-type (or native) sequence, as well as MiRP2 allelic variants, fragments, homologs or fusion sequences that retain the ability to be expressed during pathological angiogenesis and/or modulate pathological angiogenesis. In certain examples, MiRP2 has at least 80% sequence identity, for example at least 85%, 90%, 95%, or 98% sequence identity to MiRP2. In other examples, MiRP2 has a sequence that hybridizes under very high stringency conditions to a sequence set forth in GenBank Accession Nos. DQ832280, NM_020574, AK008744, or NM_005472 and retains MiRP2 activity (e.g., the capability to be expressed during pathological angiogenesis and/or modulate pathological angiogenesis).

Neoplasm: Abnormal growth of cells.

Normal Cell: Non-tumor cell, non-malignant, uninfected cell.

Oncoprotein induced transcript 3 (Oit3): Encodes a secreted ZP domain-containing protein. In one example, oncoprotein induced transcript 3 is expressed in liver endothelial cells. The term oncoprotein induced transcript 3 includes any oncoprotein induced transcript 3 gene, cDNA, mRNA, or protein from any organism and that is a oncoprotein induced transcript 3 capable of delivering a therapeutic agent specifically to liver endothelial cells. Oncoprotein induced transcript 3 is also referred to in the literature as LZP.

Oncoprotein induced transcript 3 nucleic acid and protein sequences are publicly available. For example, GenBank Accession Nos.: NM_010959, AF356506, AY180915, NM_152635, and AY013707 disclose oncoprotein induced transcript 3 nucleic acid sequences and GenBank Accession Nos.: AA022058, NP_035089, NP_689848, and AAG40096 disclose oncoprotein induced transcript 3 protein sequences.

In one example, a oncoprotein induced transcript 3 sequence includes a full-length wild-type (or native) sequence, as well as oncoprotein induced transcript 3 allelic variants, fragments, homologs or fusion sequences that retain the ability to deliver therapeutic agents specifically to liver endothelial cells. In certain examples, oncoprotein induced transcript 3 has at least 80% sequence identity, for example at least 85%, 90%, 95%, or 98% sequence identity to a native oncoprotein induced transcript 3. In other examples, oncoprotein induced transcript 3 has a sequence that hybridizes under very high stringency conditions to a sequence set forth in GenBank Accession Nos. NM_010959, AF356506, AY180915, NM_152635, or AY013707 and retains oncoprotein induced transcript 3 activity.

Pharmaceutically Carriers: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic agents, such as one or more compositions that include a binding agent that specifically binds to at least one of the disclosed pathological angiogenesis marker proteins.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Plexin C1 (VESPR): A large transmembrane receptor. In vitro, plexin-C1 has been shown to bind the GPI-anchored semaphorin Sema7A and the soluble viral semaphorins SemaVA (A39R) and SemaVB (AHV). Plexin C1 engagement by SemaVA inhibits integrin-mediated dendritic cell adhesion and chemotaxis in vitro, suggesting a role for plexin C1 in dendritic cell migration.

In an example, plexin C1 is expressed in liver endothelial cells. The term plexin C1 includes any plexin C1 gene, cDNA, mRNA, or protein from any organism and that is a plexin C1 capable of delivering a therapeutic agent specifically to liver endothelial cells.

Exemplary nucleic acid and protein sequences for plexin C1 are publicly available. For example, GenBank Accession Nos.: NM_018797, XM_622776, AB208934, and NM_005761 disclose plexin C1 nucleic acid sequences and GenBank Accession Nos.: NP_061267, XP_622776, BAD92171, and NP_005752 disclose plexin C1 protein sequences.

In one example, a plexin C1 sequence includes a full-length wild-type (or native) sequence, as well as plexin C1 allelic variants, fragments, homologs or fusion sequences that retain the ability to deliver therapeutic agents specifically to liver endothelial cells. In certain examples, plexin C1 has at least 80% sequence identity, for example at least 85%, 90%, 95%, or 98% sequence identity to a plexin C1. In other examples, a plexin C1 has a sequence that hybridizes under very high stringency conditions to a sequence set forth in GenBank Accession No. NM_018797, XM_622776, AB208934, or NM_005761 and retains plexin C1 activity (e.g., the capability to deliver therapeutic agents to liver endothelial cells).

Polymerase Chain Reaction (PCR): An in vitro amplification technique that increases the number of copies of a nucleic acid molecule (for example, a nucleic acid molecule in a sample or specimen). In an example, a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of a PCR can be characterized by electrophoresis, restriction endonuclease cleavage patterns, oligonucleotide hybridization or ligation, and/or nucleic acid sequencing, using standard techniques.

Preimplantation protein 4 (Prei4): The Prei4 gene is expressed during mouse preimplantation embryogenesis. It is a putative glycerophosphodiester phosphodiesterase. In one example, Prei4 is expressed in brain endothelial cells. The term Prei4 includes any Prei4 gene, cDNA, mRNA, or protein from any organism and that is Prei4 capable of delivering a therapeutic agent specifically to brain endothelial cells.

Nucleic acid and protein sequences for Prei4 are publicly available. For example, GenBank Accession Nos.: NM_001042671, NM_028802, BC006887, and NM_019593 disclose Prei4 nucleic acid sequences and GenBank Accession Nos.: NP_001036136, NP_062539, and Q9NPB8 disclose Prei4 protein sequences.

In one example, Prei4 includes a full-length wild-type (or native) sequence, as well as Prei4 allelic variants, fragments, homologs or fusion sequences that retain the ability to deliver therapeutic agents specifically to brain endothelial cells. In certain examples, Prei4 has at least 80% sequence identity, for example at least 85%, 90%, 95%, or 98% sequence identity to Prei4. In other examples, Prei4 has a sequence that hybridizes under very high stringency conditions to a sequence set forth in GenBank Accession Nos. NM_001042671, NM_028802, BC006887, or NM_019593 and retains Prei4 activity (e.g., the capability to deliver therapeutic agents to brain endothelial cells).

Probes and primers: Nucleic acid probes and primers can be readily prepared based on the nucleic acid molecules provided in this disclosure. A probe includes an isolated nucleic acid attached to a detectable label or reporter molecule. Exemplary labels include radioactive isotopes, enzyme substrates, co-factors, ligands, chemiluminescent or fluorescent agents, haptens, and enzymes.

Primers are short nucleic acid molecules such as DNA oligonucleotides, 10 nucleotides or more in length. Longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.).

Progestin and adipoQ receptor family member V (Paqr5): An integral membrane protein that binds progesterone. Paqr5 is a putative G-protein coupled receptor involved in signal transduction in response to steroids such as progesterone.

In one example, Paqr5 is expressed in brain endothelial cells. The term Progestin and adipoQ receptor family member V includes any Progestin and adipoQ receptor family member V gene, cDNA, mRNA, or protein from any organism and that is Progestin and adipoQ receptor family member V capable of delivering a therapeutic agent specifically to brain endothelial cells.

Exemplary nucleic acid and protein sequences for Progestin and adipoQ receptor family member V are publicly available. For example, GenBank Accession Nos: NM_028748, AK035475, AY424283, and NM_017705 disclose Progestin and adipoQ receptor family member V nucleic acid sequences and GenBank Accession Nos.: NP_083024, BAC29072, AAR08371, and NP_060175 disclose Progestin and adipoQ protein sequences.

In one example, Progestin and adipoQ receptor family member V includes a full-length wild-type (or native) sequence, as well as Progestin and adipoQ receptor family member V allelic variants, fragments, homologs or fusion sequences that retain the ability to deliver therapeutic agents specifically to brain endothelial cells. In certain examples, Progestin and adipoQ receptor family member V has at least 80% sequence identity, for example at least 85%, 90%, 95%, or 98% sequence identity to Progestin and adipoQ receptor family member V. In other examples, Progestin and adipoQ receptor family member V has a sequence that hybridizes under very high stringency conditions to a sequence set forth in GenBank Accession Nos. NM_028748, NM_028748, AK035475, AY424283, or NM_017705 and retains Progestin and adipoQ receptor family member V activity (e.g., the capability to deliver therapeutic agents to brain endothelial cells).

Ptprn (IA-2): PTPRN (IA-2) is a major autoantigen in type 1 diabetes. Autoantibodies against PTPRN appear years before the development of clinical disease. PTPRN is an enzymatically inactive member of the transmembrane protein tyrosine phosphatase family and is an integral component of secretory granules in neuroendocrine cells. PTPRN is an important regulator of dense core vesicle number and glucose-induced and basal insulin secretion.

In one example, Ptprn is expressed during pathological angiogenesis. The term Ptprn includes any Ptprn gene, cDNA, mRNA, or protein from any organism and that is Ptprn and is preferentially expressed during pathological angiogenesis. Ptprn is also known in the literature as IA-2.

Exemplary nucleic acid and protein sequences for Ptprn are publicly available. For example, GenBank Accession Nos.: DQ832283, NM_008985, AK041296, NM_002846, and L18983 disclose Ptprn nucleic acid sequences and GenBank Accession Nos.: NP_033011, NP_002837, and AAA90974 disclose Ptprn (IA-2) protein sequences.

In one example, Ptprn includes a full-length wild-type (or native) sequence, as well as Ptprn allelic variants, fragments, homologs or fusion sequences that retain the ability to be preferentially expressed during pathological angiogenesis and/or modulate pathological angiogenesis. In certain examples, Ptprn has at least 80% sequence identity, for example at least 85%, 90%, 95%, or 98% sequence identity to Ptprn. In other examples, Ptprn has a sequence that hybridizes under very high stringency conditions to a sequence set forth in GenBank Accession Nos. DQ832283, NM_008985, AK041296, NM_002846, or L18983 and retains Ptprn activity (e.g., the capability to be expressed during pathological angiogenesis and/or modulate pathological angiogenesis).

Putative G-protein coupled receptor NM_033616 or Component of Sp100-rs (Csprs): A putative G-protein coupled receptor. In one example, putative G-protein coupled receptor NM_033616 is expressed in liver endothelial cells. The term putative G-protein coupled receptor NM_033616 includes any putative G-protein coupled receptor NM_033616 gene, cDNA, mRNA, or protein from any organism and that is a putative G-protein coupled receptor NM_033616 capable of delivering a therapeutic agent specifically to liver endothelial cells.

Exemplary nucleic acid and protein sequences for putative G-protein coupled receptor NM_033616 are publicly available. For example, GenBank Accession Nos.: NM_033616, AK037063, and XM_979370 disclose putative G-protein coupled receptor NM_033616 nucleic acid sequences and GenBank Accession Nos.: NP_291094 and XP_984464 disclose putative G-protein coupled receptor NM_033616 protein sequences.

In one example, a putative G-protein coupled receptor NM_033616 sequence includes a full-length wild-type (or native) sequence, as well as putative G-protein coupled receptor NM_033616 allelic variants, fragments, homologs or fusion sequences that retain the ability to deliver therapeutic agents specifically to liver endothelial cells. In certain examples, putative G-protein coupled receptor NM_033616 has at least 80% sequence identity, for example at least 85%, 90%, 95%, or 98% sequence identity to a putative G-protein coupled receptor NM_033616. In other examples, a putative G-protein coupled receptor NM_033616 has a sequence that hybridizes under very high stringency conditions to a sequence set forth in GenBank Accession Nos. NM_033616, AK037063, or XM_979370 and retains putative G-protein coupled receptor NM_033616 activity (e.g., the capability to target agents to liver endothelial cells).

Putative transmembrane protein Accession No. NM_023438: A putative transmembrane protein. In one example, putative transmembrane protein Accession No. NM_023438 is expressed in liver endothelial cells. The term putative transmembrane protein Accession No. NM_023438 includes any putative transmembrane protein Accession No. NM_023438 gene, cDNA, mRNA, or protein from any organism and that is a putative transmembrane protein Accession No. NM_023438 capable of delivering a therapeutic agent specifically to liver endothelial cells.

Exemplary nucleic acid and protein sequences for putative transmembrane protein Accession No. NM_023438 are publicly available. For example, GenBank Accession Nos.: NM_023438, NM_207313, and BN000149 disclose putative transmembrane protein Accession No. NM_023438 nucleic acid sequences and GenBank Accession Nos.:

NP_075927, NP_997196, and CAD80169 disclose putative transmembrane protein Accession No. NM_023438 protein sequences.

In one example, a putative transmembrane protein Accession No. NM_023438 sequence includes a full-length wild-type (or native) sequence, as well as putative transmembrane protein Accession No. NM_023438 allelic variants, fragments, homologs or fusion sequences that retain the ability to deliver therapeutic agents specifically to liver endothelial cells. In certain examples, putative transmembrane protein Accession No. NM_023438 has at least 80% sequence identity, for example at least 85%, 90%, 95%, or 98% sequence identity to a putative transmembrane protein Accession No. NM_023438. In other examples, a putative transmembrane protein Accession No. NM_023438 has a sequence that hybridizes under very high stringency conditions to a sequence set forth in GenBank Accession Nos. NM_023438, NM_207313, and BN000149 and retains putative transmembrane protein Accession No. NM_023438 activity (e.g., the capability to target agents to liver endothelial cells).

Putative transmembrane protein Accession No. NM_029001: A putative transmembrane protein. In one example, putative transmembrane protein Accession No. NM_029001 is expressed in brain endothelial cells. The term putative transmembrane protein Accession No. NM_029001 includes any putative transmembrane protein Accession No. NM_029001 gene, cDNA, mRNA, or protein from any organism and that is a putative transmembrane protein Accession No. NM_029001 capable of delivering a therapeutic agent specifically to brain endothelial cells.

Exemplary nucleic acid and protein sequences for putative transmembrane protein Accession No. NM_029001 are publicly available. For example, GenBank Accession Nos.: NM_029001, NM_024930, and AB181393 disclose putative transmembrane protein Accession No. NM_029001 nucleic acid sequences and GenBank Accession Nos.: NP_083277, NP_079206, and BAD93238 disclose putative transmembrane protein Accession No. NM_029001 protein sequences.

In one example, a putative transmembrane protein Accession No. NM_029001 sequence includes a full-length wild-type (or native) sequence, as well as putative transmembrane protein Accession No. NM_029001 allelic variants, fragments, homologs or fusion sequences that retain the ability to deliver therapeutic agents specifically to brain endothelial cells. In certain examples, putative transmembrane protein Accession No. NM_029001 has at least 80% sequence identity, for example at least 85%, 90%, 95%, or 98% sequence identity to a putative transmembrane protein Accession No. NM_029001. In other examples, a putative transmembrane protein Accession No. NM_029001 has a sequence that hybridizes under very high stringency conditions to a sequence set forth in GenBank Accession No. NM_029001, NM_024930, or AB181393 and retains putative transmembrane protein Accession No. NM_029001 activity (e.g., the capability to target agents to brain endothelial cells).

Putative transmembrane protein Accession No. NM_144830: NM_144830 encodes a putative transmembrane protein. In one example, putative transmembrane protein Accession No. NM_144830 is expressed in liver endothelial cells. The term putative transmembrane protein Accession No. NM_144830 includes any putative transmembrane protein Accession No. NM_144830 gene, cDNA, mRNA, or protein from any organism and that is putative transmembrane protein Accession No. NM_144830 capable of delivering a therapeutic agent specifically to liver endothelial cells.

Exemplary nucleic acid and protein sequences for putative transmembrane protein Accession No. NM_144830 are publicly available. For example, GenBank Accession Nos.: NM_144830, AK154217, NM_145041, and XM_001133074 disclose putative transmembrane protein Accession No. NM_144830 nucleic acid sequence and GenBank Accession Nos.: NP_659079, BAE32441, NP_659478, and XP_001133074 disclose putative transmembrane protein Accession No. NM_144830 protein sequences.

In one example, putative transmembrane protein Accession No. NM_144830 includes a full-length wild-type (or native) sequence, as well as putative transmembrane protein Accession No. NM_144830 allelic variants, fragments, homologs or fusion sequences that retain the ability to deliver therapeutic agents specifically to liver endothelial cells. In certain examples, putative transmembrane protein Accession No. NM_144830 has at least 80% sequence identity, for example at least 85%, 90%, 95%, or 98% sequence identity to putative transmembrane protein Accession No. NM_144830. In other examples, putative transmembrane protein Accession No. NM_144830 has a sequence that hybridizes under very high stringency conditions to a sequence set forth in GenBank Accession No. NM_144830, AK154217, NM_145041, or XM_001133074 and retains putative transmembrane protein Accession No. NM_144830 activity (e.g., the capability to target agents to liver endothelial cells).

Putative secreted protein Accession No. XM_620023: XM_620023 encodes a putative secreted protein. In one example, putative secreted protein Accession No. XM_620023 is expressed in brain endothelial cells. The term putative secreted protein Accession No. NM_620023 includes any putative secreted protein Accession No. XM_620023 gene, cDNA, mRNA, or protein from any organism and that is a putative secreted protein Accession No. NM_620023 capable of delivering a therapeutic agent specifically to brain endothelial cells.

Exemplary nucleic acid and protein sequences for putative secreted protein Accession No. XM_620023 are publicly available. For example, GenBank Accession Nos.: XM_620023, AK128180, and BX648118 disclose secreted protein Accession No. XM_620023 nucleic acid sequences and GenBank Accession Nos.: XP_620023, BAC87313, and CAH56187 disclose putative secreted protein Accession No. XM_620023 protein sequences.

In one example, a putative secreted protein Accession No. XM_620023 sequence includes a full-length wild-type (or native) sequence, as well as putative secreted protein Accession No. XM_620023 allelic variants, fragments, homologs or fusion sequences that retain the ability to deliver therapeutic agents specifically to brain endothelial cells. In certain examples, putative secreted protein Accession No. XM_620023 has at least 80% sequence identity, for example at least 85%, 90%, 95%, or 98% sequence identity to a putative secreted protein Accession No. XM_620023. In other examples, a putative secreted protein Accession No. XM_620023 has a sequence that hybridizes under very high stringency conditions to a sequence set forth in GenBank Accession Nos. XM_620023, BAC87313, and CAH56187 and retains putative secreted protein Accession No. NM_620023 activity (e.g., the capability to target agents to brain endothelial cells).

Sample: Biological specimens containing genomic DNA, cDNA, RNA, or protein obtained from the cells of a subject, such as those present in peripheral blood, urine, saliva, semen, tissue biopsy, surgical specimen, fine needle aspriates, amniocentesis samples and autopsy material. In one example, a sample includes lung, colon, breast or liver cancer cells obtained from a subject.

Sequence identity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species that are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, J. Mol. Biol. 48:443, 1970; Pearson & Lipman, *Proc. Natl. Acad. Sci. USA* 85:2444, 1988; Higgins & Sharp, *Gene,* 73:237-44, 1988; Higgins & Sharp, CABIOS 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: −i is set to a file containing the first nucleic acid sequence to be compared (such as C:\seq1.txt); −j is set to a file containing the second nucleic acid sequence to be compared (such as C:\seq2.txt); −p is set to blastn; −o is set to any desired file name (such as C:\output.txt); −q is set to −1; −r is set to 2; and all other options are left at their default setting. For example, the following command can be used to generate an output file containing a comparison between two sequences: C:\Bl2seq−i c:\seq1.txt−j c:\seq2.txt−p blastn−o c:\output.txt−q−1−r 2.

To compare two amino acid sequences, the options of Bl2seq can be set as follows: −i is set to a file containing the first amino acid sequence to be compared (such as C:\seq1.txt); −j is set to a file containing the second amino acid sequence to be compared (such as C:\seq2.txt); −p is set to blastp; −o is set to any desired file name (such as C:\output.txt); and all other options are left at their default setting. For example, the following command can be used to generate an output file containing a comparison between two amino acid sequences: C:\Bl2seq−i c:\seq1.txt−j c:\seq2.txt−p blastp−o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence contains a region that shares 75 percent sequence identity to that identified sequence (15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong *Comput. Appl. Biosci.* 10: 67-70, 1994). Other programs use SEG. In addition, a manual alignment can be performed. Proteins with even greater similarity will show increasing percentage identities when assessed by this method, such as at least 75%, 80%, 85%, 90%, 95%, or 99% sequence identity to any protein listed in Tables 8 and 9.

When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 60%, 70%, 75%, 80%, 85%, 90%, 95%, 98%, or 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions. Stringent conditions are sequence-dependent and are different under different environmental parameters. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method. In particular, homologous nucleic acid sequences can possess at least 60%, 70%, 80%, 90%, 95%, 98% or 99% sequence identity to the nucleic acid sequences that encode endothelial cell proteins listed in Tables 8 and 9. In a further example, homologous proteins can possess at least 60%, 70%, 80%, 90%, 95%, 98% or 99% sequence identity to the endothelial cell proteins listed in Tables 8 and 9.

One of skill in the art will appreciate that these sequence identity ranges are provided for guidance only; it is possible that strongly significant homologs could be obtained that fall outside the ranges provided.

An alternative (and not necessarily cumulative) indication that two nucleic acid sequences are substantially identical is that the polypeptide which the first nucleic acid encodes is immunologically cross reactive with the polypeptide encoded by the second nucleic acid.

Serial analysis of gene expression (SAGE): A technique that can be used to characterize gene expression, or more precisely gene transcription. Briefly, the SAGE approach is a method for the rapid quantitative and qualitative analysis of mRNA transcripts based upon the isolation and analysis of short defined sequence tags (SAGE Tags) corresponding to expressed genes. Each Tag is a short nucleotide sequence (such as 9-33 base pairs in length) from a defined position in the transcript. In the SAGE method, the Tags are dimerized to reduce bias inherent in cloning or amplification reactions (See, U.S. Pat. No. 5,695,937). SAGE is particularly suited to the characterization of genes associated with vasculature stimulation or inhibition because it is capable of detecting rare sequence, evaluating large numbers of sequences at one time, and to provide a basis for the identification of previously unknown genes.

Specific Binding Agent: An agent that binds substantially only to a defined target such as a protein, enzyme, polysaccharide, oligonucleotide, DNA, RNA, recombinant vector or a small molecule. Thus, a protein-specific binding agent binds substantially only the defined protein, or to a specific region within the protein. In an example, a "specific binding agent" includes antibodies and other agents that bind substantially to a specified polypeptide. Exemplary antibodies include monoclonal or polyclonal antibodies that are specific for the polypeptide, as well as immunologically effective portions ("fragments") thereof. In an example, a "specific binding agent" is capable of binding to at least one of the disclosed physiological or pathological angiogenesis endothelial marker proteins. For instance, the "specific binding agent" is an antibody specific for at least one of the disclosed physiological or pathological angiogenesis endothelial marker proteins. In an additional example, the "specific binding agent" is capable of interacting with at least one of the organ-specific endothelial marker proteins.

The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999). In further examples, the specific binding agent is capable of binding to a mRNA or small molecule that results in pathological angiogenesis being inhibited.

Subject: Living multicellular vertebrate organisms, a category which includes both human and veterinary subjects that are in need of the desired biological effect, such as treatment of a tumor. Examples include, but are not limited to: humans, apes, dogs, cats, mice, rats, rabbits, horses, pigs, and cows.

Therapeutically Effective Amount: An amount of a composition that alone, or together with an additional therapeutic agent(s) (for example a chemotherapeutic agent), induces the desired response (e.g., treatment of a tumor). The preparations disclosed herein are administered in therapeutically effective amounts.

In one example, a desired response is to decrease tumor size or metastasis in a subject to whom the therapy is administered. Tumor metastasis does not need to be completely eliminated for the composition to be effective. For example, a composition can decrease metastasis by a desired amount, for example by at least 20%, at least 50%, at least 60%, at least 70%, at least 80%, at least 90%, at least 95%, at least 98%, or even at least 100% (elimination of the tumor), as compared to metastasis in the absence of the composition.

In particular examples, it is an amount of the therapeutic agent conjugated to the specific binding agent effective to decrease a number of cancer cells, such as in a subject to whom it is administered, for example a subject having one or more carcinomas. The cancer cells do not need to be completely eliminated for the composition to be effective. For example, a composition can decrease the number of cancer cells by a desired amount, for example by at least 20%, at least 50%, at least 60%, at least 70%, at least 80%, at least 90%, at least 95%, at least 98%, or even at least 100% (elimination of detectable cancer cells), as compared to the number of cancer cells in the absence of the composition.

In other examples, it is an amount of the specific binding agent for one or more of the disclosed pathological angiogenesis protein markers capable of reducing pathological angiogenesis by least 20%, at least 50%, at least 60%, at least 70%, at least 80%, at least 90%, at least 95%, at least 98%, or even at least 100% (elimination of detectable pathological angiogenesis) by the specific binding agent, or both, effective to decrease the metastasis of a tumor.

A therapeutically effective amount of a specific binding agent for at least one of the disclosed pathological angiogenesis protein markers, or cancer cells lysed by a therapeutic molecule conjugated to the agent, can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 µg-10 mg per 70 kg body weight if administered intravenously and about 10 µg-100 mg per 70 kg body weight if administered intratumorally.

Treating a disease: "Treatment" refers to a therapeutic intervention that ameliorates a sign or symptom of a disease or pathological condition, such a sign or symptom of a tumor. Treatment can also induce remission or cure of a condition, such as a tumor. In particular examples, treatment includes preventing a disease, for example by inhibiting the full development of a disease, such as preventing development of a tumor (such as a metastasis). Prevention of a disease does not require a total absence of a tumor. For example, a decrease of at least 50% can be sufficient.

Tumor: A neoplasm. Includes solid and hematological (or liquid) tumors. Examples of solid tumors, such as sarcomas and carcinomas, include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Unit dose: A physically discrete unit containing a predetermined quantity of an active material calculated to individually or collectively produce a desired effect, such as a therapeutic effect. A single unit dose or a plurality of unit doses can be used to provide the desired effect, such as treatment of a tumor, for example a metastatic tumor. In one example, a unit dose includes a desired amount of an agent that decreases or inhibits pathological angiogenesis.

Vscp: Encodes an SH2-containing protein. In one example, Vscp is expressed during pathological angiogenesis. The term Vscp includes any Vscp gene, cDNA, mRNA, or protein from any organism and that is Vscp and is expressed during pathological angiogenesis.

Exemplary nucleic acid and protein sequences for Vscp are publicly available. For example, GenBank Accession Nos.: DQ832275, XM_357399, AK032598, XM_375698, and XM_939275 disclose Vscp nucleic acid sequences and GenBank Accession Nos.: XP_357399, XP_375698, and XP_944368 disclose Vscp protein sequences.

In one example, Vscp includes a full-length wild-type (or native) sequence, as well as Vscp allelic variants, fragments, homologs or fusion sequences that retain the ability to be expressed during pathological angiogenesis and/or modulate pathological angiogenesis. In certain examples, Vscp has at least 80% sequence identity, for example at least 85%, 90%, 95%, or 98% sequence identity to Vscp. In other examples, Vscp has a sequence that hybridizes under very high stringency conditions to a sequence set forth in GenBank Accession No. DQ832275, XM_357399, AK032598, XM_375698, and XM_939275 and retains Vscp activity (e.g., the capability to be expressed during pathological angiogenesis and/or modulate pathological angiogenesis).

Western blot: A method in molecular biology/biochemistry/immunogenetics to detect protein in a biological sample, such as a tissue homogenate or extract. Gel electrophoresis can be employed to separate denatured proteins by mass. Following separation, the proteins are transferred out of the gel and onto a membrane (typically nitrocellulose), where they are "probed" using antibodies specific to the protein. As a result, the amount of protein in the sample can be examined and compared to other protein levels. Other techniques also using antibodies allow detection of proteins in tissues (immunohistochemistry) and cells (immunocytochemistry).

Additional terms commonly used in molecular genetics can be found in Benjamin Lewin, Genes V published by Oxford University Press, 1994 (ISBN 0-19-854287-9); Kendrew et al (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Methods of Treatment

It is shown herein that pathological angiogenesis is associated with the increased expression of at least thirteen endothelial cell proteins (such as the pathological angiogenesis marker proteins listed in Table 9). It is also demonstrated that these proteins are not increased during physiological angiogenesis. In addition, expression levels of various endothelial cell proteins have been found to be dependent upon the organ in which the proteins are expressed. Based on these observations, methods of treating pathological angiogenesis, such as pathological angiogenesis associated with a tumor, are disclosed. Further, methods of delivering a therapeutic agent to a specific organ to treat a disease are disclosed.

Methods are disclosed herein for treating pathological angiogenesis, such as that associated with a tumor. In one example, the method includes administering a therapeutically effective amount of a composition to a subject in which the composition includes a specific binding agent that preferentially binds to one or more pathological angiogenesis marker proteins listed in Table 9 or a subset thereof, such as at least 1, at least 2, at least 3, at least 5, at least 10, or at least 12 (for example, 1, 2, 3, 4, 5, 6, 7, 8, 9, 10, 11, 12, or 13 of those listed). In particular examples, the one or more pathological angiogenesis marker proteins are Vscp, CD276, MiRP2, Ptprn (IA-2), ankylosis or combinations thereof. The specific binding agent can be an antibody to one or more of the pathological angiogenesis marker proteins conjugated to a therapeutic molecule, such as a cytotoxin, chemotherapeutic reagent, radionucleotide or a combination thereof.

Inhibiting Pathological Angiogenesis

Pathological angiogenesis is a physiological process involving the growth of new blood vessels under pathological conditions. For example, pathological angiogenesis is involved in the transition of tumors from a dormant state to a malignant state. Inhibition of pathological angiogenesis does not require 100% inhibition, but can include at least a reduction (such as a reduction of at least 10% or at least 25%) if not a complete inhibition of new blood vessels associated with a specific pathological condition.

In an example, inhibiting pathological angiogenesis can be used to treat a tumor. Treatment of a tumor by reducing new blood vessel growth can include preventing or delaying the development of the tumor in a subject (such as preventing metastasis of a tumor), and also includes reducing signs or symptoms associated with the presence of such a tumor (for example by reducing the size or volume of the tumor or a metastasis thereof). Such reduced growth can in some examples decrease or slow metastasis of the tumor, or reduce the size or volume of the tumor by at least 10%, at least 20%, at least 50%, or at least 75%. For example, pathological angiogenesis can be inhibited to treat cancer such as a liver, breast, colon and lung cancer. In another example, inhibition of pathological angiogenesis includes reducing the invasive activity of the tumor in the subject, for example by reducing the ability of the tumor to metastasize by reducing or inhibiting new blood vessel growth. In some examples, treatment using the methods disclosed herein prolongs the time of survival of the subject.

Specific Binding Agents

Specific binding agents are agents that bind with higher affinity to a molecule of interest, than to other molecules. For example, a specific binding agent can be one that binds with high affinity to one of the proteins listed in Tables 8 and 9, but does not substantially bind to another protein. In a specific example, a specific binding agent binds to one of the proteins listed in Tables 8 and 9 with a binding affinity in the range of 0.1 to 20 nM.

Examples of specific binding agents include antibodies, ligands, recombinant proteins, peptide mimetics, and soluble receptor fragments. One specific example of a specific binding agent is an antibody, such as a monoclonal or polyclonal antibody. Methods of making antibodies that can be used clinically are known in the art. Particular antibodies and methods that can be used to produce them are described in detail below.

Another specific example of a specific binding agent is a cell surface receptor ligand. Many cell surface receptors have natural ligands that often bind the receptors with high affinity. The ligands, that can be either soluble or cell surface bound, can be used to direct cytotoxic agents to tumors. For example, VEGF has been fused to the toxin gelonin and used in preclinical models to prevent the growth of several tumor types. In an example, the ligand is cell surface receptor itself and a recombinant protein including the extracellular portion of the ligand can be used as a specific binding agent. For instance, the extracellular domain can be fused to a toxin or labeled with an agent that allows detection of the tumor endothelium. In a particular example, the cell surface ligand 4-1BBL can be used as a specific binding agent for CD137. In other examples, the ligand for CD276 or CD109 can be used.

In a further example, small molecular weight inhibitors or antagonists of the receptor protein can be used to regulate pathological angiogenesis. In a particular example, small molecular weight inhibitors or antagonists of the MiRP2 protein are used to inhibit pathological angiogenesis.

In other specific examples, the function of secreted proteins that participate in angiogenesis may be altered by using antibodies that recognize the secreted proteins, or soluble recombinant receptor fragments. An example of this is bevacizumab (Avastin), a monoclonal antibody that recognizes VEGF which has been approved by the FDA for the treatment of human metastatic colorectal cancer and non-small cell lung cancer. The VEGF-trap is a receptor fusion protein that also binds to and blocks VEGF and is also currently in clinical development.

Specific binding agents can be therapeutic, for example by reducing or inhibiting the biological activity of a protein. For example, a specific binding agent that binds with high affinity to one of the proteins listed in Tables 8 and 9, may substantially reduce the biological function of the protein (for example, the ability of the protein to promote pathological angiogenesis). In other examples, a specific binding agent is conjugated to a therapeutic molecule, for example an anti-tumor agent. In this way, the specific binding agent permits targeting of the therapeutic molecule to the cells of interest, such as vascular endothelium. Such agents can be administered in therapeutically effective amounts to individuals in need thereof, such as a subject having a tumor.

Therapeutic Molecules

Therapeutic molecules include agents that can be used to treat a disease, such as a tumor. In a specific example, a therapeutic molecule is one that alone or together with an additional compound induces the desired therapeutic response. One or more therapeutic molecules can be conjugated directly or indirectly to a specific binding agent, such as an antibody that binds to one of the proteins listed in Tables 8 and 9. For example, an antibody that binds to CD276, or Vscp can be conjugated to an anti-tumor agent.

In an example, a therapeutic agent is an anti-tumor agent such as a cytotoxin, chemotherapeutic reagent, radionucleotide or a combination thereof. Non-limiting examples of suitable chemotherapeutic agents for coupling to antibodies to achieve an anti-tumor effect include fluorouracil, doxorubicin, adriamycin, daunorubicin, methotrexate, daunomycin, neocarzinostatin, and carboplatin. For example, the anti-tumor agent 5-fluorouracil can be conjugated to a specific binding agent to treat a tumor such as breast cancer. Non-limiting examples of suitable toxins include bacterial, plant, and other toxins such as diphtheria toxin, pseudomonas exotoxin A, staphylococcal enterotoxin A, abrin-A toxin, ricin A (deglycosylated ricin A and native ricin A), TGF-alpha toxin, cytotoxin from Chinese cobra (naja naja atra), and gelonin (a plant toxin). For example, the anti-tumor agent diphtheria toxin can be conjugated to a specific binding agent such as CD276 to treat a tumor such as cancer.

Additional therapeutic agents can be used for coupling to specific binding agents (such as antibodies) to generate an anti-tumor agent. In an example, a therapeutic agent is a ribosome inactivating protein from plants, bacteria and fungi. Non-limiting examples of suitable ribosome inactivating proteins for coupling to specific binding agents (e.g., antibodies) include restrictocin (a ribosome inactivating protein produced by *Aspergillus restrictus*), saporin (a ribosome inactivating protein from *Saponaria officinalis*), and RNase.

In a particular example, a therapeutic composition that includes a therapeutically effective amount of a binding agent specific for one or more of the disclosed organ-specific or pathological angiogenesis marker proteins (as listed in Tables 8 and 9) further includes therapeutically effective amounts of one or more other biologically active compounds. Examples of biologically active compounds include, but are not limited to: anti-neoplastic agents (such as chemotherapeutics), antibiotics, alkylating agents, antioxidants, adjuvants, and so forth (such as those listed below under "additional treatments"). However, one skilled in the art will appreciate that the composition including a therapeutically effective amount of a binding agent specific for one or more of the disclosed pathological angiogenesis or organ-specific marker proteins and the other biologically active compounds can also be administered separately (instead of in a single composition).

Depending on the endothelial marker, ligands or antibodies that target them may be directly shuttled across the endothelial layer into the underlying tissue by a process known as transcytosis. [For example, see McIntosh et al. *Proc. Natl. Acad. Sci. U.S.A.* 2002 99(4):1996; Gumbleton et al. *J. Control Release.* 2003 87(1-3):139-51]. Thus, site-directed pharmacodelivery may be accomplished by use of cell surface endothelial markers specific for certain organs, such as liver or brain endothelium. Drugs can be conjugated to antibodies for selective delivery. A higher local concentration of drug may result in higher efficacy with fewer side effects. Even if antibodies directed to a particular endothelial marker do not naturally enter a transcytotic pathway, they can be forced to do so, for example through the generation of a bispecific antibody that targets both the endothelial marker and a protein present in caveolae, such as Caveolin-1.

Pre-Screening Subjects

In some examples, subjects are initially screened to determine if they have increased expression levels of the disclosed pathological angiogenesis markers in their serum, whether they have a tumor that has increased expression levels of the disclosed pathological angiogenesis markers or a combination thereof. For example, the pathological angiogenesis markers provided herein can be used to screen subjects to determine if they are candidates for the disclosed therapies (see Section III.B).

Exemplary Tumors

A tumor is an abnormal growth of tissue that results from excessive cell division. A particular example of a tumor is cancer. For example, the current application provides methods for the treatment (such as the prevention or reduction of metastasis) of tumors (such as cancers). In some examples, the tumor is treated in vivo, for example in a mammalian subject, such as a human subject. Exemplary tumors that can be treated using the disclosed methods include, but are not limited to: cancers of the liver, breast, colon, and lung, including metastases of such tumors to other organs.

Treating Particular Organs

In further examples, methods of delivering a therapeutic or diagnostic agent to a specific organ to treat a disease are disclosed. In specific examples, the method includes administering a therapeutically effective amount of a composition that includes a binding agent that preferentially binds to one or more organ-specific endothelial marker proteins provided in Table 8 and a therapeutic agent to evoke a therapeutic response in the specific organ.

In one example, a therapeutic agent is delivered to the brain via a composition including a specific binding agent (such as an antibody) to one or more of the disclosed brain endothelial marker proteins in Table 8 and a therapeutic agent to evoke a desired therapeutic response. For example, the one or more brain endothelial marker proteins is Glucose transporter GLUT-1, Organic anion transporter 2, Pleiotrophin, ATPase class V, type 10A, Peptidoglycan recognition protein 1, Organic anion transporter 14, Forkhead box Q1, Organic anion transporter 3, SN2 (Solute carrier family 38, member 5), Inter-alpha (globulin) inhibitor H5, Solute carrier 38 member 3, Zinc finger protein of the cerebellum 2, Testican-2, 3-HMG-CoA synthase 2, Progestin and adipoQ receptor family member V, APC down-regulated 1 Drapc1, GDPD phosphodiesterase family Accession No. NM_001042671, putative transmembrane protein Accession No. NM_029001, DES2 lipid desaturase/C4-hyroxylase, Kelch repeat and BTB (POZ) domain, Lipolysis stimulated receptor, Glutathione S-transferase alpha 4, TNF receptor superfamily member 19, T-box 1 or putative secreted protein Accession No. XM_620023). In another example, the one or more brain endothelial marker proteins include GDPD phosphodiesterase family Accession No. NM_001042671, Forkhead box Q1 (FOXQ1), putative transmembrane protein Accession No. NM_029001, Kelch repeat and BTB (POZ) domain, Progestin and adipoQ receptor family member V, or putative secreted protein Accession No. XM_620023 or combinations thereof such as at least 1, at least 2, at least 3, or at least 5 (for example, 1, 2, 3, 4, 5, or 6).

In a particular example, the desired therapeutic response is to reduce the growth of brain tumor cells or even kill the brain tumor cells (for example the therapeutic agent inducing cells to undergo apoptosis). Such reduced growth can in some examples decrease or slow metastasis of the brain tumor, or reduce the size or volume of the brain tumor. In another example, the desired therapeutic response is to treat a disease of the brain such as depression or a stroke.

In additional examples, a therapeutic agent is delivered to the liver via a composition including a specific binding agent to the one or more liver endothelial marker proteins and a therapeutic agent to evoke a desired therapeutic response. In an example, the specific binding agent is an antibody that specifically binds to one or more of the liver endothelial marker proteins disclosed in Table 8. In a further example, the one or more liver endothelial marker proteins is deoxyribonuclease 1-like 3, LZP oncoprotein induced transcript 3, putative transmembrane protein Accession No. NM_023438, CD32 15, putative G-protein coupled receptor NM_033616, C-type lectin-like receptor 2, C-type lectin domain family 4 member g 16, Plexin C1, Wnt9B, Accession No. AK144596, GATA-binding protein 4, MBL-associated serine protease-3, Renin binding protein, putative transmembrane protein Accession No. NM_144830, or Retinoic acid receptor, beta. In another example, the one or more liver endothelial marker proteins includes oncoprotein induced transcript 3, putative transmembrane protein Accession No. NM_023438, putative G-protein coupled receptor NM_033616, Plexin C1, MBL-associated serine protease-3, Accession No. AK144596, putative transmembrane protein Accession No. NM_144830 or combinations thereof such as at least 1, at least 2, at least 3, or at least 5 (for example, 1, 2, 3, 4, 5, 6, or 7).

In an example, the desired therapeutic response is to reduce the growth of liver tumor cells or even kill the liver tumor cells (for example the therapeutic agent inducing cells to undergo apoptosis). Such reduced growth can in some examples decrease or slow metastasis of the liver tumor, or reduce the size or volume of a liver tumor. In another example, the desired therapeutic response is to treat a liver disease.

In further examples, a diagnostic agent is delivered to a specific organ such as the brain or liver via a composition including a specific binding agent such as an antibody to one or more of the disclosed organ-specific endothelial marker proteins in Table 8. For example, a diagnostic agent can be delivered to the brain via a specific binding agent that is capable of binding to one or more of the disclosed brain endothelial marker proteins to identify brain endothelial cells or to identify a tumor. For instance, the vessels in tumors are often tortuous and dilated compared to normal vessels. In an example, organ-specific vessel markers can be used to detect tumors in a particular organ such as the liver or brain.

Administration

Methods of administration of the disclosed compositions are routine, and can be determined by a skilled clinician. For example, the disclosed therapies (such as those that include a binding agent specific for one or more of the disclosed pathological angiogenesis marker proteins listed in Table 9 or the organ-specific markers listed in Table 8) can be administered via injection, intratumorally, orally, topically, transdermally, parenterally, or via inhalation or spray. In a particular example, a composition is administered intravenously to a mammalian subject, such as a human.

The therapeutically effective amount of the agents administered can vary depending upon the desired effects and the subject to be treated. In one example, the method includes daily administration of at least 1 µg of the composition to the subject (such as a human subject). For example, a human can be administered at least 1 µg or at least 1 mg of the composition daily, such as 10 µg to 100 µg daily, 100 µg to 1000 µg daily, for example 10 µg daily, 100 µg daily, or 1000 µg daily. In one example, the subject is administered at least 1 µg (such as 1-100 µg) intravenously of the composition including a binding agent that specifically binds to one or more of the disclosed organ-specific or pathological angiogenesis marker proteins. In one example, the subject is administered at least 1 mg intramuscularly (for example in an extremity) of such composition. The dosage can be administered in divided doses (such as 2, 3, or 4 divided doses per day), or in a single dosage daily.

In particular examples, the subject is administered the therapeutic composition that includes a binding agent specific for one or more of the disclosed organ-specific or pathological angiogenesis marker proteins on a multiple daily dosing schedule, such as at least two consecutive days, 10 consecutive days, and so forth, for example for a period of weeks, months, or years. In one example, the subject is administered the therapeutic composition that a binding agent specific for one or more of the disclosed organ-specific or pathological angiogenesis marker proteins daily for a period of at least 30 days, such as at least 2 months, at least 4 months, at least 6 months, at least 12 months, at least 24 months, or at least 36 months.

The therapeutic compositions, such as those that include a binding agent specific for one or more of the disclosed pathological angiogenesis or organ-specific marker proteins, can further include one or more biologically active or inactive compounds (or both), such as anti-neoplastic agents and conventional non-toxic pharmaceutically acceptable carriers, respectively.

In a particular example, a therapeutic composition that includes a therapeutically effective amount of a binding agent specific for one or more of the disclosed pathological angiogenesis or organ-specific marker proteins further includes one or more biologically inactive compounds. Examples of such biologically inactive compounds include, but are not limited to: carriers, thickeners, diluents, buffers, preservatives, and carriers. The pharmaceutically acceptable carriers useful for these formulations are conventional (see Remington's Pharmaceutical Sciences, by E. W. Martin, Mack Publishing Co., Easton, Pa., 19th Edition (1995)). In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can include minor amounts of non-toxic auxiliary substances, such as wetting or emulsifying agents, preservatives, and pH buffering agents and the like, for example sodium acetate or sorbitan monolaurate.

Additional Treatments

In particular examples, prior to, during, or following administration of a therapeutic amount of an agent that reduces or inhibits pathological angiogenesis due to the interaction of a binding agent with one or more of the disclosed pathological angiogenesis marker proteins, the subject can receive one or more other therapies. In one example, the subject receives one or more treatments to remove or reduce the tumor prior to administration of a therapeutic amount of a composition including a binding agent specific for one or more of the disclosed pathological angiogenesis marker proteins.

Examples of such therapies include, but are not limited to, surgical treatment for removal or reduction of the tumor (such as surgical resection, cryotherapy, or chemoembolization), as well as anti-tumor pharmaceutical treatments which can include radiotherapeutic agents, anti-neoplastic chemotherapeutic agents, antibiotics, alkylating agents and antioxidants, kinase inhibitors, and other agents. Particular examples of additional therapeutic agents can that can be used include microtubule binding agents, DNA intercalators or cross-linkers, DNA synthesis inhibitors, DNA and/or RNA transcription inhibitors, antibodies, enzymes, enzyme inhibitors, and gene regulators. These agents (which are administered at a therapeutically effective amount) and treatments can be used alone or in combination. Methods and therapeutic dosages of such agents are known to those skilled in the art, and can be determined by a skilled clinician.

"Microtubule binding agent" refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

Suitable DNA and/or RNA transcription regulators, including, without limitation, actinomycin D, daunorubicin, doxorubicin and derivatives and analogs thereof also are suitable for use in combination with the disclosed therapies.

DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof.

DNA synthesis inhibitors suitable for use as therapeutic agents include, without limitation, methotrexate, 5-fluoro-5'-deoxyuridine, 5-fluorouracil and analogs thereof.

Examples of suitable enzyme inhibitors include, without limitation, camptothecin, etoposide, formestane, trichostatin and derivatives and analogs thereof.

Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

Kinase inhibitors include Gleevac, Iressa, and Tarceva that prevent phosphorylation and activation of growth factors.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogs thereof.

In one example, the therapeutic composition (such as one including a binding agent specific for one or more of the disclosed pathological angiogenesis marker proteins) is injected into the subject in the presence of an adjuvant. An adjuvant is an agent that when used in combination with an immunogenic agent augments or otherwise alters or modifies a resultant immune response. In some examples, an adjuvant increases the titer of antibodies induced in a subject by the immunogenic agent. In one example, the one or more peptides are administered to the subject as an emulsion with IFA and sterile water for injection (for example an intravenous or intramuscular injection). Incomplete Freund's Adjuvant (Seppic, Inc.) can be used as the Freund's Incomplete Adjuvant (IFA) (Fairfield, N.J.). In some examples, IFA is provided in 3 ml of a mineral oil solution based on mannide oleate (Montanide ISA-51). At the time of injection, the peptide(s) is mixed with the Montanide ISA.51 and then administered to the subject. Other adjuvants can be used, for example, Freund's complete adjuvant, B30-MDP, LA-15-PH, montanide, saponin, aluminum hydroxide, alum, lipids, keyhole lympet protein, hemocyanin, a mycobacterial antigen, and combinations thereof.

In some examples, the subject receiving the therapeutic peptide composition (such as one including a binding agent specific for one or more of the disclosed pathological angiogenesis marker proteins) is also administered interleukin-2 (IL-2), for example via intravenous administration. In particular examples, IL-2 (Chiron Corp., Emeryville, Calif.) is administered at a dose of at least 500,000 IU/kg as an intravenous bolus over a 15 minute period every eight hours beginning on the day after administration of the peptides and continuing for up to 5 days. Doses can be skipped depending on subject tolerance.

In some examples, the disclosed compositions can be co-administered with a fully human antibody to cytotoxic T-lymphocyte antigen-4 (anti-CTLA-4). In some example subjects receive at least 1 mg/kg anti-CTLA-4 (such as 3 mg/kg every 3 weeks or 3 mg/kg as the initial dose with subsequent doses reduced to 1 mg/kg every 3 weeks).

In one example, at least a portion of the tumor (such as a metastatic tumor) is surgically removed (for example via cryotherapy), irradiated, chemically treated (for example via chemoembolization) or combinations thereof, prior to administration of the disclosed therapies (such as administration of a binding agent specific for one or more of the disclosed pathological angiogenesis marker proteins). For example, a subject having a metastatic tumor can have all or part of the tumor surgically excised prior to administration of the disclosed therapies (such as one including a binding agent specific for one or more of the disclosed pathological angiogenesis marker proteins). In another particular example, the subject has a metastatic tumor and is administered radiation therapy, chemoembolization therapy, or both, prior to administration of the disclosed therapies (such as one including a binding agent specific for one or more of the disclosed pathological angiogenesis marker proteins).

In another example, the disclosed pathological angiogenesis marker proteins can be used as "surrogate" markers of angiogenesis that can also be used to detect the efficacy of other previously disclosed anti-angiogenic agents in clinical trials.

Screening Subjects for Pathological Angiogenesis

Subjects can be screened prior to initiating the disclosed therapies, for example to determine whether the subject has pathological angiogenesis, a tumor, or a combination thereof. For example, the presence of one or more of the disclosed pathological angiogenesis marker proteins listed in Table 9 can indicate that the subject has pathological angiogenesis and the tumor associated with the angiogenesis can be treated using the methods provided herein. In one example, the pathological angiogenesis marker proteins are detected in a serum sample, such as pathological angiogenesis markers known to be secreted (e.g., Apelin, sCD137 and plgf), or cell surface molecules that are susceptible to enzymatic cleavage at the cell surface (e.g., CD276, MiRP2, Doppel, PTPRN, CD109 or ankylosis). In another example, the proteins are detected in a tumor biopsy. Thus, the presence of the respective pathological angiogenesis marker proteins can be used to diagnose, or determine the prognosis of, a tumor in a subject.

In one example, pathological angiogenesis can be screened for by detecting at least one expression product including one or more of: Vscp, CD276, ETSvg4 (Pea3), CD137(4-1BB), MiRP2, Ubiquitin D (Fat10), Doppel (prion-PLP), Apelin, Plgf, Ptprn (IA-2), CD109, Ankylosis, and collagen VIII, 1, in a sample obtained from the subject. In some examples, detection of the at least one expression product indicates pathological angiogenesis in the subject. In a further example, detection of the at least one expression product indicates the presence of a tumor, such as cancer. For example, the biological sample can be incubated with an antibody that specifically binds to one or more of the disclosed pathological angiogenesis marker proteins. The primary antibody can include a detectable label. For example, the primary antibody can be directly labeled, or the sample can be subsequently incubated with a secondary antibody that is labeled (for example with a fluorescent label). The label can then be detected, for example by microscopy, ELISA, flow cytometery, or spectrophotometry. In another example, the biological sample is analyzed by Western blotting for the presence of at least one of the disclosed pathological angiogenesis marker proteins (see Table 9). In some examples, the level of expression of at least one of the disclosed angiogenesis marker proteins can be compared to the level of expression of such proteins in a control (e.g., non-cancer sample) or reference value.

In one example, the antibody that specifically binds an endothelial marker (such as those listed in Table 9) is directly labeled with a detectable label. In another example, each antibody that specifically binds an endothelial marker (the first antibody) is unlabeled and a second antibody or other molecule that can bind the human antibody that specifically binds the respective endothelial marker is labeled. As is well known to one of skill in the art, a second antibody is chosen that is able to specifically bind the specific species and class of the first antibody. For example, if the first antibody is a human IgG, then the secondary antibody can be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium, and non-limiting exemplary radioactive labels include $^{125}$I, $^{131}$I, $^{35}$S or $^{3}$H.

In an alternative example, endothelial markers can be assayed in a biological sample by a competition immunoassay utilizing endothelial marker standards labeled with a detectable substance and an unlabeled antibody that specifically binds the desired endothelial marker. In this assay, the biological sample (such as serum), the labeled endothelial marker standards and the antibody that specifically binds the desired endothelial marker are combined and the amount of labeled endothelial marker standard bound to the unlabeled antibody is determined. The amount of endothelial marker in the biological sample is inversely proportional to the amount of labeled endothelial marker standard bound to the antibody that specifically binds the endothelial marker.

In one example, a subject is screened by determining whether that have increased levels of one or more of the disclosed pathological angiogenesis marker proteins in their serum (for example relative to a level present in a serum sample from a subject not having a tumor), for example using an antibody that specifically binds one or more of the disclosed pathological angiogenesis markers (such as those described below).

As an alternative to analyzing the sample for the presence of proteins, the presence of nucleic acids can be determined. For example, the biological sample can be incubated with primers that permit the amplification of one or more of the pathological angiogenesis marker mRNAs, under conditions sufficient to permit amplification of such products (see, for example, primer sequences provided in Example 1). Exemplary methods include SAGE and PCR. In another example, the biological sample is incubated with probes that can bind to one or more of the disclosed pathological angiogenesis marker nucleic acid sequences (such as cDNA, genomic DNA, or RNA (such as mRNA)) under high stringency conditions. The resulting hybridization products can then be detected using methods known in the art. In one example, a subject is screened by determining whether that have increased levels of one or more the disclosed pathological angiogenesis marker nucleic acids in their serum (for example relative to a level present in adjacent non-tumor cells from the same subject), for example detecting mRNA expression of one or more the disclosed pathological angiogenesis markers.

Generation of Antibodies

One of ordinary skill in the art can readily generate antibodies which specifically bind to the disclosed endothelial marker proteins. These antibodies can be monoclonal or polyclonal. They can be chimeric or humanized. Any functional fragment or derivative of an antibody can be used including Fab, Fab', Fab2, Fab'2, and single chain variable regions. So long as the fragment or derivative retains specificity of binding for the endothelial marker protein it can be used in the methods provided herein. Antibodies can be tested for specificity of binding by comparing binding to appropriate antigen to binding to irrelevant antigen or antigen mixture under a given set of conditions. If the antibody binds to appropriate antigen at least 2, at least 5, at least 7 or 10 times more than to irrelevant antigen or antigen mixture, then it is considered to be specific.

In an example, monoclonal antibodies are generated to the endothelial cell markers disclosed in Tables 8 and 9. These monoclonal antibodies each include a variable heavy ($V_H$) and a variable light ($V_L$) chain and specifically bind to the specific endothelial cell markers. For example, the antibody can bind the specific endothelial cell markers with an affinity constant of at least $10^6$ $M^{-1}$, such as at least $10^7$ $M^{-1}$, at least $10^8$ $M^{-1}$, at least $5 \times 10^8$ $M^{-1}$, or at least $10^9$ $M^{-1}$.

The specific antibodies can include a $V_L$ polypeptide having amino acid sequences of the complementarity determining regions (CDRs) that are at least about 90% identical, such as at least about 95%, at least about 98%, or at least about 99% identical to the amino acid sequences of the specific endothelial marker proteins and a $V_H$ polypeptide having amino acid sequences of the CDRs that are at least about 90% identical, such as at least about 95%, at least about 98%, or at least about 99% identical to the amino acid sequences of the specific endothelial marker proteins.

In one example, the sequence of the specificity determining regions of each CDR is determined. Residues that are outside the SDR (non-ligand contacting sites) are substituted. For example, in any of the CDR sequences, at most one, two or three amino acids can be substituted. The production of chimeric antibodies, which include a framework region from one antibody and the CDRs from a different antibody, is well known in the art. For example, humanized antibodies can be routinely produced. The antibody or antibody fragment can be a humanized immunoglobulin having CDRs from a donor monoclonal antibody that binds one of the disclosed endothelial marker proteins and immunoglobulin and heavy and light chain variable region frameworks from human acceptor immunoglobulin heavy and light chain frameworks. Generally, the humanized immunoglobulin specifically binds to one of the disclosed endothelial marker proteins with an affinity constant of at least $10^7$ $M^{-1}$, such as at least $10^8$ $M^{-1}$ at least $5 \times 10^8$ $M^{-1}$ or at least $10^9$ $M^{-1}$.

In another example, human monoclonal antibodies to the disclosed specific endothelial marker proteins in Tables 8 and 9 are produced. Human monoclonal antibodies can be produced by transferring donor complementarity determining regions (CDRs) from heavy and light variable chains of the donor mouse immunoglobulin into a human variable domain, and then substituting human residues in the framework regions when required to retain affinity. The use of antibody components derived from humanized monoclonal antibodies obviates potential problems associated with the immunogenicity of the constant regions of the donor antibody. For example, when mouse monoclonal antibodies are used therapeutically, the development of human anti-mouse antibodies (HAMA) leads to clearance of the murine monoclonal antibodies and other possible adverse events. Chimeric monoclonal antibodies, with human constant regions, humanized monoclonal antibodies, retaining only murine CDRs, and "fully human" monoclonal antibodies made from phage libraries or transgenic mice have all been used to reduce or eliminate the murine content of therapeutic monoclonal antibodies.

Techniques for producing humanized monoclonal antibodies are described, for example, by Jones et al., Nature 321: 522, 1986; Riechmann et al., Nature 332:323, 1988; Verhoeyen et al., Science 239:1534, 1988; Carter et al., Proc. Natl. Acad. Sci. U.S.A. 89:4285, 1992; Sandhu, Crit. Rev. Biotech. 12:437, 1992; and Singer et al., J. Immunol. 150:2844, 1993. The antibody may be of any isotype, but in several embodiments the antibody is an IgG, including but not limited to, $IgG_1$, $IgG_2$, $IgG_3$ and $IgG_4$.

In one example, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in a humanized antibody framework regions, are known in the art (see, for example, in U.S. Pat. No. 5,585,089).

Antibodies, such as murine monoclonal antibodies, chimeric antibodies, and humanized antibodies, include full length molecules as well as fragments thereof, such as Fab, $F(ab')_2$, and Fv, which include a heavy chain and light chain variable region and are capable of binding the epitopic determinant. These antibody fragments retain some ability to selectively bind with their antigen or receptor. These fragments include: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) $(Fab')_2$, the fragment of the antibody that can be obtained by treating whole antibody with the enzyme pepsin without subsequent reduction; $F(ab')_2$ is a dimer of two Fab' fragments held together by two disulfide bonds; (4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule. Methods of making these fragments are known in the art (see for example, Harlow and Lane, Antibodies: A Laboratory Manual, Cold Spring Harbor Laboratory, New York, 1988). Fv antibodies are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments include $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Antibodies are commercially available for many of the endothelial markers disclosed herein (see Tables 1-4).

TABLE 1

Antibodies for Brain Endothelial Markers (BEMs)

| Gene Accession No. | Gene | Commercial Source |
|---|---|---|
| NM_011400 | Glucose transporter GLUT-1 | abcam ® |
| NM_030687 | Organic anion transporter 2 | Alpha Diagnostic International |
| NM_008973 | Pleiotrophin | abcam ® |
| NM_009728 | ATPase, class V, type 10A | Orbigen |
| NM_009402 | Peptidoglycan recognition protein 1 | IMGENEX |
| NM_008239 | Forkhead box Q1 | abcam ® |
| NM_031194 | Organic anion transporter 3 | Alpha Diagnostic International |
| NM_172479 | SN2, Solute carrier family 38, member 5 | abcam ® |
| NM_010703 | Lymphoid enhancer binding factor 1 | Aviva Systems Biology |
| NM_011404 | Solute carrier family 7, member 5 | BIODESIGN International |
| NM_023805 | Solute carrier family 38, member 3 | BD Biosciences Pharmingen |
| NM_009574 | Zinc finger protein of the cerebellum 2 | BIODESIGN International |
| NM_052994 | Testican-2 | R & D Systems |
| NM_028748 | Progestin and adipoQ receptor family member V | Abnova Corporation |
| NM_010357 | Glutathione S-transferase, alpha 4 | Lab Vision |
| NM_011532 | T-box 1 | BioCarta |

TABLE 2

Antibodies for Liver Endothelial Markers (LEMs)

| Gene Accession No. | Gene | Commercial Source |
|---|---|---|
| NM_007870 | Deoxyribonuclease 1-like 3 | Abnova ® Corporation |
| AK150613 | CD32 15 | Eurogenetics |
| NM_019985 | C-type lectin-like receptor 2 | R & D Systems |
| NM_018797 | Plexin C1 | Novus Biologicals |
| NM_008092 | GATA-binding protein 4 | CeMines |
| AB049755 | MBL-associated serine protease-3 | HyCult biotechnology b.v. |

TABLE 2-continued

Antibodies for Liver Endothelial Markers (LEMs)

| Gene Accession No. | Gene | Commercial Source |
|---|---|---|
| NM_023132 | Renin binding protein | Novus Biologicals |
| NM_011243 | Retinoic acid receptor, beta | abcam ® |

TABLE 3

Antibodies for Physiological Angiogenesis Endothelial Markers

| Gene Accession No. | Gene | Commercial Source |
|---|---|---|
| NM_026785 | Ube2c | Novus biologicals |
| NM_011623 | DNA topo II | Leinco Technologies, Inc. |
| NM_008381 | Inhibin beta-B | AbDSerotec |
| NM_025415 | Cks2 | Novus biologicals |
| NM_009387 | TK1 | Novus biologicals |
| NM_011607 | Tenascin C | abcam ® |
| NM_024435 | Neurotensin | Calbiochem |
| NM_145150 | Prc1 | Biolegend |
| XM_133912 | Ki67 antigen | abcam ® |
| NM_016780 | beta-Integrin | ABR - Affinity BioReagents |

TABLE 4

Antibodies for Pathological Angiogenesis Endothelial Markers

| Gene Accession No. | Gene | Commercial Source |
|---|---|---|
| DQ832276 | CD276 (B7-H3) | eBioscience, Inc. |
| DQ832277 | ETSvg4 (Pea3) | Santa Cruz Biotechnology |
| DQ832278| | CD137 (4-1BB) | GeneTex |
| DQ832280 | MiRP2 | almone labs |
| NM_023137 | Ubiquitin D (FAT10) | R & D Systems |
| DQ832281 | Doppel (Prion-PLP) | abcam ® |
| DQ832282 | Apelin | ABR-Affinity BioReagents |
| NM_008827 | Plgf | R & D Systems |
| DQ832283 | Ptprn (IA-2) | abcam ® |
| DQ832284 | CD109 | abcam ® |
| NM_007739 | Coll. VIII, α1 | Cosmo Bio Corp., Ltd. |

Conjugation of Therapeutic or Diagnostic Agents to Antibodies

Binding agents, such as antibodies of this disclosure, can be conjugated or linked to an effector molecule, such as a therapeutic agent (such as an anti-tumor agent) or a diagnostic agent (such as a fluorescent moiety), using any number of methods known to those of skill in the art (for example, see Harlow and Lane, *Using Antibodies: A Laboratory Manual*, CSHL, New York, 1999; Yang et al., Nature, 382:319-24, 1996). Both covalent and noncovalent attachment means can be used.

The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization can involve attachment of any of a number of linker molecules such as those available from Pierce Chemical Company, Rockford, Ill. The linker can be any molecule used to join the antibody to the effector molecule (e.g., therapeutic agent or diagnostic agent). The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers can be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates can include linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (for example, when exposed to tumor-associated enzymes or acidic pH) can be used.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The subject matter of the present disclosure is further illustrated by the following non-limiting Examples.

EXAMPLES

Example 1

Materials and Methods

Cell lines and animal studies. EMT6 cells were a kind gift of Dr. Robert S. Kerbel, KM12SM cells were a kind gift of Isaiah J. Fidler, HCT116 cells were from the DCT tumor repository (NCI, Frederick) and LS174T, SW620, CT26 and LLC were from the American Type Culture Collection (Manassas, Va.). Tumor cell lines were maintained in DMEM containing 10% fetal bovine serum. Tumors were made by inoculating $5 \times 10^5$-$1 \times 10^6$ cells subcutaneously or intrasplenically. To produce liver metastasis by intrasplenic injection, the spleen was exteriorized through a left lateral incision prior to tumor cell injection. The tumor cell suspension was allowed to enter the portal circulation over a period of five minutes, after which the spleen was removed and the skin sutured. For partial hepatectomy, the liver was exposed through a midline abdominal incision and the two anterior lobes were exteriorized and the suspensory ligaments severed. The left lateral and caudal lobes were gently tied off using 6-0 sterile silk prior to excision leaving a 3 mm stump above the silk. The procedure results in the removal of ~70% of liver volume. The remaining liver was placed back into the peritoneal cavity and the peritoneal cavity and skin are sutured.

Endothelial cell isolations and construction of SAGE libraries. Immediately following CO$_2$ euthanasia, normal or tumor tissues were resected, diced with a razor, and digested in Hepatocyte Wash Buffer (Invitrogen, Carlsbad, Calif.) containing 2 mg/ml collagenase A (Roche) for 1-hour at 37° C. All subsequent steps were performed on ice or at 4° C. After filtering sequentially through 100 and 25-μm mesh, cells were pelleted and rinsed repeatedly with PBS containing 0.5% BSA (PBS/BSA) until the supernatant was transparent. To remove hematopoietic cells from the sample, cells were incubated with a mixture of streptavidin-linked dynabeads (Dynal, Lake Success, N.Y.) that had been separately pre-bound to biotin anti-CD19, biotin anti-CD45 (BD Pharmingen, San Diego, Calif.) or biotin anti-F480 (Caltag Laboratories, Burlingame, Calif.) and then mixed at a 1:1:1 ratio. To prevent non-specific binding of Fc-receptor containing cells in the positive selection, anti-CD16/32 antibodies (Fc Block; BD Pharmingen) were added to the cell suspension. To label ECs from heart, kidney, intestine, liver, lung, KM12 tumors and LS174T tumors, biotinylated rat anti-mouse CD105 (eBioscience, San Diego, Calif.) was added; to label ECs from spleen, CT26 tumors or LLC tumors biotinylated goat anti-mouse VE-cadherin (R&D Systems, Minneapolis, Minn.) was added, and to label ECs from brain, muscle, EMT6 tumors and SW620 a mixture of both antibodies was added. After rinsing 5× with PBS/BSA, streptavidin-linked dynabeads were added to the cell suspension, rotated 5 minutes at 4° C., diluted to 40 ml with PBS/BSA and bead-bound cells were captured using a Dynal MPC-50 magnet. Captured ECs were rinsed 5-10 times until only bead-bound cells were observed. Cells were resuspended in mRNA lysis/binding buffer for SAGE or mRNA extraction buffer for RT-PCR. After removing the beads, lysates were stored at −80° C. until ready to use.

Construction of SAGE libraries. LongSAGE libraries were constructed using the I-SAGE Long Kit (Invitrogen) and a previously established MicroSAGE protocol by St. Croix et al. (available from John Hopkins Oncology Center, Baltimore, Md. 21231) which is herein incorporated by reference in its entirety. Ditags were PCR amplified using biotinylated primers to facilitate efficient linker removal and Mme-I enzyme was purchased from New England Biolabs (Ipswich, Mass.). SAGE tags used to identify various endothelial cell markers are included in Tables 5A-5D. Some genes have multiple tags due to alternative polyadenylation sites, internal polyA stretches, and antisense transcripts. The number of times each tag was observed was normalized to 100,000 tags and is indicated in parenthesis following the tag sequence in Tables 5A-5D. For genes with multiple SAGE tags, counts for individual tags were summed to obtain the total number of tags. Each tag is preceded by the sequence CATG. Antisense tags are followed by an asterisk.

TABLE 5A

SAGE tags used to identify Brain Endothelial Markers.

| SEQ ID NO: | Acc # | SAGE Tags |
|---|---|---|
| 1 | NM_011400 | AGAAGGACCTCGGAGGC (512) |
| 2 | NM_011400 | TGCTTCCAGTATGTGGA (124) |
| 3 | NM_011400 | GTGTTTGTGTGGCCCTC* (104) |
| 4 | NM_011400 | AGAAGGACTTCGGAGGC (8) |
| 5 | NM_011400 | CCTGAATTGCTGAGGCC (5) |
| 6 | NM_030687 | AGGGACTTCAGTCCCTC (137) |
| 7 | NM_030687 | ATAAAAATATTTACTG (11) |
| 8 | NM_030687 | CCCCACCAAAAATCAAT (9) |
| 9 | NM_008973 | AAATCCTTTCACTTTGG (72) |
| 10 | NM_008973 | TAAACTACTTCTCTTGT (15) |
| 11 | NM_008973 | TTTCAATCTTATCTTAA (7) |
| 12 | NM_009728 | GGTCTGACAGCTCCGGT (32) |
| 13 | NM_009402 | GACCGGGTACCCGCAAA (40) |
| 14 | NM_021471 | ACAAACCTCTAAGGATG (15) |
| 15 | NM_021471 | CGCTGCAAGGGATCGTG (7) |
| 16 | NM_021471 | TAAATGAATAAAAGCAT (4) |
| 17 | NM_008239 | GGGTAAATGATGACTAC (15) |
| 18 | NM_008239 | GGCAAGTTCCCCTTTTT (9) |
| 19 | NM_008239 | GAGTGGTTCCCTGATGT* (5) |
| 20 | NM_031194 | CTCTCAGAACAAAGACT (14) |
| 21 | NM_031194 | CCAACCTACTCTATTGC (5) |
| 22 | NM_172479 | AGAGGAGGTATGGGAGG |
| 23 | NM_172471 | AGGAGAGTGTCTAAAAG (24) |
| 24 | NM_172471 | CACAAATATTTACCATT (13) |
| 25 | NM_172471 | AGTTTCCACCTTTATTC (4) |
| 26 | NM_010703 | GTGGTAAGAGAAGCTCC (12) |
| 27 | NM_011404 | TCACTGCCCTGAAAGAC (23) |
| 28 | NM_023805 | ACTTACATTCCACTGCT (20) |
| 29 | NM_009574 | TGATGTTTCAGTGCTTT (8) |
| 30 | NM_009574 | AGTCCTCCCCTCAGGGC (6) |
| 31 | NM_009574 | CTTCCTAGTCTTTTTGA (2) |
| 32 | NM_052994 | TTTTAGTAAGAAAGCAG (49) |
| 33 | NM_052994 | CCTCAGCACGCCCTCAG (27) |
| 34 | NM_052994 | GGACCCCTGACTGTGAT (4) |
| 35 | NM_008256 | CTGCTGTGGACCAGAGC (19) |
| 36 | NM_008256 | AATGTGTTCTATCCCTC (7) |
| 37 | NM_028748 | ACTTCAGAATGTGCCAG (7) |
| 38 | NM_028748 | GTGGATGCCAATTTGCC (5) |
| 39 | NM_028748 | ATACCAAACACGCCAAT (3) |
| 40 | AK172004 | GTGCATACTTGAGGGGG (68) |
| 41 | NM_001042671 | ACTTTAATACCACTTAG* (6) |
| 42 | NM_001042671 | CAGAAAATAAATGTCC (4) |
| 43 | NM_001042671 | TATTGACAGAAGTTAAA (4) |
| 44 | NM_029001 | CACAAGCTGTTAGAGGC (11) |
| 45 | NM_029001 | CTTACAATGAGAAGCGA (6) |
| 46 | NM_029001 | GGCGCCACACAACGTTG (4) |

TABLE 5A-continued

SAGE tags used to identify Brain Endothelial Markers.

| SEQ ID NO: | Acc # | SAGE Tags |
|---|---|---|
| 47 | NM_029001 | TCCTGCCATTCACAAAT (3) |
| 48 | NM_029001 | TGATTGGCTTACCTCAG (2) |
| 49 | NM_027299 | GAACACCACGACTTCCC (19) |
| 50 | XM_486083 | CGGAAACTGCCAGTGCT (37) |
| 51 | XM_486083 | CGGAAACTGCCAAAAAA (2) |
| 52 | NM_017405 | GGAGCAGGAACCCCTTC (46) |
| 53 | NM_010357 | TATGCAGATGGCACCCA (36) |
| 54 | NM_013869 | GCTCTTAAGAGAGTTTG (9) |
| 55 | NM_011532 | CGGGTTTCCCGCCCGCC (17) |
| 56 | XM_620023 | CAACGCCAGCCTCTCCC (6) |

TABLE 5B

SAGE tags used to identify Liver Endothelial Markers.

| SEQ ID NO: | Acc # | SAGE Tags |
|---|---|---|
| 57 | NM_007870 | TGTAACCTGAAGAAATA (122) |
| 58 | NM_007870 | CAGATAGCTTAGACCTA* (38) |
| 59 | NM_007870 | GGTGATTTCAACGCCGG (16) |
| 60 | NM_007870 | GTGCTTGCTTGTGTGCA* (15) |
| 61 | NM_007870 | CCAAATCTGTCCTGTTG* (6) |
| 62 | NM_010959 | CAGGCAAACCACTCATA (28) |
| 63 | NM_010959 | ATCTCCTAGATACCTAA (26) |
| 64 | NM_010959 | AAAGGACTGGCTGGCTG (5) |
| 65 | NM_023438 | GGGTGGGTGAAGGCAGA (16) |
| 66 | AK150613 | TTACTTTAATAGTAAAA (66) |
| 67 | AK150613 | GTACAGTGTAGATAATT (32) |
| 68 | AK150613 | TATAGGCTTTCTAAAAA* (6) |
| 69 | AK150613 | AGTTCAGAGTGTAGACA (5) |
| 70 | AK150613 | TGTGTGGGCTGCCTATG* (5) |
| 71 | AK150613 | ATTACCAGAACCACATT (5) |
| 72 | AK150613 | CGAAGGGACCCACAACC (4) |
| 73 | NM_033616 | GGTCTTACCTCACCACG (22) |
| 74 | NM_033616 | TTGCTTGGAACCGCATT* (5) |
| 75 | NM_019985 | CAATAAAAGATCTGGAC (14) |
| 76 | NM_029465 | CTTTAGTGACCCCAGCT (219) |
| 77 | NM_029465 | ATGGTGGGCACTGCTCA* (14) |
| 78 | NM_029465 | TCCTCTGGAATCATTGG (6) |

TABLE 5B-continued

SAGE tags used to identify Liver Endothelial Markers.

| SEQ ID NO: | Acc # | SAGE Tags |
|---|---|---|
| 79 | NM_018797 | AGTCCTGTGTGAGCCTT (23) |
| 80 | NM_029465 | ATGGTGGGCACTGCTCA* (14) |
| 81 | NM_029465 | TCCTCTGGAATCATTGG (6) |
| 82 | NM_011719 | CTTCCTGTCTGAGCACT (9) |
| 83 | AK144596 | GGGTTGTAAGGAATTTT (16) |
| 84 | NM_008092 | CCTGCCCCTCCTCCACA (7) |
| 85 | NM_008092 | ATAGCAGCTGTCCTAGG (2) |
| 86 | AB049755 | TAAAGGATACTATATTT (6) |
| 87 | AB049755 | AGTCCTGGGTTCTGTCC (4) |
| 88 | NM_023132 | AAGGCTCGAAATAAAGA (5) |
| 89 | NM_144830 | GATGAATCTTTTTCAAG (14) |
| 90 | NM_144830 | GATTCTCTGCATCAGGC (7) |
| 91 | NM_144830 | TTGGTTACCCAGCTCCG (5) |
| 92 | NM_011243 | GAGTCTCCTGGCAAAGA (10) |
| 93 | NM_011243 | AATAACCAGGCCTCACG (1) |

TABLE 5C

SAGE tags used to identify Physiological Angiogenesis Endothelial Markers.

| Gene (SEQ ID NO) | SAGE tags |
|---|---|
| Ube2c (SEQ ID NO: 94) | ACATCTGGTGACAAAGG (47) |
| Ube2c (SEQ ID NO: 95) | GGTATCTGCTGGACAGG (5) |
| TRAF4af1 (SEQ ID NO: 96) | CTGTCCCCTTGTCTCTC (31) |
| TRAF4af1 (SEQ ID NO: 97) | GAGCTGTCTTATGTGTC (2) |
| TRAF4af1 (SEQ ID NO: 98) | TTTCCGAGTCTCTAGAG* (1) |
| TRAF4af1 (SEQ ID NO: 99) | TTTCCGAGTCTCTAGAG* (1) |
| DNA topo II alpha (SEQ ID NO: 100) | AGAAGTTGCTCGTACCT (60) |
| DNA topo II alpha (SEQ ID NO: 101) | CCCCTGTGGTATCTGAC (7) |
| DNA topo II alpha (SEQ ID NO: 102) | GAGTTGTCACCGCTGCA (5) |
| DNA topo II alpha (SEQ ID NO: 103) | TTACAGAGAGCAAAGCT (4) |
| DNA topo II alpha (SEQ ID NO: 104) | TAGGTTGCTTAAAGAAA (3) |

TABLE 5C-continued

SAGE tags used to identify Physiological Angiogenesis Endothelial Markers.

| Gene (SEQ ID NO) | SAGE tags |
| --- | --- |
| DNA topo II alpha (SEQ ID NO: 105) | ACCAAAAAGCAAGTTGG (2) |
| DNA topo II alpha (SEQ ID NO: 106) | GGCAATTGTCTTCTCTG (1) |
| DNA topo II alpha (SEQ ID NO: 107) | GCTTAAACAAAATGCAT (1) |
| Ckap2 (SEQ ID NO: 108) | CCTAAGTATGGTACAGG (25) |
| Inhibin beta-B (SEQ ID NO: 109) | GTTAGTCAGAAACTGCC (98) |
| Inhibin beta-B (SEQ ID NO: 110) | TACAGTATAAGACAATA (22) |
| Inhibin beta-B (SEQ ID NO: 111) | AACGTAAAATACTTAAG (20) |
| Inhibin beta-B (SEQ ID NO: 112) | GGTCTTTGAGGGAGCAG (4) |
| Inhibin beta-B (SEQ ID NO: 113) | TCCCCTGCCCAGTTCAC (4) |
| Inhibin beta-B (SEQ ID NO: 114) | CTTTGAGGCCAGCAGAG (1) |
| Cks2 (SEQ ID NO: 115) | CGCTGTATTCTTCACAG (41) |
| Thymidine kinase 1 (SEQ ID NO: 116) | GAGTGCTTCCGAGAAGC (66) |
| Tenascin C (SEQ ID NO: 117) | GTCATTCTCCGAGCCAG (76) |
| Tenascin C (SEQ ID NO: 118) | GTGTTGCTGTCACTAGG* (3) |
| Tenascin C (SEQ ID NO: 119) | AGTACTCAATCCAGTTT (1) |
| Neurotensin (SEQ ID NO: 120) | TAAATTGGATGCAATGT (22) |
| Neurotensin (SEQ ID NO: 121) | GATATTTTGCCTGTCAA (13) |
| Neurotensin (SEQ ID NO: 122) | ATGACGACCTTGTTGGC (2) |
| Prc1 (SEQ ID NO: 123) | GAGTCAGCAACTTTGCA (38) |
| Prc1 (SEQ ID NO: 124) | AAGTAATTCTGGTAACA (1) |
| Prc1 (SEQ ID NO: 125) | ATGCCGAGATTGTACGG (1) |
| Ki67 antigen (SEQ ID NO: 126) | AGGAAGATCACCAGGGA (48) |
| Ki67 antigen (SEQ ID NO: 127) | CTAATGGCCCATTAGTG (4) |
| Ki67 antigen (SEQ ID NO: 128) | AAGGAAGAAAGCTCTGC (2) |
| Ki67 antigen (SEQ ID NO: 129) | CTTGAGGTCTAGAGGAA (2) |
| Ki67 antigen (SEQ ID NO: 130) | AGAGAATTTTCCATACT (1) |
| Ki67 antigen (SEQ ID NO: 131) | ATTTCCATCTTCATACC* (1) |
| Integrin beta 3 (SEQ ID NO: 132) | CTAGGCAAGAACATTAC (45) |
| Integrin beta 3 (SEQ ID NO: 133) | ACCGGAAGGAATTTGCT (6) |
| Integrin beta 3 (SEQ ID NO: 134) | ATGCCCGGCAGGTGCTC (3) |
| Integrin beta 3 (SEQ ID NO: 135) | GACTACCCATCTCTGGG (3) |
| Integrin beta 3 (SEQ ID NO: 136) | GTTTGCTCTGCTGGCAT (2) |

TABLE 5D

SAGE tags used to identify Pathological Angiogenesis Endothelial Markers.

| Gene (SEQ ID NO.) | SAGE tags |
| --- | --- |
| Vscp (SEQ ID NO: 137) | GCTCTGTGTCTATGCAG (22) |
| Vscp (SEQ ID NO: 138) | GCTCTCTTGTGTGCACT (16), |
| Vscp (SEQ ID NO: 139) | GCTGGCACTGGTAACCT (8) |
| Vscp (SEQ ID NO: 140) | GGGGAAGGCTGGTGGTC* (2) |
| Vscp (SEQ ID NO: 141) | CAGAGGGCTGGGGCCGG (1) |
| CD276 (SEQ ID NO: 142) | AGACTGTAAACTGGGTG (17) |
| CD276 (SEQ ID NO: 143) | GGACTCTGTAAACTGGG (17) |
| CD276 (SEQ ID NO: 144) | GGACTCTGGCCAGCACC (1) |

TABLE 5D-continued

SAGE tags used to identify Pathological Angiogenesis Endothelial Markers.

| Gene (SEQ ID NO.) | SAGE tags |
|---|---|
| CD276 (SEQ ID NO: 145) | GTGCTATTCTGGAGCTG (1) |
| Ets variant gene 4 (SEQ ID NO: 146) | TGGGCGGCAGCTGGGGG (27) |
| Ets variant gene 4 (SEQ ID NO: 147) | CAATGTGGGAAGTGGAG (4) |
| Ets variant gene 4 (SEQ ID NO: 148) | GGGGGTTGGGAGAGGGG (2) |
| Ets variant gene 4 (SEQ ID NO: 149) | TGGGAGGCAGCTGGGGG (2) |
| CD137 (SEQ ID NO: 150) | ACTCCTGGACAGCTCAA (29) |
| CD137 (SEQ ID NO: 151) | CATCATATTTGCACACA (4) |
| CD137 (SEQ ID NO: 152) | GGAAACAACTGTTACAA (3) |
| CD137 (SEQ ID NO: 153) | GTGGACTGGAAGGCCGC (2) |
| CD137 (SEQ ID NO: 154) | GGTCTCCCCCTTCAGAC (1) |
| MiRP2 (SEQ ID NO: 155) | AGAAACCTTGATAAAAC (84) |
| Ubiquitin D (SEQ ID NO: 156) | GCTGACTACAACATCAA (11) |
| Prion-PLP (SEQ ID NO: 157) | AAGTATTCCACAGTACA (16) |
| Prion-PLP (SEQ ID NO: 158) | AAGCAGGGCGGAACCTT (5) |
| Prion-PLP (SEQ ID NO: 159) | TGTGTTCTTAGGCATCT (2) |
| Prion-PLP (SEQ ID NO: 160) | GTCATCTAAAAGGACTA (2) |
| Prion-PLP (SEQ ID NO: 161) | TGATTTTGACTGCAAAT (1) |
| Apelin (SEQ ID NO: 162) | GTTCTATACTCTTCTGG (11) |
| Apelin (SEQ ID NO: 163) | TAAATATGTCTTTATAA (9) |
| Apelin (SEQ ID NO: 164) | TTCTTCTCAGAGGCCTC (1) |
| Placental growth factor (SEQ ID NO: 165) | TAGAGGGGACCCAGTCT (24) |
| Placental growth factor (SEQ ID NO: 166) | CCTTCAATGCAGCCGGG (3) |
| Placental growth factor (SEQ ID NO: 167) | GCCTTTCAAGGGGGCAG (1) |
| PTPRN (SEQ ID NO: 168) | GGAAGCAGACAGCAGGC (19) |
| PTPRN (SEQ ID NO: 169) | GGCCCCCTCCGGCCCCA* (1) |
| PTPRN (SEQ ID NO: 170) | TGATCTCCCAGGAGATG (1) |
| CD109 (SEQ ID NO: 171) | GCGACAGTCTCACTCTG (13) |
| CD109 (SEQ ID NO: 172) | TCTCTATATCTCCTTCT (2) |
| CD109 (SEQ ID NO: 173) | TTACCTCAGTCCAGACA (2) |
| Progressive ankylosis (SEQ ID NO: 174) | ACTAGAAAATTAAACAG (18) |
| Collagen VIII, alpha 1 (SEQ ID NO: 175) | TAAAAAAAGAGAAAAA (14) |
| Collagen VIII, alpha 1 (SEQ ID NO: 176) | TACAAATAAAAACTAAA (2) |
| Collagen VIII, alpha 1 (SEQ ID NO: 177) | ATGTACACATACGACGA (1) |
| Collagen VIII, alpha 1 (SEQ ID NO: 178) | GGATACAATAAATATCC (1) |

Quantitative PCR. mRNA was purified using the Quick Prep Micro mRNA purification kit (Amersham, Piscataway, N.J.). Single-stranded cDNA was generated using Superscript III first strand synthesis system (Invitrogen) following the manufacturer's directions. Quantitative PCR was performed with an MX4000 using Brilliant SYBR Green QPCR Master Mix and threshold cycle numbers were obtained using MX4000 software v4.20 (Stratagene, La Jolla, Calif.). Primer sets for each sequence analyzed are included in Table 5E below. Endothelial cells used in QPCR are provided in Table 5F. Antibodies against the endothelial selection markers CD105, VE-cadherin (VE-cad) or both were used in the positive selection to immunopurify the endothelial cells. Endothelial cells were derived from the host strain indicated and then used to generate cDNA for QPCR. Nude: NCr nu/nu.

TABLE 5E

Primer sets for QPCR.

| SEQ ID NO (Forward, Reverse) | Gene | Forward Primer | Reverse Primer |
|---|---|---|---|
| Normalizers | | | |
| 179, 180 | Snrp70 | CTCCTCCTCCAACAAG AGCAG | CGATGAAGGCAT AACCACG |
| 181, 182 | VE-cadherin | GCTACCTGCCCACCAT CG | CATCCACTGCTG TCACACGG |
| Brain endothelial Marker Primers | | | |
| 183, 184 | Glut-1 | ATCCCAGCAGCAAGAA GGTG | ATCATCAGCATG GAGTTCCG |
| 185, 186 | Oatp2 | TGGAACTGGAACCAAC ATGG | AGGTATGGCTCC CAGCGAG |
| Physiological Angiogenesis Marker Primers | | | |
| 187, 188 | Ube2c | GTGGGCAAGCGGCTAC AG | CGATGTTGGGTTC TCCTAGC |
| 189, 190 | TRAFaf1 | ATCGAGACGAGAGAAT GGGC | GGAGTCCGTGTG ATCTGTGG |
| 191, 192 | DNA topo II alpha | ACTGCTCCGCCCAGAT ACC | CCATAGCCATTT CGACCACC |
| 193, 194 | Ckap2 | CTCAGCCTATTGAAGA GATGCG | AGCGTCTCACTG GTGTCAGG |
| 195, 196 | Inhibin beta-B | GCGTCTCCGAGATCAT CAGC | TGACCCGTACCTT CCTCCTG |
| 197, 198 | Thymidine kinase 1 | ATCGCCCAGTACAAGT GCC | GGAAGGTCCCAT CCAGCG |
| 199, 200 | Tenascin C | TTTGGCTTGGACTGGA TAACC | TGCCCATCAGGT TGACACG |
| 201, 202 | Neurotensin | GAAGATGTGAGAGCCC TGGAG | CCTGGATTATCT CCCAGTGTTG |
| 203, 204 | Prc 1 | CTACACCCAACAGTAG CATTCG | TCCGTCAGTCCA GTCCAGG |
| 205, 206 | Ki67 antigen | CGCACACTTCCCGCTG AG | GCTCGCCTTGAT GGTTCC |
| 207, 208 | Integrin beta 3 | CGGGATGACATCGAGC AG | ACACTCAGGCTC TTCCACCAC |
| Pathophysiological Angiogenesis Marker Primers | | | |
| 209, 210 | Vscp | CCGTCATATTCGCCTG GG | TGCTGGCAGGTG CTCTAGG |
| 211, 212 | CD276 | CTTGTTCGATGTTCAC AGCG | GCCGTAGAGCTG TCTTGGATC |
| 213, 214 | Ets variant gene 4 | AACGAAGTCTCCAAAT CTGTCC | AGGTGGAATTAG GCCTGGG |
| 215, 216 | CD137 | CAGCATAGGTGGACAG CCG | CACACCACGTCC TTCTCCG |
| 217, 218 | MiRP2 | GGAGACAGATCGTAGA GGCG | GGAAGCAGCCAG AGTCGTG |

TABLE 5E-continued

Primer sets for QPCR.

| SEQ ID NO (Forward, Reverse) | Gene | Forward Primer | Reverse Primer |
|---|---|---|---|
| 219, 220 | Ubiqutin D | GTCCGCACCTGTGTTG TCC | CATCTTCCAGCTT CTTTCCG |
| 221, 222 | Prion-PLP | TAGCAGAGAACCGAGA TTCACC | GCTTCAGAGCAG CCTTCGTAG |
| 223, 224 | Apelin | AATCTGAGGCTCTGCG TGC | GCCCTTCAATCCT GCTTTAGA |
| 225, 226 | Placental growth factor | GTGCCTTGAAGGACCT TGG | AGCAGCCACTAC AGCGACTC |
| 227, 228 | PTPRN | GGTGTCGGAGCACATC TGG | TCAAACTGGTCC TTAGAACGG |
| 229, 230 | CD109 | CGGCACTACCTCTGAG CAGT | AACCTGAATGGA CCAGTCACC |
| 231, 232 | Progressive ankylosis | TCACTGGATGGCTGAT GACAC | TGTTGGAGGCAT GTCGGTC |
| 233, 234 | Collagen VIII, alpha 1 | TTCCACAGTACCAGCC CTTG | CTCCACGGGGAC CTTGTTC |

TABLE 5F

Endothelial cells for QPCR.

| | Strain | Selection Marker |
|---|---|---|
| Normal ECs | | |
| Brain | Nude | CD105 & VE-cad |
| Heart | Nude | CD105 & VE-cad |
| Kidney | Nude | CD105 |
| Spleen | Nude | VE-cad |
| Intestine | C57BL/6 | CD105 |
| Lung | Nude | CD105 |
| liver | Nude | CD105 |
| Reg. Liv. Ecs | | |
| 6 h | Nude | CD105 |
| 18 h | Nude | CD105 |
| 40 h | Nude | CD105 |
| 72 h | Nude | CD105 |
| 96 h | Nude | CD105 |
| Tumor ECs | | |
| CT26 | Balb/c | CD105 & VE-cad |
| EMT6 | Balb/c | CD105 & VE-cad |
| KM12SM | Nude | CD105 & VE-cad |
| LLC | C57BL/6 | CD105 & VE-cad |
| LS174T | Nude | CD105 |
| SW620 | Nude | CD105 & VE-cad |

All primers were designed to span large introns thereby preventing potential amplification of contaminating genomic DNA. Primers were only used if they produced a single band of the expected size upon gel electrophoresis and failed to produce primer dimer products as assessed by gel electrophoresis and melting point analysis on the MX4000. Conditions for amplification were: one cycle of 95° C., 10 min followed by 40 cycles of 95° C., 20 sec, 56° C., 30 sec, and 72° C., 30 sec. Quantitative PCR reactions were performed in duplicate and threshold cycle numbers were averaged. Gene expression was normalized to that of the 70 Kd U1 small nuclear ribonucleoprotein polypeptide A (Srnp70), a gene that is uniformly expressed in all ECs as assessed by SAGE. Relative expression was calculated using the formula $2^{(Rt-Et)}/2^{(Rn-En)}$ where Rt is the threshold cycle number observed in the experimental sample for Srnp70, Et is the threshold cycle number observed in the experimental sample for the gene of interest (GOI), $R_n$ is the average threshold cycle number observed for Srnp70 in all the N-EC samples and $E_n$ is the average threshold cycle number observed for the GOI in all the N-EC samples.

In Situ Hybridization. Digoxigenin (DIG)-labeled antisense RNA probes were generated by PCR amplification of 500-600 basepair products incorporating T7 promoters into the antisense primers. In vitro transcription was performed with DIG RNA labeling reagents and T7 RNA polymerase according to the manufacturer's instructions (Roche, Indianapolis, Ind.). Tumors and normal tissues were dissected, embedded in OCT, frozen in a dry ice-methanol bath, and cryosectioned at 10 µm. All sections were immediately fixed with 4% paraformaldehyde, permeabilized with proteinase K, rinsed with 5×SSC and incubated with RNA probes (100 ng/ml) diluted in ISH solution (Dako, Carpinteria, Calif.) overnight at 55° C. After washing three times with 2×SSC, sections were incubated at 37° C. with RNase Cocktail (Ambion, Austin, Tex.) diluted 1:200 in 2×SSC. Slides were stringently washed twice in 2×SSC/50% deionized formamide (American Bioanalytical, Natick, Mass.) and then once with 0.1×SSC at 55° C. Before immunodetection, tissues were treated with peroxidase blocking reagent (DAKO) and blocked with 1% blocking reagent (Roche) containing purified, nonspecific rabbit immunoglobulins (DAKO). For signal amplification, a horseradish peroxidase-rabbit anti-DIG antibody (DAKO) was used to catalyze the deposition of FITC-tyramide (GenPoint Fluorescein kit, DAKO). Further amplification was achieved by adding horseradish peroxidase-rabbit anti-FITC (DAKO), biotin-tyramide (GenPoint Kit, DAKO), and then alkaline phosphatase rabbit anti-biotin (DAKO). Signal was detected with the alkaline phosphatase substrate Fast Red TR/Napthol AS-MX (Sigma Chemical Co., St. Louis, Mo.). Cells were counterstained with a 1/40 diluted stock of hematoxylin and mounted with Aqueous Mounting Medium (BioGenex, San Ramon, Calif.).

Immunofluorescent studies. Dual-color immunofluorescence was performed on fresh-frozen sections fixed in Leukoperm (Serotec, Raleigh, N.C.). For CD105 detection, sections were stained with rat anti-mouse CD105 followed by FITC-linked goat-anti-rat (Jackson Immunoresearch Laboratories, West Grove, Pa.) and 488 goat anti-FITC (Invitrogen). VE-cadherin was detected using goat anti-mouse VE-cadherin followed by rhodamine-streptavidin (Vector Laboratories, Burlingame, Calif.). For dual CD276 and vWF immunofluorescence staining, tissues were simultaneously stained using a mouse anti-CD276 (R&D) monoclonal antibody and a rabbit anti-vWF polyclonal antibody (Dako). CD276 was detected with a FITC-conjugated goat anti-mouse antibody (Jackson Immunoresearch Laboratories) followed by a 488 goat-anti-FITC antibody (Invitrogen) and a 488 donkey anti-goat antibody (Invitrogen). vWF was detected using a biotin-linked donkey anti-rabbit antibody (Jackson Immunoresearch Laboratories) followed by rhodamine-streptavidin (Vector Laboratories, Burlingame, Calif.). Images were captured using a Nikon Eclipse E600 microscope.

Immunohistochemical studies. Paraffin sections were deparaffinized, incubated with proteinase K, heated at 95° C. for 20 min in citrate buffer (pH 6) (Invitrogen), and treated with peroxidase blocking reagent (Dako). Sections were incubated with a biotin-labelled polyclonal antibody against CD276 (R&D) followed by an HRP-conjugated anti-biotin antibody (Dako) and visualized by DAB (diaminobenzidine) staining. Sections were lightly counterstained with hematoxylin.

Immunoblot studies. A CD276 expression vector was made by excising a human CD276 cDNA from an EST (accession number BC7472032) using the restriction enzymes EcoR1 and Not1 and cloning the fragment into the same sites of the expression vector pcDNA3.1(+) (Invitrogen). Sequencing of the CD276/pcDNA3 vector revealed that it contained a full length CD276 cDNA corresponding to transcript variant 1 (accession number NM_001024736). CD276/pcDNA3 was transfected into 293 cells using lipofectamine, and stable transfectants selected with Geneticin. To generate extracts for immunoblotting, colorectal tissues stored at −80° C. were thawed, diced with a razor, immediately homogenized in cold TNT buffer [50 mM Tris (pH 7.5), 75 mM NaCl, 1% triton X-100 containing a cocktail of protease inhibitors (Roche)] and clarified by centrifugation. Protein extracts from tissues or lysed 293 cells were separated by SDS-PAGE and transferred to a PDVF membrane (Millipore). Immunoblots were probed with a monoclonal anti-CD276 antibody (eBioscience) or an anti-actin antibody (Chemicon) followed by an HRP-conjugated anti-mouse secondary antibody (Jackson), and visualized using the ECL plus system (Amersham) according to the supplier's instructions.

Example 2

Purification of Endothelial Cells from Normal and Malignant Tissues

This example describes methods used to immunopurify endothelial cells (ECs) from various tissue types.

Figure 1A:
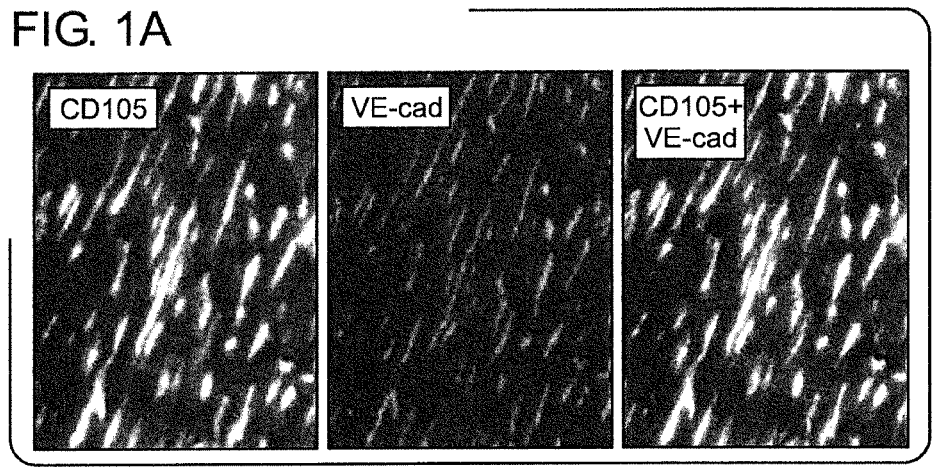
FIG. 1A includes digital images of heart tissue stained with immunofluorescently-labeled CD105 (left panel), VE-cadherin (middle panel) or both CD105 and VE-cadherin (right panel). Scale bar, 20 μm.
Figure 1B:
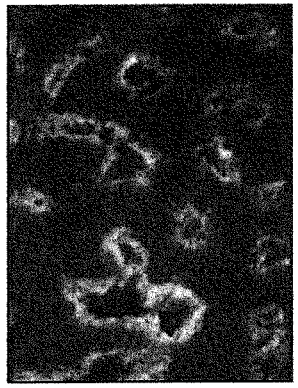
FIG. 1B is a digital image of liver tissue stained with immunofluorescently-labeled CD105. Scale bar, 20 μm.

Initial attempts to purify ECs involved antibody recognition of CD31, the conventional cell surface marker used for affinity purification of mouse ECs, were difficult because of its cross reactivity with hematopoietic cells. CD105 (endoglin) and/or VE-cadherin were found to be specifically localized to the ECs of normal and tumor tissues. For example, as illustrated in FIG. 1A, immunofluorescence staining of heart tissue demonstrated co-localization of CD105 (green) with VE-cadherin (red) in the heart vessels. Further, FIG. 1B demonstrates immunofluorscence staining of liver tissue with CD105 (green). CD105 was determined to be a preferred marker in liver because CD105 stained all the endothelium including sinusoidal ECs whereas VE-cadherin did not.

Figure 1C:
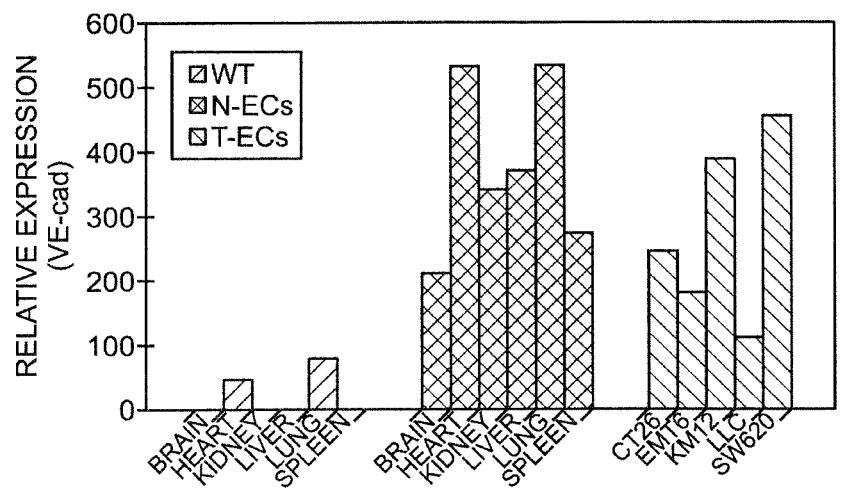
FIG. 1C is a bar graph showing the relative amount of VE-cadherin detected by quantitative polymerase chain reaction (QPCR) in cDNA isolated from unfractionated normal whole tissues (WT), purified endothelial cells (ECs) isolated from normal tissues (N-ECs) or purified ECs isolated from tumors (T-ECs).

The cell isolation involved tissue dissociation, the removal of non-ECs, and the positive selection of ECs using magnetic beads coupled to either anti-VE-cadherin or anti-CD105 antibodies, the choice depending on the tissue being dissociated (see Example 1, Material and Methods). To assess the purity of the isolated cells, QPCR analysis was performed on cDNA generated directly from unfractionated normal whole tissues (WT), purified ECs isolated from normal tissues (N-ECs) or ECs isolated from tumors. As illustrated in FIG. 1C, a marked enrichment of endothelial-specific genes such as VE-cadherin was found in each of the purified fractions compared to unfractionated whole tissues, but little contamination by hematopoietic cells, as judged by CD45 expression. For example, VE-cadherin was enriched 110 to 530-fold in the endothelial fractions. The modest level of VE-cadherin found in the unfractionated heart and lung sample is presumably due to a higher proportion of ECs in these tissues. Gene expression was normalized to that of the Eif4h, a gene found to be uniformly expressed in all cells as assessed by SAGE (Velculescu et al. *Nat. Genet.* 23: 387-8, 1999). Unfractionated brain was used to calibrate relative expression because this tissue had the lowest VE-cadherin expression levels.

Figure 1D:
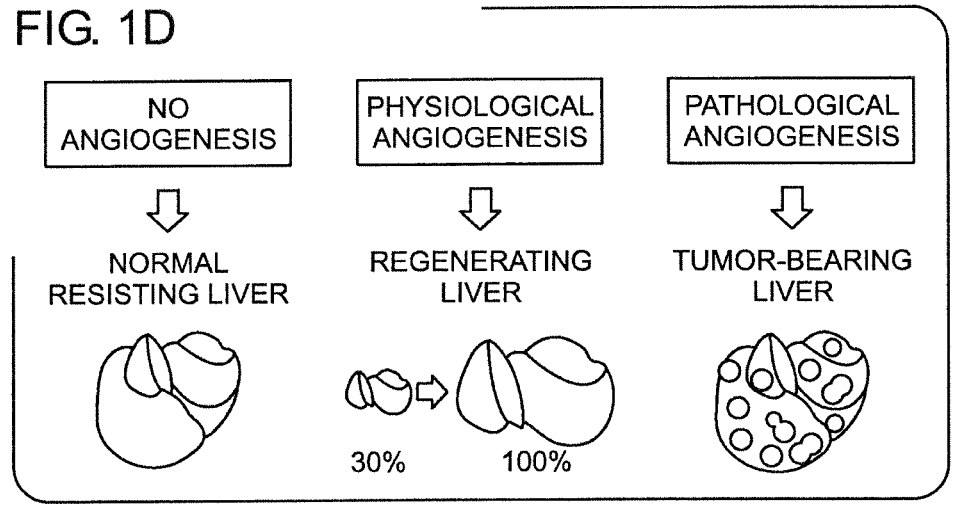
FIG. 1D is a schematic of a model used to identify genes expressed during pathological, but not physiological angiogenesis. ECs were isolated from normal resting livers, regenerating livers, or tumor bearing livers.

FIG. 1D provides a model used to identify genes expressed during pathological but not physiological angiogenesis. ECs were isolated from normal resting livers, regenerating livers, or tumor bearing livers.

Example 3

Identification of Organ-Specific Endothelial Cell Markers

This example illustrates methods used to identify 27 brain and 15 liver specific endothelial cell markers.

Antibodies against the endothelial selection markers CD105, VE-cadherin (VE-cad) or both were used in the positive selection to immunopurify the endothelial cells. Endothelial cells were derived from the host strain indicated, and the number of SAGE tags obtained for each library is indicated. These SAGE libraries utilized a 21 nucleotide "long tag" which facilitates the mapping of genes directly to genomic DNA even when EST or cDNA sequence was unavailable (Saha et al., *Nat. Biotechnol.* 20: 508-12, 2002). For SAGE comparisons, all endothelial cell libraries were normalized to 100,000 tags except for kidney which was normalized to 30,000 tags due to the lower number of tags obtained for the kidney endothelial cell library. As illustrated in Table 6, 700,189 tags were obtained from these 7 normal EC libraries.

TABLE 6

Identification of 7 normal EC libraries.

| | Strain | Selection Marker | No. Tags |
|---|---|---|---|
| Normal ECs | | | |
| Brain | C57BL/6 | CD105 & VE-cad | 168,029 |
| Heart | Balb/c | CD105 | 86966 |
| Kidney | Nude | CD105 | 29884 |
| Spleen | C57BL/6 | VE-cad | 93150 |

TABLE 6-continued

Identification of 7 normal EC libraries.

| | Strain | Selection Marker | No. Tags |
|---|---|---|---|
| Lung | Nude | CD105 | 104998 |
| Muscle | C57BL/6 | CD105 & VE-cad | 107,726 |
| Liver | Nude | CD105 | 109436 |
| Reg. Liv. Ecs | | | |
| 24 h | Nude | CD105 | 105,145 |
| 48 h | Nude | CD105 | 174880 |
| 72 h | Nude | CD105 | 115,209 |
| Tumor Ecs | | | |
| CT26 | Balb/c | VE-cad | 93,981 |
| EMT6 | Balb/c | CD105 & VE-cad | 114,910 |
| KM12 | Nude | CD105 | 167124 |
| LLC | C57BL/6 | VE-cad | 104,283 |
| SW620 | Nude | CD105 & VE-cad | 112312 |

Analysis of the transcripts revealed the presence of multiple endothelial-specific transcripts, while epithelial, hematopoietic and hepatocyte markers were absent or rare (See Tables 7A and 7B). Tag counts for endothelial, hematopoietic, epithelial, hepatocyte, pericyte/smooth muscle cell, lymphatic endothelial, and fibroblasts markers were obtained by normalizing to 100,000 tags for each of the SAGE libraries shown. The hematopoietic cell fraction (HCF) control was derived from 53,271 SAGE tags. This SAGE library was constructed from hematopoietic cells that had been purified from collagenase dispersed KM12SM tumors using a mixture of magnetic beads coupled to anti-F480, anti-CD45, anti-CD68 and anti-CD19 antibodies. The unfractionated (Unfrac.) liver control was derived from 37,162 SAGE tags originating from C57BL/6 whole liver and is publicly available at SAGEmap (World Wide Web address of ncbi.nlm.nih.gov/projects/SAGE/). The unfractionated intestine control was derived from 115,942 SAGE tags originating from microscope-dissected small intestine of a late gestation embryo also available at SAGEmap. The endothelial libraries are the same as those found in Table 6.

Tables 7A and 7B. Multiple endothelial-specific transcripts in the 7 normal EC libraries.

TABLE 7A

Endothelial purity in normal endothelial cells and controls.

| | Controls | | | Normal ECs | | | | | | | |
|---|---|---|---|---|---|---|---|---|---|---|---|
| | Unfra. Liver | Unfra. Intestine | HCF | Brain | Heart | Kidney | Liver | Lung | Muscle | Spleen | |
| Endothelial markers | 5 | 3 | 0 | 77 | 117 | 80 | 74 | 104 | 106 | 9 | CD31 (PECAM) |
| | 0 | 2 | 0 | 24 | 46 | 30 | 60 | 25 | 24 | 15 | CD105 (Endoglin) |
| | 3 | 1 | 0 | 213 | 32 | 60 | 33 | 210 | 30 | 37 | Claudin 5 |
| | 8 | 12 | 0 | 46 | 53 | 50 | 55 | 94 | 104 | 14 | VE-cadherin |
| | 0 | 2 | 0 | 13 | 13 | 50 | 82 | 18 | 21 | 3 | VEGFR2 |
| | 0 | 0 | 0 | 224 | 137 | 10 | 58 | 48 | 72 | 0 | vonWillebrand Factor |
| Hematopoietic markers | 0 | 0 | 15 | 0 | 0 | 0 | 0 | 0 | 0 | 0 | CD18 |
| | 0 | 0 | 15 | 0 | 0 | 0 | 0 | 0 | 0 | 0 | CD45(Ly-5) |
| | 0 | 0 | 43 | 0 | 0 | 0 | 0 | 0 | 0 | 0 | Interleukin 10 |
| | 0 | 0 | 30 | 0 | 0 | 0 | 0 | 0 | 0 | 0 | Macrophage scavenger Rec. 2 |
| Epithelial markers | 5 | 19 | 0 | 0 | 0 | 0 | 0 | 1 | 0 | 0 | Cytokeratin 8 |
| | 0 | 17 | 0 | 0 | 0 | 0 | 0 | 4 | 0 | 0 | E-cadherin |
| Hepatocyte markers | 501 | 0 | 0 | 0 | 0 | 0 | 3 | 0 | 0 | 0 | Albumin |
| | 414 | 0 | 0 | 0 | 0 | 0 | 0 | 0 | 0 | 0 | Fibrinogen, B beta |
| Pericyte/ SMC markers | 0 | 2 | 2 | 2 | 1 | 3 | 0 | 0 | 0 | 0 | NG2 (Cspg4) |
| | 0 | 24 | 0 | 1 | 1 | 0 | 0 | 0 | 0 | 0 | Calponin-1 |
| Lymphatic | 0 | 1 | 0 | 1 | 0 | 0 | 6 | 0 | 0 | 0 | Podoplanin |

TABLE 7A-continued

Endothelial purity in normal endothelial cells and controls.

|  | Controls | | | Normal ECs | | | | | | | |
|---|---|---|---|---|---|---|---|---|---|---|---|
|  | Unfra. Liver | Unfra. Intestine | HCF | Brain | Heart | Kidney | Liver | Lung | Muscle | Spleen |  |
| endothelial markers | 0 | 1 | 0 | 0 | 2 | 0 | 0 | 0 | 2 | 4 | Prox-1 |
| Fibroblast markers | 0 | 3 | 0 | 0 | 0 | 0 | 0 | 0 | 1 | 0 | Fibroblast Activation Protein |

TABLE 7B

Endothelial purity in regenerativing liver endothelial cells and tumor endothelial cells

|  | Reg. Liver ECs | | | Tumor ECs | | | | | |
|---|---|---|---|---|---|---|---|---|---|
|  | 24 hr | 48 hr | 72 hr | CT26 | EMT6 | KM12SM | LLC | SW620 |  |
| Endothelial markers | 95 | 90 | 69 | 85 | 77 | 34 | 151 | 82 | CD31 (PECAM) |
|  | 40 | 50 | 37 | 10 | 22 | 20 | 15 | 22 | CD105 (Endoglin) |
|  | 16 | 13 | 20 | 35 | 37 | 13 | 62 | 22 | Claudin 5 |
|  | 46 | 51 | 52 | 63 | 50 | 28 | 116 | 58 | VE-cadherin |
|  | 12 | 45 | 38 | 21 | 14 | 17 | 9 | 29 | VEGFR2 |
|  | 133 | 58 | 45 | 56 | 23 | 25 | 52 | 36 | vonWillebrand Factor |
| Hematopoietic Markers | 1 | 0 | 2 | 1 | 1 | 0 | 0 | 0 | CD18 |
|  | 0 | 0 | 2 | 0 | 0 | 0 | 1 | 0 | CD45(Ly-5) |
|  | 0 | 0 | 2 | 0 | 0 | 0 | 0 | 0 | Interleukin 10 |
|  | 0 | 0 | 0 | 0 | 0 | 0 | 0 | 0 | Macrophage scavenger Rec. 2 |
| Epithelial Markers | 0 | 0 | 0 | 0 | 3 | 0 | 0 | 0 | Cytokeratin 8 |
|  | 0 | 0 | 0 | 0 | 0 | 0 | 0 | 0 | E-cadherin |
| Hepatocyte markers | 0 | 3 | 2 | 0 | 0 | 1 | 0 | 0 | Albumin |
|  | 0 | 0 | 0 | 0 | 0 | 0 | 0 | 0 | Fibrinogen, B beta |
| Pericyte/ SMC markers | 0 | 1 | 1 | 0 | 1 | 1 | 0 | 0 | NG2 (Cspg4) |
|  | 0 | 0 | 0 | 0 | 0 | 2 | 0 | 2 | Calponin-1 |
| Lymphatic endothelial markers | 1 | 0 | 0 | 2 | 4 | 2 | 0 | 0 | Podoplanin |
|  | 0 | 0 | 1 | 0 | 0 | 0 | 0 | 0 | Prox-1 |
| Fibroblast markers | 0 | 0 | 0 | 0 | 1 | 1 | 0 | 1 | Fibroblast Activation Protein |

Brain Endothelial Markers (BEMs) were defined as genes that were expressed 20-fold or higher in brain compared to all other normal endothelium (see Table 8, below). The most abundant and differentially expressed gene identified was the brain glucose transporter Glut-1, a blood-brain barrier (BBB) marker previously found to be expressed on the luminal surface of brain endothelium (Farrell & Pardridge, *Proc. Natl. Acad. Sci. U.S.A.* 88:5779-83, 1991; Pardridge et al. *J. Biol. Chem.* 265:18035-40, 1990). Thirteen of the 27 BEMs (~50%) appear to reside at the cell surface and at least 9 of these are transporters potentially involved in BBB function. Seven of the BEMs, including five cell surface transporters, were previously localized to brain endothelium by in situ staining. Some of the cell surface transporters have also been identified in liver tissues where they appear to be expressed predominantly by hepatocytes or other non-ECs (Gu et al. *Proc. Natl. Acad. Sci. U.S.A.* 97:3230-5, 2000; Konig et al. *Am. J. Physiol. Gastrointest. Liver Physiol.* 278:G156-64, 2000; and Mesh et al. *Eur. J. Biochem.* 271:3103-14, 2004). Intracellular enzymes, such as glutathione-S-transferase alpha 4 (Gsta4), were also identified which may be involved in protecting the brain from toxic chemicals that enter the blood.

Liver Endothelial Markers (LEMs) were defined as genes that were expressed 20-fold or higher in liver compared to all other normal endothelium (Table 8). The most highly expressed gene was deoxyribonuclease 1-like 3, a recently identified nuclease that may be involved with chromatin clearance from the circulation (Napirei et al. *Biochem. J.* 389:355-64, 2005). CD32 is a low affinity Fc γ-receptor that is a known marker of liver sinusoidal ECs (Muro et al. *Am. J. Pathol.* 143:105-20, 1993). Two lectin-like receptors, one of which was shown recently to be expressed predominantly by sinusoidal ECs of human liver and lymph node (Liu et al. *J. Biol. Chem.* 279:18748-58, 2004) were also identified. Seven of the LEMs identified appear to reside at the cell surface, including three that have not yet been characterized. These results highlight the complexity of blood vessels and demonstrate the existence of multiple organ-specific endothelial markers in different tissues.

TABLE 8

Organ-specific endothelial cell markers.

| | Brain | Heart | Kidney | Liver | Lung | Muscle | Spleen | GenBank Acc.# | Description* |
|---|---|---|---|---|---|---|---|---|---|
| | | | | | Brain endothelial markers | | | | |
| 1 | 754 | 8 | 1 | 2 | 1 | 12 | 4 | NM_011400 | GLUT-1 |
| 2 | 157 | 0 | 0 | 0 | 0 | 1 | 0 | NM_030687 | Organic anion transporter 2 |
| 3 | 93 | 0 | 1 | 0 | 0 | 1 | 1 | NM_008973 | Pleiotrophin |
| 4 | 32 | 0 | 0 | 0 | 0 | 0 | 0 | NM_009728 | ATPase, class V, type 10A |
| 5 | 40 | 0 | 0 | 0 | 1 | 0 | 0 | NM_009402 | Peptidoglycan recognition protein 1 |
| 6 | 26 | 0 | 0 | 0 | 0 | 0 | 0 | NM_021471 | Organic anion transp. 14 |
| 7 | 29 | 0 | 0 | 0 | 0 | 0 | 0 | NM_008239 | Forkhead box Q1 |
| 8 | 19 | 0 | 0 | 0 | 0 | 0 | 0 | NM_031194 | Organic anion transporter 3 |
| 9 | 73 | 0 | 0 | 0 | 3 | 0 | 0 | NM_172479 | SN2, Solute carrier family 38, member 5 |
| 10 | 40 | 0 | 0 | 0 | 1 | 2 | 0 | NM_172471 | Inter-alpha (globulin) inhibitor H5 |
| 11 | 12 | 0 | 0 | 0 | 0 | 0 | 0 | NM_010703 | Lymphoid enhancer binding factor 1 |
| 12 | 23 | 0 | 0 | 0 | 0 | 0 | 1 | NM_011404 | Slc7a5 aa transporter |
| 13 | 20 | 1 | 0 | 0 | 0 | 0 | 0 | NM_023805 | Solute carrier family 38, member 3 |
| 14 | 17 | 0 | 0 | 0 | 0 | 0 | 0 | NM_009574 | Zinc finger protein of the cerebellum 2 |
| 15 | 81 | 6 | 0 | 0 | 1 | 3 | 0 | NM_052994 | Testican-2 |
| 16 | 26 | 0 | 1 | 0 | 1 | 1 | 0 | NM_008256 | 3-HMG-CoA synthase 2 |
| 17 | 15 | 0 | 0 | 0 | 0 | 0 | 0 | NM_028748 | Progestin and adipoQ receptor family member V |
| 18 | 68 | 0 | 1 | 2 | 1 | 0 | 1 | AK172004 | APC down-regulated 1, Drapc 1 |
| 19 | 13 | 0 | 0 | 1 | 0 | 0 | 0 | NM_027096 | Unknown, GDPD phosphodiesterase family |
| 20 | 26 | 0 | 0 | 3 | 1 | 0 | 0 | NM_029001 | Unknown, putative transmembrane protein |
| 21 | 19 | 1 | 0 | 0 | 0 | 1 | 0 | NM_027299 | DES2, lipid desaturase/C4-hydroxylase |
| 22 | 39 | 0 | 1 | 0 | 2 | 0 | 1 | XM_486083 | Unknown, kelch repeat and BTB (POZ) domain |
| 23 | 46 | 2 | 1 | 0 | 1 | 1 | 0 | NM_017405 | Lipolysis stimulated receptor |
| 24 | 36 | 2 | 0 | 0 | 1 | 1 | 0 | NM_010357 | Glutathione S-transferase, alpha 4 |
| 25 | 9 | 0 | 0 | 0 | 1 | 0 | 0 | NM_013869 | TNF receptor superfamily, member 19 |
| 26 | 17 | 1 | 0 | 0 | 0 | 1 | 0 | NM_011532 | T-box 1 |
| 27 | 6 | 0 | 0 | 0 | 1 | 0 | 0 | XM_620023 | Unknown, putative transmembrane protein |
| | | | | | Liver endothelial markers | | | | |
| 1 | 0 | 0 | 0 | 196 | 0 | 0 | 0 | NM_007870 | Deoxyribonuclease 1-like 3 |
| 2 | 0 | 0 | 0 | 58 | 0 | 0 | 3 | NM_010959 | LZP, oncoprotein induced transcript 3 |
| 3 | 0 | 0 | 0 | 16 | 0 | 0 | 0 | NM_023438 | Unknown‡, putative transmembrane protein |
| 4 | 1 | 0 | 0 | 123 | 0 | 0 | 6 | AK150613 | CD32 |
| 5 | 0 | 1 | 0 | 33 | 0 | 1 | 1 | NM_033616 | Unknown, putative G-protein coupled receptor |
| 6 | 0 | 1 | 0 | 14 | 0 | 0 | 0 | NM_019985 | C-type lectin-like receptor 2 |
| 7 | 0 | 0 | 0 | 216 | 0 | 0 | 24 | NM_029465 | Clec4g (LSECtin) |
| 8 | 0 | 1 | 0 | 42 | 2 | 1 | 0 | NM_018797 | Plexin C1 |
| 9 | 0 | 1 | 0 | 9 | 0 | 0 | 0 | NM_011719 | Wnt9B |
| 10 | 1 | 0 | 0 | 16 | 1 | 0 | 0 | AK144596 | Unknown |
| 11 | 0 | 1 | 0 | 9 | 0 | 0 | 0 | NM_008092 | GATA-binding protein 4 |
| 12 | 0 | 0 | 0 | 10 | 1 | 2 | 0 | AB049755 | MBL-associated serine protease-3 |
| 13 | 0 | 0 | 0 | 5 | 0 | 0 | 1 | NM_023132 | Renin binding protein |
| 14 | 0 | 0 | 0 | 16 | 1 | 2 | 1 | NM_144830 | Unknown, putative transmembrane protein |
| 15 | 1 | 0 | 1 | 11 | 0 | 0 | 0 | NM_011243 | Retinoic acid receptor, beta |

Example 3

Gene Expression in Resting Normal ECs, Regenerating Liver ECs and Tumor ECs

This example illustrates the expression of various markers in resting normal ECs, regenerating liver ECs and tumor ECs.

In order to identify genes that were elevated during physiological angiogenesis, ECs were isolated from liver at 24-, 48- or 72-hours following partial hepatectomy, the period during which endothelial growth is thought to occur (Michalopoulos & DeFrances. *Science* 276:60-66, 1997). In total, 395,234 SAGE tags were isolated from regenerating liver (See Table 6). Gene expression patterns of regenerating liver ECs were compared with a combined set of EC libraries derived from all non-proliferating normal organs including resting liver (see FIG. 1D). This comparison revealed 12 genes that were overexpressed in regenerating liver ECs compared to non-angiogenic ECs (Table 9), which were referred to as physiological angiogenesis endothelial markers.

At least seven of these genes may be involved in regulating progression through the cell cycle, consistent with the fact that these ECs are dividing. For example, the most abundant physiological angiogenesis marker is an ubiquitin-conjugating enzyme, Ube2c. Its human counterpart, UbCH10, is involved in progression through the G1 phase of the cell cycle (Townsley et al. *Proc. Natl. Acad. Sci. U.S.A.* 94:2362-7, 1997; and Rape & Kirschner. *Nature* 432:588-95, 2004). Protein regulator of cytokinesis 1 (PRC1) is a mitotic spindle-associated CDK substrate that is involved in cytokinesis (Jiang et al. *Mol. Cell.* 2:877-85, 1998). DNA topoisomerase II-alpha (Top2a), Thymidine Kinase 1 (TK1) and the Ki67 antigen are markers of proliferating cells (Gerdes et al. *J. Immunol.* 133: 1710-1715, 1984; Sampson et al. *J. Pathol.* 168: 179-185, 1992; and Bradshaw *Proc. Natl. Acad. Sci. U.S.A.* 80:5588-91, 1983). One extracellular matrix glycoprotein, Tenascin C, is frequently associated with angiogenesis of malignant tumors, inflamed tissues and healing wounds (Tanaka et al. *Int. J. Cancer* 108: 31-40, 2004; and Zagzag et al. *Cancer Res.* 56: 182-9, 1996). The only physiological angiogenesis endothelial marker identified encoding a predicted cell surface product was integrin β3, a receptor that partners with integrin αv and is thought to regulate angiogenesis (Brooks et al. *Science* 264:569-71, 1994).

angiogenesis markers, the results are expressed as the ratio between the gene of interest and Srnp70 expression and are normalize to the average expression in all non-angiogenic normal ECs. For Oatp2, samples were normalized to the average expression in intestinal, heart and kidney ECs. For comparison, normal ECs from resting liver (time=zero hours) were grouped with the regenerating liver ECs.

Figure 2A:
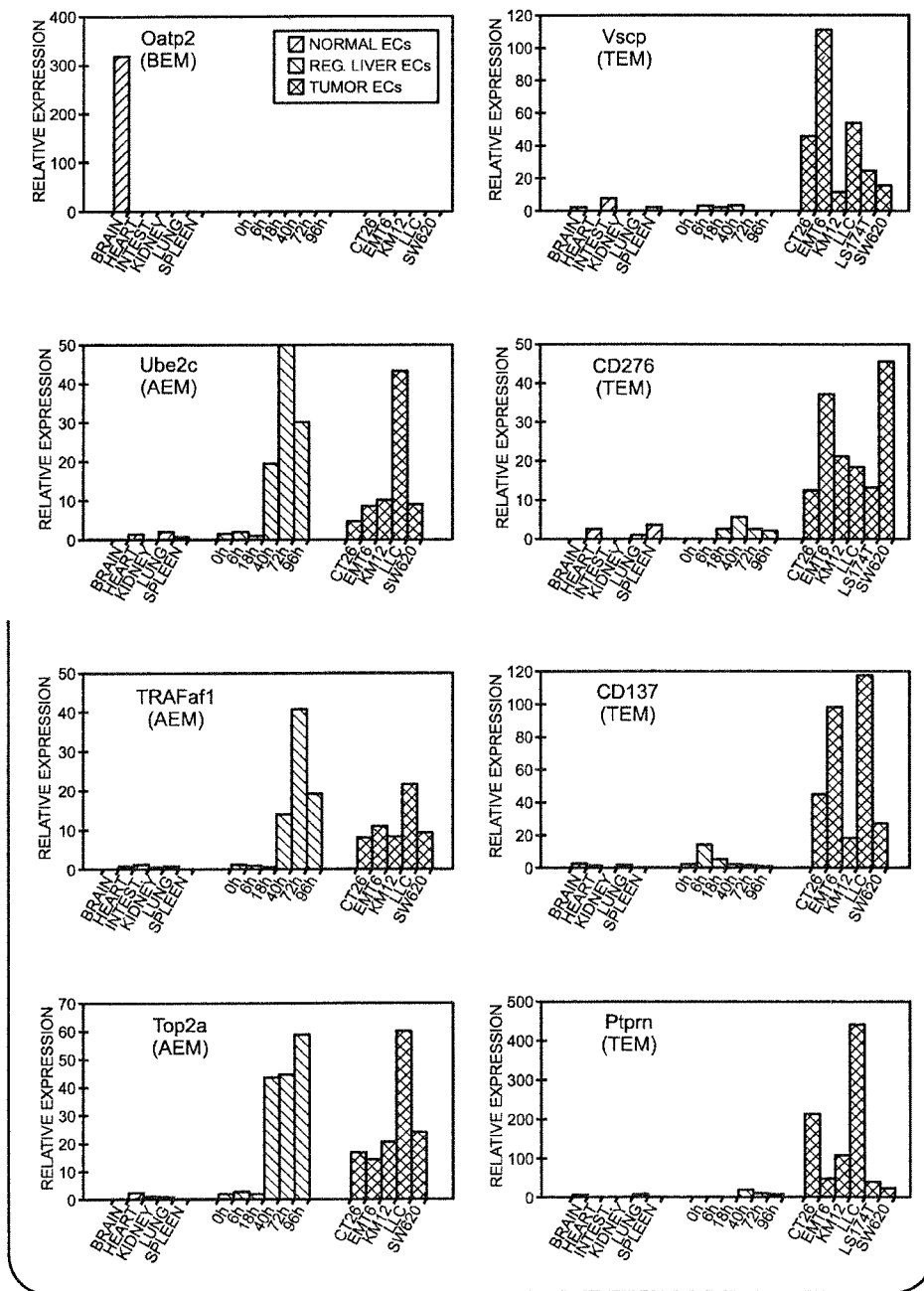
FIGS. 2A, 2B and 2C are bar graphs illustrating the expression of various genes in resting normal ECs, regenerating liver ECs and tumor ECs, respectively. The expression of the various genes was evaluated by real-time Q-PCR and compared with that of Srnp70, a gene expressed at nearly identical levels in all ECs as detected by SAGE.
Figure 2B:
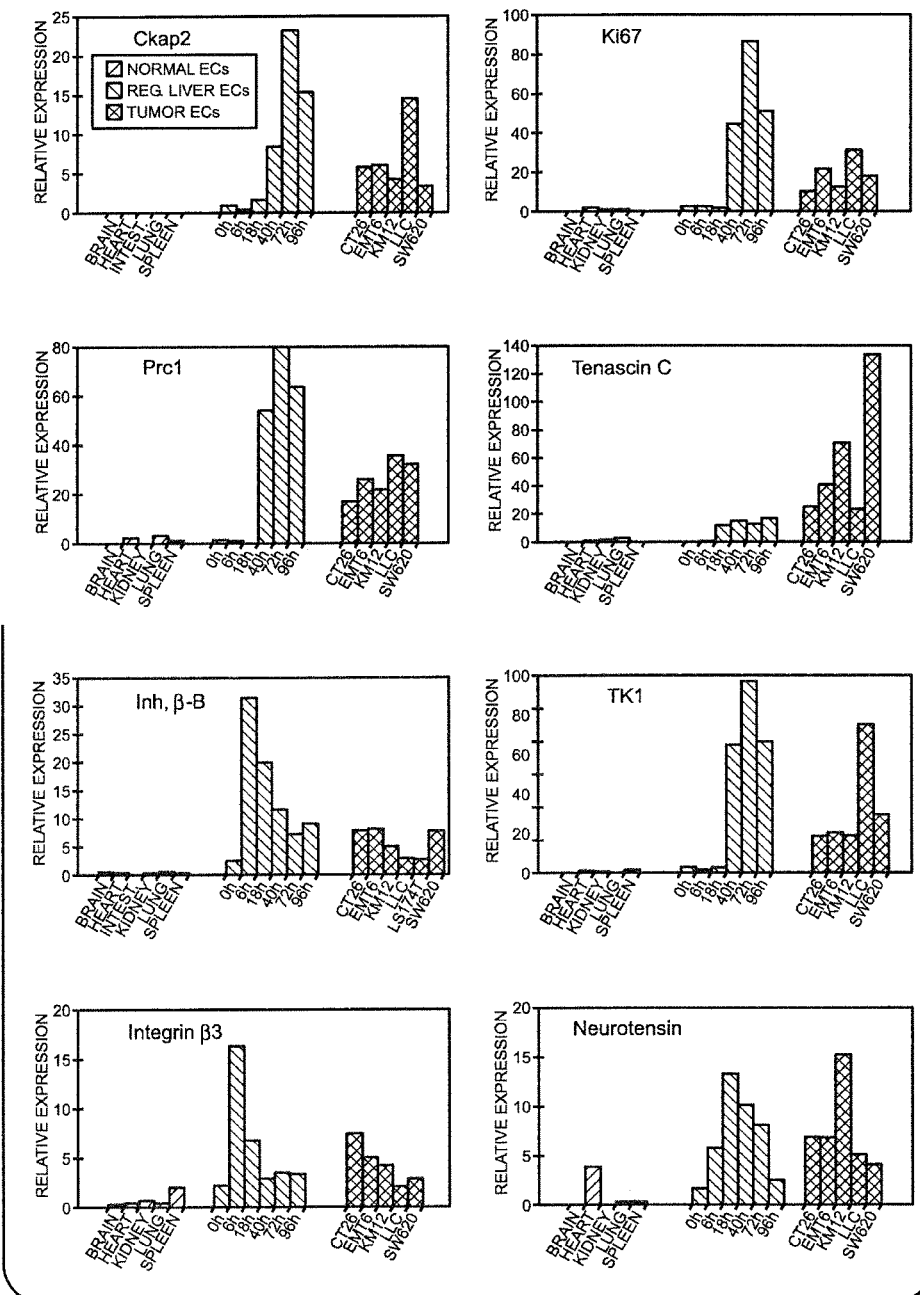

QPCR analysis confirmed that each of the physiological angiogenesis markers (Table 9) were induced in the regenerating liver ECs, with peak levels ranging from 15- to 100-fold over non-proliferating ECs (FIGS. 2A and 2B). All of the physiological angiogenesis markers genes identified were also found to be overexpressed in tumor endothelial cells (see Table 9), providing further evidence that expression of these genes is upregulated during angiogenesis. Although most of the genes displayed maximum mRNA expression at 72 hours, the genes encoding inhibin-beta B and α3-integrin reached their peak expression levels by 6 hours. Such early endothelial response genes may be important upstream regulators of the angiogenic cascade.

TABLE 9

Physiological and Pathological Angiogenesis Endothelial Cell Markers.

| Normal resting ECs | | | | | | | Reg. Liver ECs | | | Tumor ECs | | | | | | |
|---|---|---|---|---|---|---|---|---|---|---|---|---|---|---|---|---|
| Brain | Heart | Kidney | Liver | Lung | Muscle | Spleen | 24 h | 48 h | 72 h | CT26 | EMT | KM | LLC | SW | GenBank Acc. # | Description |
| Physiological Angiogenesis Markers | | | | | | | | | | | | | | | | |
| 0 | 0 | 0 | 0 | 0 | 0 | 0 | 0 | 10 | 14 | 5 | 3 | 4 | 9 | 0 | NM_026785 | Ube2c* |
| 0 | 0 | 0 | 0 | 0 | 0 | 0 | 1 | 5 | 11 | 0 | 5 | 2 | 3 | 2 | NM_026412 | TRAF4afl |
| 0 | 0 | 0 | 1 | 1 | 0 | 0 | 0 | 17 | 16 | 5 | 8 | 3 | 11 | 10 | NM_011623 | DNA topo IIα* |
| 0 | 0 | 0 | 0 | 0 | 0 | 0 | 0 | 4 | 3 | 3 | 2 | 2 | 8 | 0 | NM_001004140 | Ckap2* |
| 1 | 1 | 0 | 1 | 0 | 2 | 0 | 19 | 11 | 3 | 31 | 28 | 14 | 20 | 11 | NM_008381 | Inhibin beta-B |
| 0 | 0 | 0 | 1 | 0 | 0 | 0 | 0 | 4 | 6 | 5 | 6 | 5 | 5 | 7 | NM_025415 | Cks2* |
| 1 | 0 | 0 | 1 | 0 | 0 | 0 | 4 | 13 | 12 | 7 | 6 | 1 | 8 | 5 | NM_009387 | TK1* |
| 0 | 0 | 0 | 0 | 1 | 2 | 0 | 0 | 2 | 6 | 5 | 14 | 16 | 24 | 12 | NM_011607 | Tenascin C |
| 0 | 3 | 0 | 0 | 0 | 0 | 0 | 5 | 3 | 3 | 5 | 5 | 3 | 9 | 1 | NM_024435 | Neurotensin |
| 0 | 0 | 0 | 1 | 1 | 0 | 0 | 0 | 5 | 10 | 5 | 3 | 4 | 10 | 0 | NM_145150 | Prc1* |
| 0 | 0 | 0 | 0 | 1 | 1 | 2 | 0 | 11 | 12 | 7 | 7 | 2 | 5 | 4 | XM_133912 | Ki67 antigen* |
| 0 | 1 | 0 | 1 | 0 | 1 | 1 | 3 | 5 | 3 | 17 | 10 | 6 | 4 | 9 | NM_016780 | Integrin-β3† |
| Pathological Angiogenesis Markers | | | | | | | | | | | | | | | | |
| 0 | 0 | 0 | 0 | 1 | 0 | 0 | 1 | 1 | 1 | 7 | 11 | 0 | 26 | 4 | DQ832275 | Vscp |
| 0 | 1 | 0 | 0 | 0 | 0 | 0 | 0 | 1 | 0 | 1 | 6 | 3 | 10 | 16 | DQ832276 | CD276† (B7-H3) |
| 0 | 0 | 0 | 0 | 1 | 0 | 0 | 0 | 0 | 1 | 6 | 4 | 5 | 9 | 12 | DQ832277 | ETSvg4 (Pea3) |
| 0 | 1 | 0 | 0 | 0 | 0 | 0 | 0 | 0 | 0 | 8 | 2 | 1 | 26 | 3 | DQ832278‖ | CD137† (4-1BB) |
| 0 | 2 | 1 | 0 | 0 | 0 | 1 | 0 | 0 | 0 | 15 | 5 | 19 | 8 | 37 | DQ832280 | MiRP2† |
| 0 | 0 | 0 | 0 | 0 | 0 | 0 | 0 | 0 | 0 | 3 | 5 | 0 | 2 | 1 | NM_023137 | Ubiquitin D (FAT10) |
| 0 | 0 | 0 | 0 | 0 | 1 | 1 | 0 | 0 | 0 | 1 | 3 | 0 | 17 | 5 | DQ832281 | Doppel† (Prion-PLP) |
| 0 | 0 | 1 | 0 | 1 | 0 | 0 | 0 | 0 | 0 | 0 | 6 | 2 | 7 | 7 | DQ832282 | Apelin |
| 1 | 1 | 1 | 0 | 0 | 0 | 0 | 0 | 0 | 0 | 2 | 10 | 4 | 5 | 7 | NM_008827 | Plgf |
| 0 | 1 | 0 | 0 | 1 | 0 | 0 | 0 | 0 | 0 | 14 | 1 | 1 | 5 | 0 | DQ832283 | Ptprn† (IA-2) |
| 0 | 0 | 1 | 0 | 0 | 0 | 0 | 1 | 0 | 1 | 0 | 6 | 3 | 7 | 1 | DQ832284 | CD109† |
| 1 | 0 | 0 | 0 | 0 | 0 | 0 | 2 | 1 | 0 | 10 | 1 | 1 | 5 | 1 | DQ832285 | Ankylosis† |
| 0 | 0 | 1 | 0 | 1 | 0 | 0 | 1 | 0 | 0 | 3 | 2 | 8 | 1 | 5 | NM_007739 | Coll. VIII, α1 |

*Genes encoding products thought to be important in cell cycle control
†Encodes known or predicted cell surface protein
‡Gene name is given followed by alternative names in parenthesis
‖The Genbank accession number for the secreted variant sCD137 is DQ832279

Figure 2C:
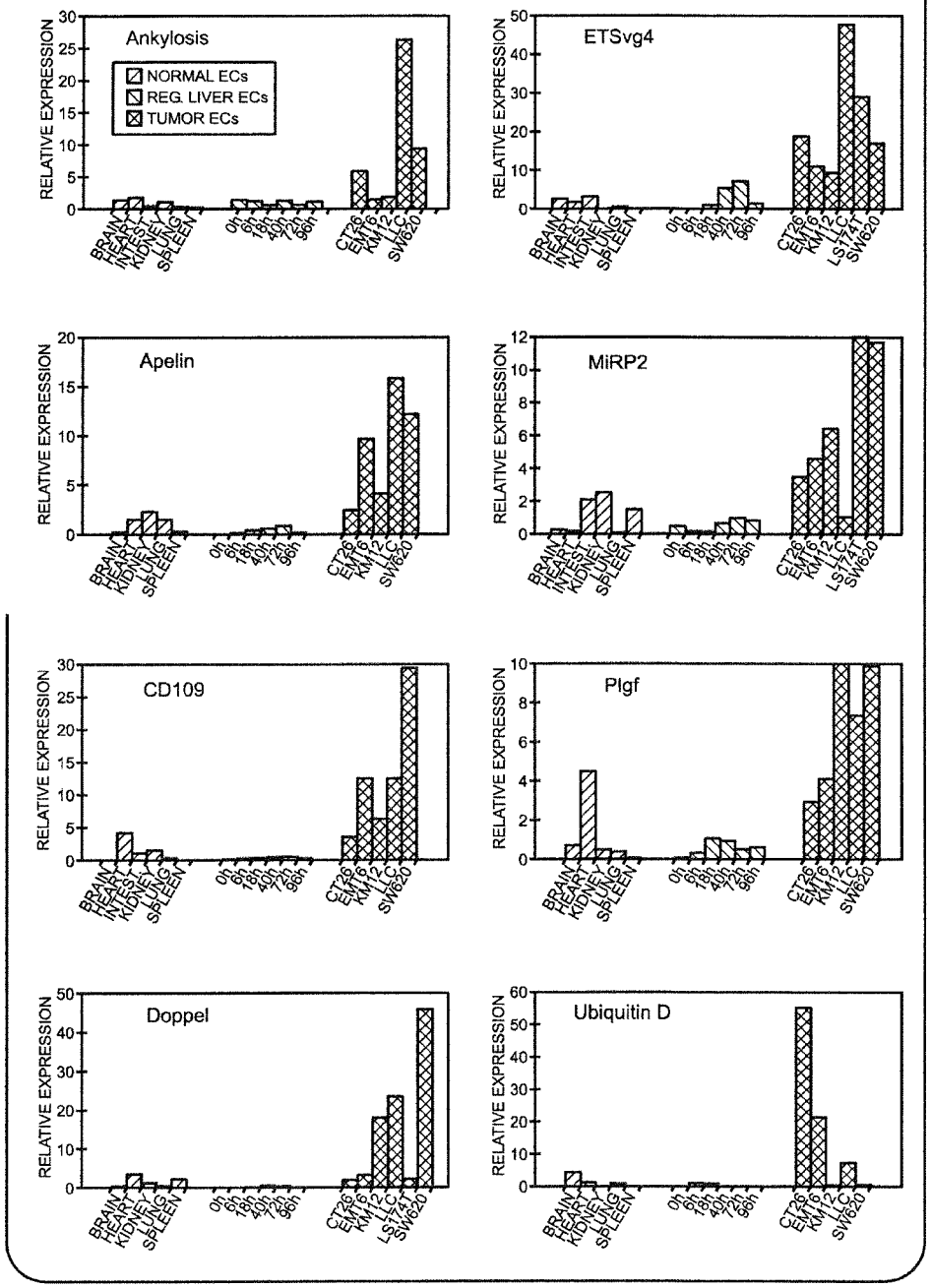

Gene expression was evaluated by real-time QPCR and compared with that of Srnp70, a gene expressed at nearly identical levels in all ECs, by SAGE. Organic-anion-transporter 2 (Oatp2) is a BEM, Ube2c, TRAFafl, and DNA topoisomerase IIα (Top2a) are physiological angiogenesis markers, and Vscp, CD276, Ptprn and CD137 are pathological angiogenesis markers. For physiological and pathological Each of the disclosed pathological angiogenesis genes detected by QPCR had a similar pattern of expression to that predicted by the SAGE analysis, with levels of expression barely detectable in regenerating liver endothelium (FIG. 2A and FIG. 2C). Most of the genes were overexpressed in the ECs of all of the tumors examined, although 6 of the genes (Ankylosis, Apelin, MiRP2, CD109, Doppel and Ubiquitin D) were overexpressed in the vessels of only a subset of the tumor types. Ubiquitin D was only expressed in the vessels of mouse tumors (CT26, EMT6 and LLC), but was essentially undetectable by QPCR in tissue culture-derived tumor cells.

Figure 7:
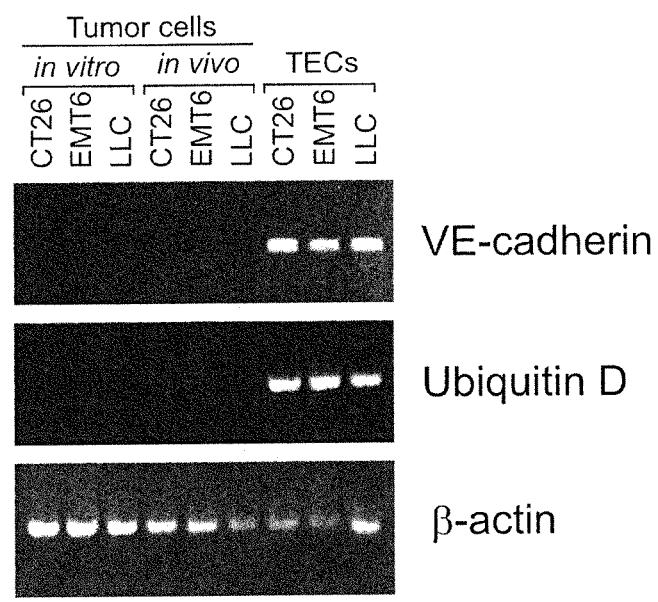
FIG. 7 is a digital image of amplification products generated in tumor cell lines or tumor endothelial cells in the presence of VE-cadherin, Ubiquitin D or β-actin primers.

RT-PCR was used to verify that Ubiquitin D is expressed by the tumor endothelial cells (TECs) and not the tumor cells themselves. To generate cDNA for RT-PCR, mRNA was extracted from CT26, EMT6 and LLC tumor cell lines grown in tissue culture, the corresponding tumor cells isolated from tumors grown in vivo, or the corresponding TECs isolated from the same tumors. To isolate tumor cell-enriched fractions in vivo, tumors were dispersed with collagenase and endothelial cells and hematopoietic cells were removed using magnetic dynabeads coupled to CD105 and CD45. Tumor endothelial cells were isolated as described in the Examples (such as Example 1). PCR amplification of VE-cadherin was used as a control to verify the endothelial origin of the purified tumor endothelial cells, and β-actin was used as housekeeping control to ensure the presence of similar amounts of template in each of the samples. As illustrated in FIG. 7, Ubiquitin D mRNA was essentially undetectable when RT-PCR was performed on in vivo tumor cell-enriched fractions or the tumor cell lines grown in tissue culture indicating that such expression is not due to the presence of contaminating tumor cells.

Example 4

Figure 3:
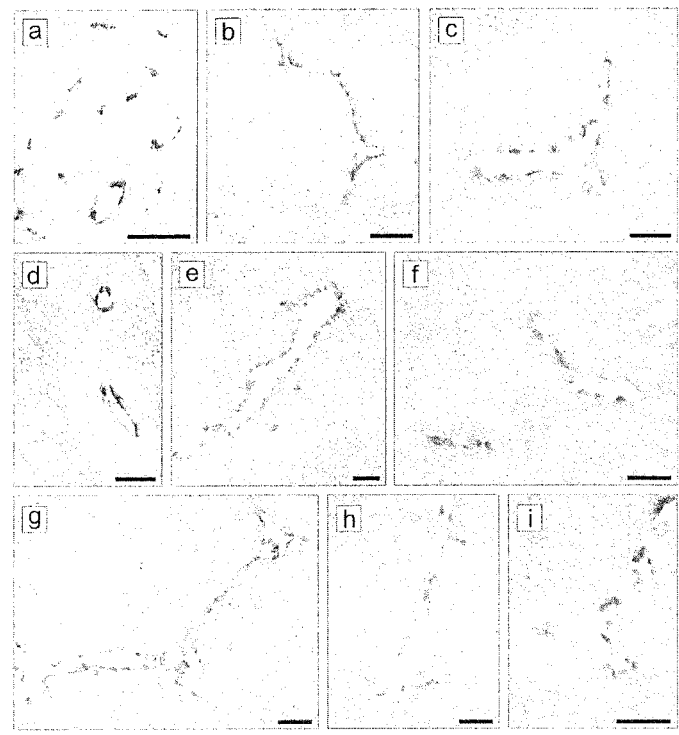
FIGS. 3A-3I are digital images of various mRNA expressed by ECs in vivo detected by staining samples with Oatp2 (a), CD276 (b), ETSvg4 (c), Apelin (d), CD109 (e), MiRP2 (f), CD137 (g), Doppel (h) and Vscp (i). (a) is representative of a brain endothelial marker in brain tissue, (b) and (c) depict HCT116 tumors grown subcutaneously, (d-f) depict SW620 tumors grown subcutaneously, and (g-h) depict KM12 tumors grown in the liver. A dilute counterstain was applied to the sections to highlight the lack of detectable expression in the non-ECs of the tumors. Scale bars, 50 μM.
Figure 9B:
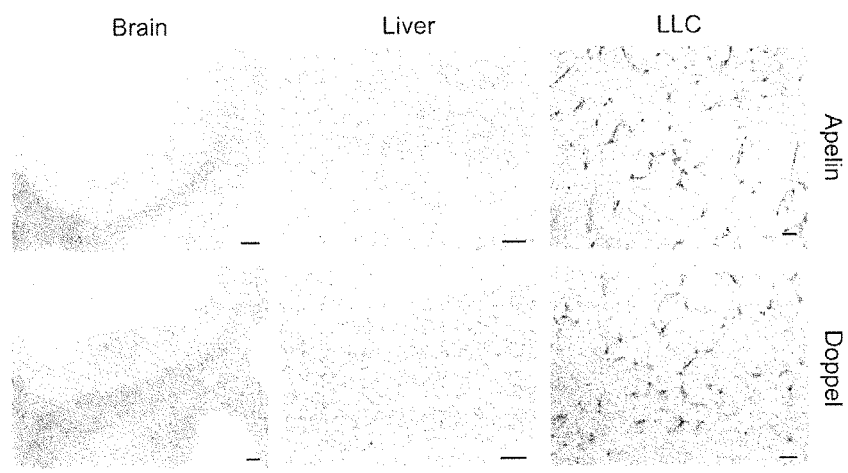

Pathological Angiogenesis Endothelial Marker Genes Identified by Sage are Expressed by ECs in Tumor Vessels In Vivo This example demonstrates that the tumor endothelial marker genes identified by SAGE (Example 1) are expressed by ECs in tumor vessels in vivo. To exclude the possibility that the differentially expressed transcripts were derived from other contaminating non-ECs, mRNA in situ hybridization studies using a highly sensitive non-radioactive technique were performed (FIG. 3, FIG. 9A, FIG. 9B and Table 10).

Table 10 illustrates in situ hybridization results of BEMs and LEMs in normal adult brain and liver tissues. Expression of BEM or LEM mRNA was analyzed in resting adult brain and liver tissues and scored as negative (−), moderately positive (+), moderate to strongly positive (++) or strongly positive (+++) based on the staining intensity of endothelial cells. In these experiments, brain and liver tissues were placed next to each other in frozen tissue blocks so that the two tissues could be sectioned together and processed simultaneously. Four brain endothelial markers were localized to ECs throughout the brain whereas expression in liver was undetectable (Table 10). Similarly, an analysis of five liver endothelial markers revealed that each was readily detectable in liver endothelium but not brain endothelium. Liver endothelial markers were expressed predominantly in the sinusoidal ECs with a pattern of staining similar to that of the endothelial control VEGFR2 (Table 10). However, LEM5, a previously uncharacterized putative G-protein coupled receptor, was also found in the larger vessels of central veins, portal veins and hepatic arteries

TABLE 10

In situ hybrization of brain endothelial markers and liver endothelial markers in normal adult brain and liver tissues.

| | | Liver capillaries (Sinusoidal ECs) | Liver large vessel ECs[†] (CV, PV & HA) | Brain ECs |
|---|---|---|---|---|
| Controls | CD31 | + | +++ | + |
| | VEGFR2 | +++ | − | ++ |
| Brain Endothelial Markers | BEM1 (GLUT-1) | − | − | +++ |
| | BEM2 (Oat2) | − | − | ++ |
| | BEM3 (Ptn) | − | − | ++[§] |
| | BEM4 (Atp10a) | − | − | + |
| Liver Endothelial Markers | LEM1 (Dnase1l3) | +++ | − | − |
| | LEM2 (Oit3) | +++ | − | − |
| | LEM5 (Csprs) | ++ | ++ | − |
| | LEM6 (Clec1b) | + | − | − |
| | LEM8 (Plxnc1) | +++ | − | −* |

[†]CV: central vein; PV: portal vein; HA: hepatic artery
[§]Pericytes appear to be responsible for predominant staining of blood vessels and neuronal cells are also positive.
*Negative for blood vessel staining but some neuronal cells are positive.

Localization of mRNA in ECs (red stain) was demonstrated by examining Oatp2, a representative brain endothelial marker in brain tissue (FIG. 3, panel a), and various tumor endothelial markers in tumor tissues including CD276, ETSvg4, Apelin, CD109, MiRP2, CD137, Doppel and Vscp, as illustrated in FIG. 3 panel b through i, respectively. Panels (b) and (c) depict HCT116 tumors grown subcutaneously, FIGS. 3D-3F depict SW620 tumors grown subcutaneously, and FIGS. 3G and 3F depict KM12 tumors grown in the liver. A dilute counterstain was applied to the sections to highlight the lack of detectable expression in the non-ECs of the tumors. These signals were specific because their patterns matched those observed with endothelial control probes such as VE-cadherin and von Willebrand factor (vWF), and omission of the antisense riboprobes or substitution with a sense control resulted in a loss of signal in each case. The data demonstrate that the disclosed tumor endothelial markers are expressed predominantly by the vessels within each of the tumors.

Example 5

Co-Localization of CD276 with vWF in Human Colon Cancer

This example illustrates that the differential expression of CD276 (a tumor endothelial marker) is maintained at the protein level in human colorectal cancer and demonstrates that CD276 can be used for tumor-specific vascular targeting.

Figure 4:
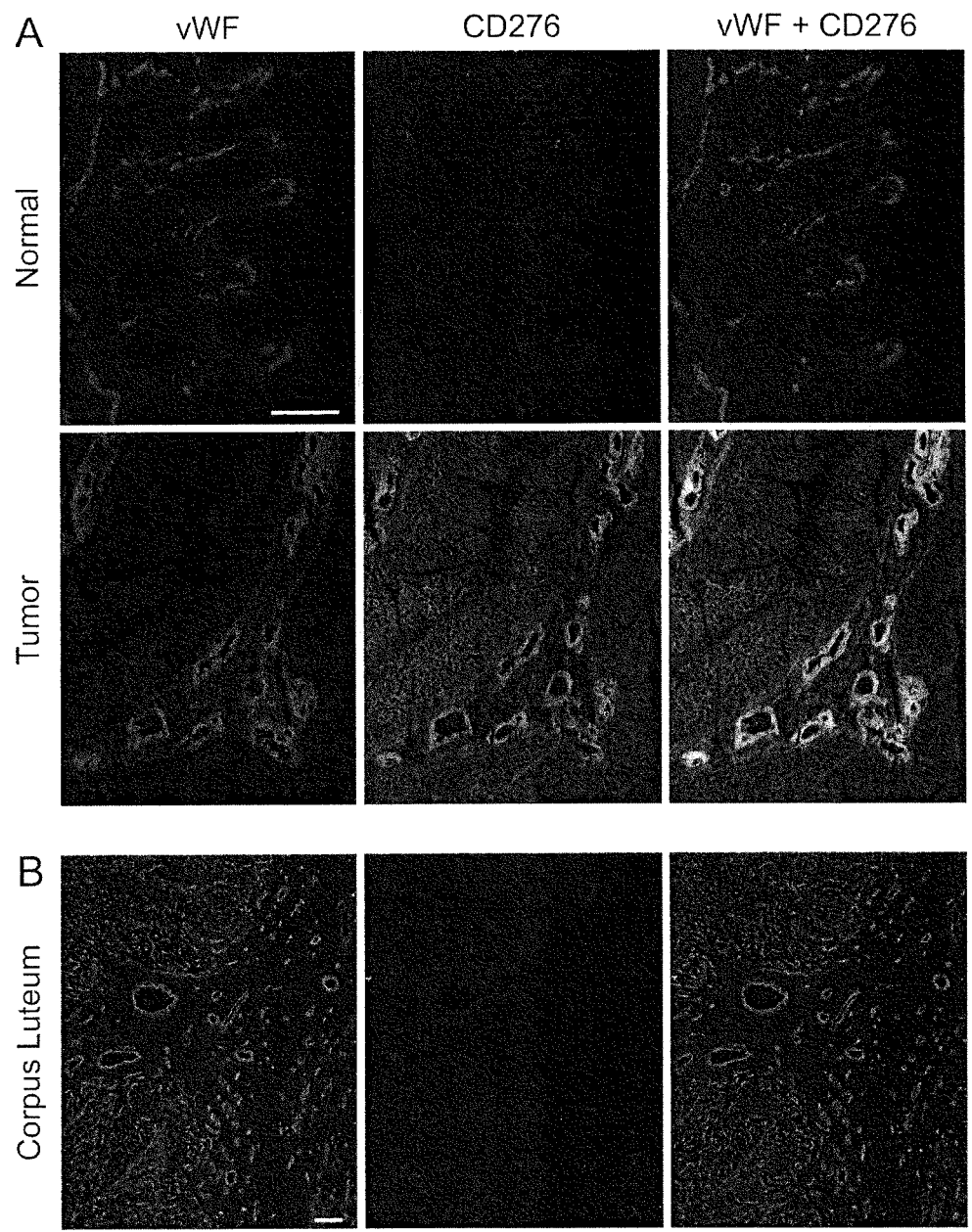
FIG. 4A includes digital images of human colon samples stained with immunoflurescently labeled CD276 and von Willebrand factor (vWF). CD276 was expressed predominantly by the tumor vessels of the colorectal cancer, but was also expressed at a lower level by the tumor cells themselves. Expression of CD276 in normal colonic mucosa was undetectable (top middle panel). As a control, vessels were stained for vWF, which co-localized with CD276 only in the tumor sample. Scale bar, 100 μm.
FIG. 4B includes digital images of angiogenic vessels of the developing corpus luteum stained with immunoflurescently-labeled CD276. CD276 expression was undetectable in the angiogenic vessels of the developing corpus luteum. Sections were counterstained with DAPI which is shown in the left panels to highlight the epithelial cells. Scale bar, 200 μm.

To demonstrate that protein expression patterns of the disclosed tumor endothelial markers followed mRNA expression patterns, co-immunofluorescence studies with antibodies against CD276, the most differentially expressed cell surface receptor identified, and the endothelial marker vWF were performed using 6 normal and 6 malignant colorectal tissues. As illustrated in FIG. 4A, CD276 was expressed predominantly by the tumor vessels of the colorectal cancer, but was also expressed at a lower level by the tumor cells themselves. Expression of CD276 in normal colonic mucosa was undetectable (top middle panel). As a control, vessels were stained for vWF, which co-localized with CD276 only in the tumor sample.

The human corpus luteum was stained to determine if the normal angiogenic vessels of this tissue express CD276. Unlike the vWF control, CD276 expression was undetectable in the angiogenic vessels of the developing corpus luteum (see FIG. 4B). Sections were counterstained with DAPI (left panels of FIG. 4B) to highlight the epithelial cells.

These results demonstrate that the differential expression of CD276 is maintained at the protein level in human colorectal cancer and indicate that CD276 is a useful target for tumor-specific vascular targeting.

Example 6 mRNA is Expressed in Human Colorectal Cancer Vessels

This example illustrates that CD276 mRNA is expressed in human colorectal cancer and indicates that CD276 can be used for tumor-specific vascular targeting.

Riboprobes against human CD276 were generated and mRNA in situ hybridization on normal and malignant colorectal tissues was performed.

Figure 5:
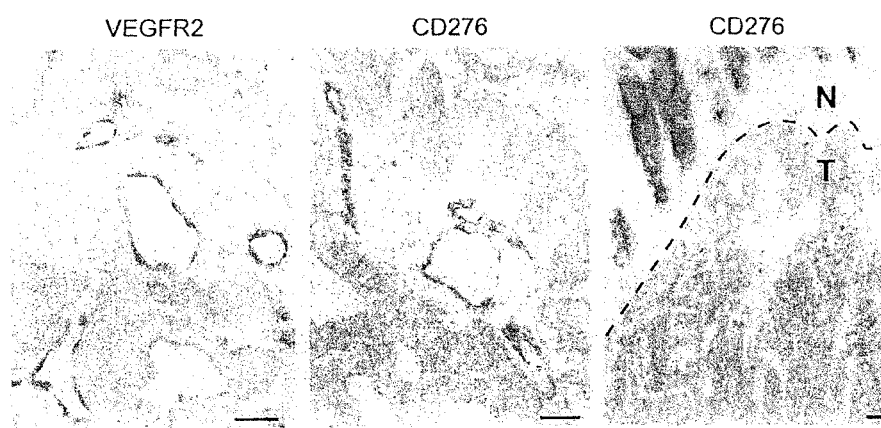
FIG. 5 includes digital images of vessels of human colorectal cancer. In situ hybridization revealed that CD276 mRNA is expressed predominantly in the vessels of human colorectal cancer (middle panel) with a pattern of staining similar to that of the control endothelial marker VEGFR2 (left panel). In the case of CD276 the tumor cells also display positive staining, albeit less intense. At the margin between tumor (T) tissue and normal (N) colonic mucosa CD276 staining abruptly ends (right panel). The extracellular staining around the normal crypts represents non-specific binding of the in situ hybridization reagents to the mucous (right panel) and is also present in control sections. Scale bars, 50 μM.

As shown in FIG. 5, CD276 mRNA was most prominent in the tumor vessels, with a pattern of expression similar to that of the endothelial control VEGFR2 (left panel). CD276 expression was also detected in the tumor cells themselves, albeit at a lower level. In contrast, CD276 expression was undetectable in normal colonic mucosa, and an analysis of the tumor margin showed a striking on/off pattern of staining at the tumor/normal border (FIG. 5, right panel). For instance, the margin between tumor (T) tissue and normal (N) colonic mucosa CD276 staining abruptly ends (right panel). Further, extracellular staining around the normal crypts was observed and represents non-specific binding of the in situ hybridization reagents to the mucous (right panel); similar staining was also detected in control sections.

These results demonstrate that CD276 mRNA is expressed in human colorectal cancer and indicate that CD276 is a target for tumor-specific vascular targeting.

Example 7

CD276 Protein is Overexpressed in Human Tumors

This example illustrates that CD276 is overexpressed in human tumors and indicates that CD276 is a target for tumor-specific vascular targeting.

CD276 protein expression patterns were evaluated using anti-CD276 antibodies. The overall level of CD276 was assessed in extracts taken from 12 normal and 12 malignant colorectal tissues, 10 of which were derived from the same patient (P1-P10). As shown in FIG. 6A, CD276 was clearly elevated in 11 of the 12 tumors, while the remaining matched normal/tumor pair (case P7) displayed unaltered expression. CD276 protein migrated at a size similar to that observed in 293 cells transfected with the 4IgG-containing form of CD276 (293/CD276). The faint product present in 293 parent cells may represent low-level endogenous CD276 expression which was also detected at the mRNA level in these cells by RT-PCR.

CD276 protein expression levels were assessed in 6 lung tumor samples. As illustrated in FIG. 6B, CD276 protein expression levels were increased in each of the lung tumor samples as compared with protein levels detected in patient-matched control samples. All tumor samples appeared to overexpress the predominant 4-IgG form of CD276, as exogenous overexpression of this form in transfected 293 cells resulted in a product of similar size (FIG. 6A).

To determine the cellular source of this up-regulated protein, immunohistochemistry was performed on paraffin sections obtained from 10 patient-matched samples of normal colonic mucosa and colorectal cancer. Ten patient-matched samples of non-small cell lung cancer were also analyzed along with adjacent normal lung tissue. All samples represented different cases than those used for the western analysis. Staining with a CD276 polyclonal antibody revealed a vessel-like pattern in all cases of human colorectal or lung cancer analyzed, but not in matched normal tissues (FIGS. 6C-6H and Table 11).

Moreover, this vessel-like pattern of staining was also observed in each of a smaller number of breast, esophageal and bladder cancers, but not in corresponding normal tissues (FIGS. 6I-6L). Similar expression patterns were observed using an independent monoclonal antibody. CD276 overexpression was frequently detected in the tumor cells while normal epithelium was uniformly negative. The highest tumor-cell expression levels of CD276 were found in lung and breast cancer where they matched that found in tumor endothelium (FIGS. 6F, 6G and 6L). These results demonstrate that CD276 protein is overexpressed in multiple types of human tumors and demonstrate that CD276 is a target for tumor-specific vascular targeting.

TABLE 11

Immunohistological staining of CD276 in normal and tumor tissues.

|  | Vessel staining[†] | | Epithelial/tumor cell staining | |
| --- | --- | --- | --- | --- |
|  | Normal | Tumor | Normal | Tumor |
| Colon | 0/10 | 10/10 | 0/10 | 0/10* |
| Lung | 0/10 | 10/10 | 0/10 | 5/10 |
| Breast | 0/3 | 3/3 | 0/3 | 3/3 |
| Bladder | 0/2 | 3/3 | 0/2 | 3/3 |
| Esophagus |  | 4/4 |  | 1/4 |

Figure 6:
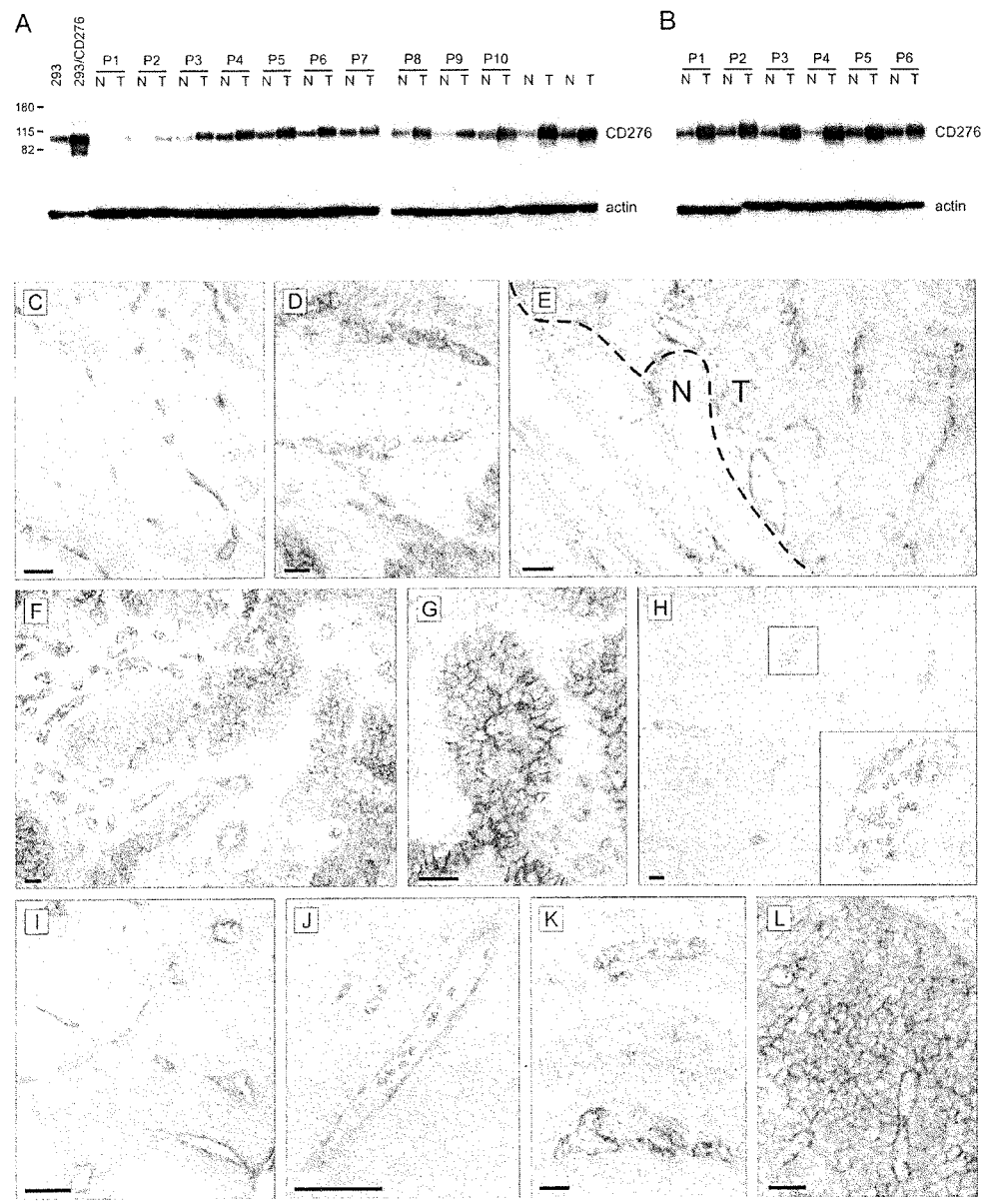
FIG. 6A is a digital image of an immunoblot including colorectal tumor (T) and normal (N) colonic mucosa samples. Immunoblotting with a CD276 monoclonal antibody revealed an upregulation of CD276 protein in colorectal tumors (T) compared to normal (N) colonic mucosa.
FIG. 6B is a digital image of an immunoblot including lung tumor (T) and normal (N) adjacent lung tissue samples. Immunoblotting with a CD276 monoclonal antibody revealed an upregulation of CD276 protein in lung tumors (T) compared to normal (N) adjacent lung tissue. The normal tissues in A and B were classified as normal based on gross morphology, but microscopic disease or inflammatory host cells may have contributed to the low level CD276 expression observed in these tissues.
FIGS. 6C-6L are digital images of various samples stained with a polyclonal CD276 antibody. Immunohistochemical staining with a polyclonal CD276 antibody revealed a vessel-like pattern in colorectal cancer (C-E), non-small cell lung cancer (F-H), esophageal cancer (I-J), bladder cancer (K) and breast cancer (L). At the tumor margin (E) CD276 staining was weak or undetectable in normal colonic mucosa (N) but strong in the vessels of the adjacent tumor region (T). Vessels from normal tissues that failed to stain for CD276 were immunoreactive on control serial sections stained for endothelial proteins such as vWF. In some tumors, the vessels stained most prominently (C-E and H-K) whereas in others, both tumor cells and tumor vessels were strongly positive (F-G and L). A strong cell surface staining pattern in the tumor epithelium was detected under high power magnification (G). Many of the blood vessels were readily identified by the presence of blood cells in the lumen; for example see inset displaying higher power magnification of boxed region in (H). Sections were lightly counterstained with hematoxylin. Scale bar, 50 μM.

*CD276 immunoreactivity in the tumor cells was considered negative in all colon samples by IH because expression levels were close to background, but could be detected in the same cells using a more sensitive IF protocol (see FIG. 4).
[†]Vessel staining refers to that which lines the inner surface of vessels as shown in FIG. 6. Occasional staining of the outer adventitia was also observed in some larger blood vessels, particularly in lung tissues, but is not included here. All normal tissue used was patient-matched to the tumor samples. Vessels from normal tissues that failed to stain for CD276 were immunoreactive on control sections stained for endothelial proteins such as vWF.

Example 8

Inhibition of Pathological Angiogenesis to Treat a Tumor

This example describes methods that can be used to significantly reduce pathological angiogenesis, for example as a means to treat a tumor, such as cancer. One skilled in the art will appreciate that similar methods can be used with any of the pathological angiogenesis inhibitors shown in Table 9 to treat any tumor that expresses the target angiogenesis protein.

Based upon the teaching disclosed herein, pathological angiogenesis can be reduced or inhibited by administering a therapeutically effective amount of a composition, wherein the composition includes a specific binding agent that preferentially binds to one or more pathological angiogenesis marker proteins comprising Vscp, CD276, ETSvg4 (Pea3), CD137(4-1BB), MiRP2, Ubiquitin D (Fat10), Doppel (prion-PLP), Apelin, Plgf, Ptprn (IA-2), CD109, Ankylosis, and collagen VIIIα1, thereby inhibiting pathological angiogenesis in the subject.

In an example, a subject who has been diagnosed with a disease associated with or caused by pathological angiogenesis such as a tumor is identified. Following subject selection, a therapeutic effective dose of the composition including the specific binding agent is administered to the subject. For example, a therapeutic effective dose of a specific binding agent to one or more of the disclosed pathological angiogenesis markers is administered to the subject to inhibit pathological angiogenesis. In a further example, the specific binding agent is an antibody conjugated to a therapeutic molecule (such as therapeutic molecule is a cytotoxin, chemotherapeutic reagent, radionucleotide or a combination thereof). The amount of the composition administered to prevent, reduce, inhibit, and/or treat pathological angiogenesis or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the disorder (e.g., cancer) in a subject without causing a substantial cytotoxic effect in the subject.

In one specific example, naked antibodies are administered at 5 mg per kg every two weeks or 10 mg per kg every two weeks depending upon the cancer. In an example, the antibodies are administered continuously. In another example, antibodies or antibody fragments conjugated to cytotoxic agents (immunotoxins) are administered at 50 μg per kg given twice a week for 2 to 3 weeks.

Example 9

Screening of Subjects for Pathological Angiogenesis

According to the teachings herein, pathological angiogenesis can be screened for by detecting at least one expression product comprising one or more of: Vscp, CD276, ETSvg4 (Pea3), CD137(4-1BB), MiRP2, Ubiquitin D (Fat10), Doppel (prion-PLP), Apelin, Plgf, Ptprn (IA-2), CD109, Ankylosis, and collagen VIII, 1, in a sample obtained from the subject and compared to a control (sample obtained from a subject without pathological angiogenesis) or reference value. In one example, detection of the at least one expression product indicates pathological angiogenesis in the subject. In a further example, detection of the at least one expression product indicates the presence of a tumor such as cancer. The expression product can be RNA or protein. An RNA expression product can be detected by SAGE or PCR by methods described above (see, for example, Example 1). A protein expression product can be detected by Western blot or immunoassay (see, for example, Example 1). However, the disclosure is not limited to particular methods of detection.

Example 10

Delivering a Therapeutic Agent to Organ-Specific Cells

Based upon the teaching disclosed herein, a therapeutic agent can be delivered to organ-specific cells by administering a therapeutically effective amount of a composition, wherein the composition includes a binding agent that preferentially binds to one or more of the disclosed brain endothelial marker proteins or liver endothelial markers and the therapeutic agent, thereby evoking a therapeutic response in the organ-specific endothelial cells. The one or more brain endothelial markers can include Glucose transporter GLUT-1, Organic anion transporter 2, Pleiotrophin, ATPase class V, type 10A, Peptidoglycan recognition protein 1, Organic anion transporter 14, Forkhead box Q1, Organic anion transporter 3, SN2 (Solute carrier family 38, member 5), Inter-alpha (globulin) inhibitor H5, Solute carrier 38 member 3, Zinc finger protein of the cerebellum 2, Testican-2,3-HMG-CoA synthase 2, Progestin and adipoQ receptor family member V, APC down-regulated 1 Drapc1, GDPD phosphodiesterase family Accession No. NM_001042671, putative transmembrane protein Accession No. NM_029001, DES2 lipid desaturase/C4-hyroxylase, Kelch repeat and BTB (POZ) domain, Lipolysis stimulated receptor, Glutathione S-transferase alpha 4, TNF receptor superfamily member 19, T-box 1 or putative secreted protein Accession No. XM_620023. The one or more liver endothelial markers can include liver endothelial marker proteins such as deoxyribonuclease 1-like 3, LZP oncoprotein induced transcript 3, putative transmembrane protein Accession No. NM_023438, CD32 15, putative G-protein coupled receptor NM_033616, C-type lectin-like receptor 2, C-type lectin domain family 4 member g 16, Plexin C1, Wnt9B, Accession No. AK144596, GATA-binding protein 4, MBL-associated serine protease-3, Renin binding protein, putative transmembrane protein Accession No. NM_144830, or Retinoic acid receptor, beta.

In an example, a subject who is in need of delivery of a therapeutic agent to either a brain endothelial cell or a liver endothelial cell is identified. Following subject selection, a therapeutic effective dose of the composition including the specific binding agent is administered to the subject. For example, a therapeutic effective dose of a specific binding agent to one or more of the disclosed pathological angiogenesis markers is administered to the subject to inhibit tumor growth in the brain or liver. The specific binding agent can be an antibody to one or more of the organ-specific endothelial markers in which the antibody is conjugated to the therapeutic agent such as a cytotoxin, chemotherapeutic reagent, radionucleotide or a combination thereof.

In view of the many possible embodiments to which the principles of the disclosure may be applied, it should be recognized that the illustrated examples are only examples of the disclosed matter and should not be taken as limiting the scope of the disclosure. Rather, the scope of the disclosure is defined by the following claims. We therefore claim as our invention all that comes within the scope and spirit of these claims.

We claim:

1. A method of determining pathological angiogenesis, comprising:
   contacting a sample obtained from a subject with a CD276 probe or primer set and a Ptprn (IA-2) probe or primer set;
   detecting at least two expression products comprising CD276 and Ptprn (IA-2) in a sample obtained from the subject by performing an assay that detects both CD276 and Ptprn (IA-2); and
   determining the presence of pathological angiogenesis in the subject by comparing expression level of CD276 RNA/protein and Ptprn (IA-2) RNA/protein in the sample obtained from the subject with the expression level of CD276 RNA/protein and Ptprn (IA-2) RNA/protein in a control sample wherein detection of an increase in expression of the at least two expression products as compared to expression of the at least two expression products in a control sample indicates pathological angiogenesis.

2. The method of claim 1, wherein the at least two expression products further comprises detecting the expression of CD137(4-1BB), MiRP2, Apelin, ankylosis, or a combination thereof.

3. The method of claim 1, wherein detection of an increase in expression of the at least two expression products indicates the presence of a tumor.

4. The method of claim 3, wherein the expression products are RNA or a protein.

5. The method of claim 3, wherein the tumor is a cancer of the colon, liver, lung, or breast.

6. The method of claim 1, wherein the detecting the expression products is performed using serial analysis gene expression (SAGE), polymerase chain reaction, Western blot, immunoassay, microscopy, flow cytometry, or spectrometry, or a combination thereof.

7. The method of claim 1, wherein the sample is serum sample.

8. The method of claim 1, wherein the CD276 primer set includes a first primer with a nucleic acid sequence set forth as SEQ ID NO: 211 and a second primer with a nucleic acid set forth as SEQ ID NO: 212 and the Ptprn (IA-2) primer set includes a first primer with a nucleic acid sequence set forth as SEQ ID NO: 227 and a second primer with a nucleic acid set forth as SEQ ID NO: 228.

* * * * *